United States Patent
Castle

(10) Patent No.: US 12,127,773 B2
(45) Date of Patent: Oct. 29, 2024

(54) ORTHOPEDIC FIXATION SYSTEM AND METHODS OF USE THEREOF

(71) Applicant: DEPUY SYNTHES PRODUCTS, INC., Raynham, MA (US)

(72) Inventor: Richard W. Castle, Honey Brook, PA (US)

(73) Assignee: DePuy Synthes Products, Inc., Raynham, MA (US)

(*) Notice: Subject to any disclaimer, the term of this patent is extended or adjusted under 35 U.S.C. 154(b) by 30 days.

(21) Appl. No.: 17/841,168

(22) Filed: Jun. 15, 2022

(65) Prior Publication Data

US 2023/0404637 A1 Dec. 21, 2023

(51) Int. Cl.
A61B 17/80 (2006.01)
A61B 17/68 (2006.01)

(52) U.S. Cl.
CPC .... *A61B 17/8004* (2013.01); *A61B 2017/681* (2013.01)

(58) Field of Classification Search
CPC ............ A61B 17/8004; A61B 17/8023; A61B 2017/681
See application file for complete search history.

(56) References Cited

U.S. PATENT DOCUMENTS

| | | | |
|---|---|---|---|
| 7,591,840 B2 | 9/2009 | Suddaby | |
| 7,635,366 B2 | 12/2009 | Abdou | |
| 7,993,380 B2 | 8/2011 | Hawkes | |
| 8,070,749 B2 * | 12/2011 | Stern | A61B 17/86 606/71 |
| 8,083,781 B2 | 12/2011 | Reimels et al. | |
| 8,262,711 B2 | 9/2012 | Hess | |
| 8,556,895 B2 * | 10/2013 | Stern | A61B 17/8872 606/280 |

(Continued)

FOREIGN PATENT DOCUMENTS

| | | |
|---|---|---|
| WO | 9713469 A1 | 10/1995 |
| WO | 2016025162 A1 | 2/2016 |

OTHER PUBLICATIONS

Tarnita et al., In vitro experiment of the modular orthopedic plate based on Nitinol, used for human radius bone fractures, Romanian Journel of Morphology and Embryology, 51(2): 315-320, 2010.

*Primary Examiner* — Anu Ramana
(74) *Attorney, Agent, or Firm* — Christopher L. Makay

(57) ABSTRACT

An orthopedic fixation system includes an orthopedic implant and a compression insert transitionable between a natural shape and an insertion shape. The orthopedic implant includes first and second plates with insert slots configured to receive therein a portion of the compression insert. The first and second plates secure with a bone in an opposed relationship while being separated by an expansion whereby the insert slots of the first and second plates align across the expansion. The compression insert, in the insertion shape, inserts into the insert slots of the first and second plates such that the compression insert spans the expansion. The compression insert, due to an attempted transition thereof from the insertion shape to the natural shape, delivers energy stored therein to the first plate and the second plate whereby the orthopedic implant affixes the bone.

13 Claims, 57 Drawing Sheets

(56) References Cited

U.S. PATENT DOCUMENTS

| | | | |
|---|---|---|---|
| 8,814,915 B2* | 8/2014 | Hess | A61B 17/7059 |
| | | | 606/279 |
| 8,858,604 B2 | 10/2014 | Biyani et al. | |
| 8,974,504 B2* | 3/2015 | Hess | A61B 17/8028 |
| | | | 606/282 |
| 9,095,388 B2* | 8/2015 | Hess | A61B 17/8009 |
| 9,381,046 B2* | 7/2016 | Perrow | A61B 17/1728 |
| 9,408,647 B2 | 8/2016 | Cheney | |
| 9,675,395 B2 | 6/2017 | Averous et al. | |
| 11,179,149 B2* | 11/2021 | Hartdegen | A61B 17/17 |
| 11,331,130 B1* | 5/2022 | Lui | A61B 17/0642 |
| 11,406,390 B2* | 8/2022 | Shelton, IV | A61B 17/122 |
| 11,576,703 B2* | 2/2023 | Jackson, III | A61B 17/7059 |
| 2006/0235405 A1* | 10/2006 | Hawkes | A61B 17/8023 |
| | | | 606/911 |
| 2016/0213407 A1* | 7/2016 | Stern | A61B 17/7059 |
| 2017/0172634 A1 | 6/2017 | Palmer et al. | |
| 2017/0367741 A1 | 12/2017 | Morgan et al. | |
| 2021/0251661 A1* | 8/2021 | Kay | A61B 17/8004 |

* cited by examiner

ORTHOPEDIC FIXATION SYSTEM AND METHODS OF USE THEREOF

BACKGROUND OF THE INVENTION

1. Field of the Invention

The present invention relates generally to orthopedic fixation and, more particularly, but not way of limitation, to an orthopedic fixation system including an implant and a compression insert.

2. Description of the Related Art

Orthopedic fixation systems commonly used in surgical procedures requiring a reattachment or fusing of bone, bones, or bone pieces include shape memory implants. The shape memory implants typically are composed of a shape memory material such as Nitinol that allows a shape memory implant to have a first final shape and the ability to transition into a second shape. Shape memory implants either can be thermally activated, in which an external heating source or body temperature would be required to activate the implants, or mechanically activated, in which a constraining instrument would be required. A shape memory implant that requires mechanical constraint stores mechanical energy due to elastic (recoverable) deformation, and then releases the stored mechanical energy when the constraining instrument is removed. In these types of implants, the implants are mechanically deformed into their second shape and maintained in their second shape by instrumentation such that, upon release from the instrumentation, the implants elastically return to their first final shape from their second shape. Although thermally activated shape memory implants may be used without a constraining instrument, thermally activated shape memory implants often include a mechanical constraint in order to prevent premature activation prior to implantation in the event of exposure to a heat source.

In surgical procedures, the elastic or thermal properties of constrained shape memory implants are used as follows. Bone, bones, or bone pieces requiring fixating are aligned in a desired orientation, and the shape memory implant, which has been mechanically deformed to the second shape, is maintained in instrumentation and then inserted across a fixation zone of the bone, bones, or bone pieces. After insertion, the shape memory implant is released from the instrumentation, whereupon the shape memory implant elastically or upon heating attempts to return from the second shape to the first final shape such that the shape memory implant delivers the mechanical energy stored therein thereby maintaining the bone, bones, or bone pieces fixated in the desired orientation. In accordance therewith, the shape memory implant, because it stores mechanical energy, continuously applies a force to the bone, bones, or bone pieces as the shape memory implant attempts to transition from the second shape to the first final shape that aids in the healing process through the affixing of the bone, bones, or bone pieces in the desired orientation.

Although shape memory implant orthopedic fixation systems enhance the healing process in bone, bones, or bone pieces through a continuous application of a fixating force thereto, certain orthopedic surgical procedures, such as, for example, a patella repair procedure, would benefit from a continuous application of a force delivered without use of an implant experiencing a change in shape. In accordance therewith, an orthopedic fixation system that continuously applies a force to fixate bone, bones, or bone pieces without use of a shape changing implant would be beneficial in orthopedic fixation.

SUMMARY OF THE INVENTION

In accordance with the present invention, an orthopedic fixation system configured to affix bone, bones, or bone pieces includes an orthopedic implant and a compression insert transitionable between a natural shape and an insertion shape. The compression insert, upon transition from the natural shape to the insertion shape stores energy, and the compression insert, upon transition from the insertion shape to the natural shape, delivers the energy stored therein. The orthopedic implant includes a first plate and a second plate, each of which includes an insert slot configured to receive therein a portion of the compression insert. The first plate and the second plate in an insertion position secure with the bone, bones, or bone pieces in an opposed relationship and separated by an expansion such that the insert slots of the first plate and the second plate align across the expansion. The compression insert, in the insertion shape, inserts into the insert slot of the first plate and the insert slot of the second plate such that the compression insert spans the expansion. The compression insert, due to an attempted transition thereof from the insertion shape to the natural shape, delivers the energy stored therein to the first plate and the second plate whereby the orthopedic implant affixes the bone, bones, or bone pieces.

The compression insert includes a closed position when residing in the natural shape and an open position when residing in the insertion shape. The compression insert in a first configuration includes a transition section while terminating in a first end and a second end defining a gap therebetween. The transition section and the gap facilitate transition of the compression insert between the natural shape and the insertion shape. The compression insert in the closed position includes a first width, and the compression insert in the open position includes a second width that is greater than the first width.

The compression insert in a second configuration includes a shaft terminating at a first end in a first beam having a first transition section and at a second end in a second beam having a second transition section. The first transition section and the second transition section in the natural shape of the compression insert contract respectively the first beam and the second beam into the closed position. The first transition section and the second transition section in the insertion shape of the compression insert expand respectively the first beam and the second beam into the open position.

The compression insert in a third configuration includes a shaft terminating at a first end in a first beam including a first transition section that, in the natural shape of the compression insert contracts the first beam into the closed position, and, in the insertion shape of the compression insert, expands the first beam into the open position. The shaft includes a first shaft segment with a first shaft segment transition section terminating at a second end. The shaft includes a second shaft segment with a second shaft segment transition section terminating at the second end. The first shaft segment transition section and the second shaft segment transition section in the natural shape of the compression insert contract respectively the first shaft segment and the second shaft segment into a closed position. The first shaft segment transition section and the second shaft segment transition section in the insertion shape of the compression insert expand respectively the first shaft segment and the second shaft segment into an open position. The first shaft segment terminates in a first hook including a first hook transition section. The second shaft segment terminates in a second hook including a second hook transition section. The first hook transition section and the second hook transition section in the natural shape of the compression insert contract respectively the first hook and the second hook into a closed position. The first hook transition section and the second hook transition section in the insertion shape of the compression insert expand respectively the first hook and the second hook into an open position.

The first plate and the second plate both include a body section with a front face, whereby the body section includes the insert slot therein. The first plate and the second plate both include an anchoring section extending from the body section that is configured to secure the first plate or the second plate with the bone, bones, or bone pieces. The insert slot of the first plate, the insert slot of the second plate, and the expansion, when the first plate and the second plate reside in the insertion position, define an insert retaining pathway with dimensions substantially equal to the compression insert when transitioned to the open position such that the insert retaining pathway receives therein the compression insert in the insertion shape. The expansion includes a width selected to locate the insert slot of the first plate away from the insert slot of the second plate a distance that provides the insert retaining pathway with a width substantially equal to the second width of the compression insert in the closed position such that the insert retaining pathway receives therein the compression insert in the insertion shape.

The first plate may be divided into a first plate segment including a first insert slot segment and a second plate segment including a second insert slot segment. The first plate in the insertion position secures with the bone, bones, or bone pieces such that the first plate segment and the second plate segment are separated by an expansion while the first insert slot segment and the second insert slot segment align across the expansion. The compression insert, in the insertion shape, inserts into the first insert slot segment and the second insert slot segment such that the compression insert spans the expansion between the first insert slot segment and the second insert slot segment. The compression insert further inserts into the insert slot of the second plate such that the compression insert spans the expansion between the first plate and the second plate. The compression insert, due to an attempted transition thereof from the insertion shape to the natural shape, delivers the energy stored therein to the first plate and the second plate whereby the orthopedic implant affixes the bone, bones, or bone pieces. The first insert slot segment, the second insert slot segment, the expansion between the first plate segment and the second plate segment, the insert slot of the second plate, and the expansion between the first plate and the second plate, when the first plate and the second plate reside in the insertion position, define an insert retaining pathway with dimensions substantially equal to the compression insert when transitioned to the open position such that the insert retaining pathway receives therein the compression insert in the insertion shape.

The second plate may be divided into a first plate segment including a first insert slot segment and a second plate segment including a second insert slot segment. The second plate in the insertion position secures with the bone, bones, or bone pieces such that the first plate segment and the second plate segment are separated by an expansion while the first insert slot segment and the second insert slot segment align across the expansion. The compression insert, in the insertion shape, inserts into the first and second insert slot segments of the first and second plate segments of the first and second plates such that the compression insert spans the expansion between the first and second insert slot segments of the first and second plate segments of the first and second plates and the expansion between the first plate and the second plate. The compression insert, due to an attempted transition thereof from the insertion shape to the natural shape, delivers the energy stored therein to the first plate and the second plate whereby the orthopedic implant affixes the bone, bones, or bone pieces. The first and second insert slot segments of the first and second plate segments of the first and second plates, the expansions between the first and second plate segments of the first and second plates, and the expansion between the first plate and the second plate, when the first plate and the second plate reside in the insertion position, define an insert retaining pathway with dimensions substantially equal to the compression insert when transitioned to the open position such that the insert retaining pathway receives therein the compression insert in the insertion shape.

In an embodiment for use with the compression insert according the second configuration, the insert slot in each of the first plate and the second plate includes a chamber communicating with a channel defining an opening at the front face. The channel is configured to receive therein a portion of the shaft of the compression insert. The chamber is configured to receive therein one of the first beam and the second beam expanded into the open position while allowing a contraction of one of the first beam and the second beam into the closed position. The chamber and the channel of the insert slot of the first plate, the chamber and the channel of the insert slot of the second plate, and the expansion, when the first plate and the second plate reside in the insertion position, define an insert retaining pathway with dimensions substantially equal to the compression insert when transitioned to the open position such that the insert retaining pathway receives therein the compression insert in the insertion shape.

The orthopedic implant may incorporate an expander plate including a first insert slot configured to receive therein a portion of a first compression insert and a second insert slot configured to receive therein a portion of a second compression insert. The expander plate in an insertion position secures with the bone, bones, or bone pieces between the first plate and the second plate such that the expander plate is separated from each of the first plate and the second plate by an expansion while the insert slot of the first plate and the first insert slot of the expander plate align across the expansion and the insert slot of the second plate and the second insert slot of the expander plate align across the expansion. The first compression insert, in the insertion shape, inserts into the insert slot of the first plate and the first insert slot of the expander plate such that the compression insert spans the expansion. The compression insert, due to an attempted transition thereof from the insertion shape to the natural shape, delivers the energy stored therein to the first plate and the expander plate whereby the orthopedic implant affixes the bone, bones, or bone pieces. The second compression insert, in the insertion shape, inserts into the insert slot of the second plate and the second insert slot of the expander plate such that the compression insert spans the expansion. The compression insert, due to an attempted transition thereof from the insertion shape to the natural shape, delivers the energy stored therein to the second plate and the expander plate whereby the orthopedic implant affixes the bone, bones, or bone pieces.

In an embodiment for use with the compression insert according the third configuration, the first plate may be divided into a first plate segment including a first insert slot segment defining a hook chamber communicating with a shaft segment channel and a second plate segment including a second insert slot segment defining a hook chamber communicating with a shaft segment channel. The first plate in the insertion position secures with the bone, bones, or bone pieces, whereby the first plate segment and the second plate segment are separated by an expansion. The compression insert, in the insertion shape, is configured such that the first hook and the second hook in the open position insert respectively into the hook chambers of the first and second insert slot segments, the first shaft segment and the second shaft segment in the open position insert respectively into the shaft segment channels of the first and second insert slot segments, and the shaft and the first beam insert into the insert slot of the second plate. Once inserted, the compression insert spans the expansion between the first plate and the second plate at the expansion between the first plate segment and the second plate segment. The compression insert, due to an attempted transition thereof from the insertion shape to the natural shape, delivers the energy stored therein to the first plate and the second plate whereby the orthopedic implant affixes the bone, bones, or bone pieces. The first insert slot segment, the second insert slot segment, the expansion between the first plate segment and the second plate segment, the insert slot of the second plate, and the expansion between the first plate and the second plate, when the first plate and the second plate reside in the insertion position, define an insert retaining pathway with dimensions substantially equal to the compression insert when transitioned to the open position such that the insert retaining pathway receives therein the compression insert in the insertion shape. The hook chambers of the first and second insert slot segments are configured to receive therein respectively one of the first and second hooks expanded into the open position while allowing a contraction of one of the first and second hooks into the closed position.

The second plate may be divided into a first plate segment including a first insert slot segment comprising a hook chamber communicating with a shaft segment channel and a second plate segment including a second insert slot segment comprising a hook chamber communicating with a shaft segment channel. The second plate in the insertion position secures with the bone, bones, or bone pieces, whereby the first plate segment and the second plate segment are separated by an expansion.

The first plate at thereof front face may include a stabilizer extending therefrom. The second plate at the front face may define therein a cavity configured complementary in shape with the stabilizer. The stabilizer, when the first plate and the second plate reside in the insertion position, is configured to insert into the cavity in order to prevent a load experienced by the first plate and the second plate from moving the first plate and the second plate.

The orthopedic fixation system may include an insert retainer projecting over the insert slot of one of the first plate and the second plate. The insert retainer blocks the compression insert within the insert slot as the compression insert attempts transition from the insertion shape to the natural shape.

The orthopedic fixation system may include an implant retainer that inserts into the expansion between the first plate and the second plate. The implant retainer is configured to prevent transition of the compression insert from the insertion shape to the natural shape thereby maintaining the orthopedic implant in the insertion position.

The orthopedic fixation system of claim 1 may include an insert delivery device. The insert delivery device includes a barrel with a shaft extending therefrom. The shaft is configured to receive the compression insert in the insertion shape. The insert delivery device includes a plunger with a blade extending therefrom. The plunger integrates with the barrel such that the blade extends along the shaft. The plunger is moveable between a pre-delivery position that allows loading of the compression insert in the insertion shape onto the shaft and a delivery position whereby the blade pushes the compression insert from the shaft.

In the alternative, the insert delivery device includes a barrel with a conduit extending therefrom that terminates in an insert receiver shaped to hold therein the compression insert in the insertion shape. The insert delivery device includes a plunger with a shaft extending therefrom. The plunger integrates with the barrel such that the shaft extends through the conduit. The plunger is moveable between a pre-delivery position that allows loading of the compression insert in the insertion shape into the insert receiver and a delivery position whereby the shaft pushes the compression insert from the insert receiver.

It is therefore an object of the present invention to provide an orthopedic fixation system configured to continuously apply a force to fixate bone, bones, or bone pieces without use of a shape changing orthopedic implant.

It is another object of the present invention to provide an orthopedic fixation system with an orthopedic implant configured to receive therein a compression insert in an insertion shape, whereby the compression insert, due to an attempted transition thereof from the insertion shape to a natural shape, delivers energy stored therein to the orthopedic implant such that the orthopedic implant affixes bone, bones, or bone pieces.

Still other objects, features, and advantages of the present invention will become evident to those of ordinary skill in the art in light of the following. Also, it should be understood that the scope of this invention is intended to be broad, and any combination of any subset of the features, elements, or steps described herein is part of the intended scope of the invention.

DETAILED DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. Figures are not necessarily to scale, and some features may be exaggerated to show details of particular components or steps.

Figure 1:
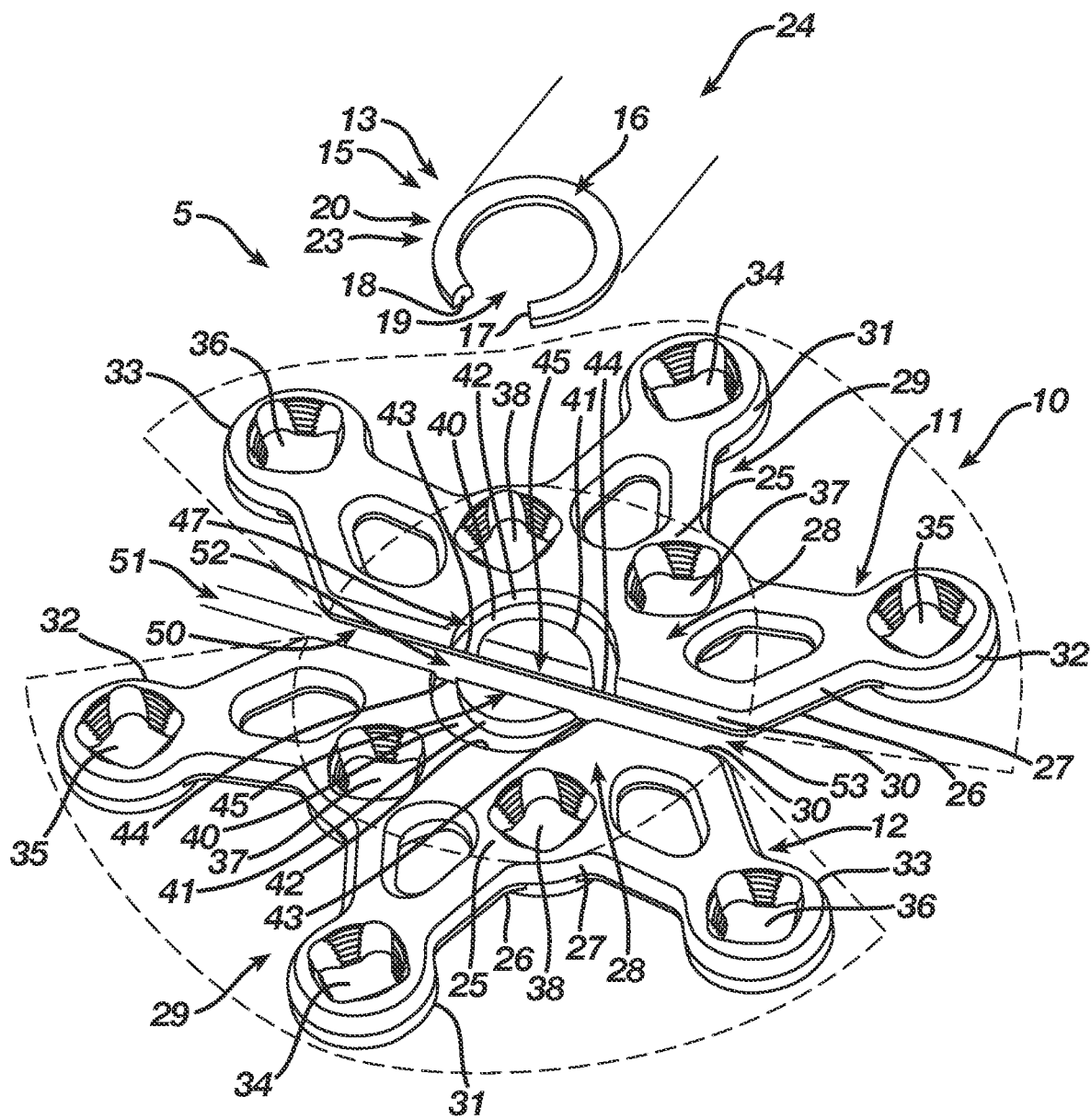
FIG. 1 is a top isometric view illustrating an orthopedic fixation system with a compression insert according to a first embodiment in an insertion shape disengaged from an orthopedic implant according to a first embodiment.

FIG. 1 illustrates an orthopedic fixation system 5 engageable with bone, bones, or bone pieces in order to affix the bone, bones, or bone pieces and promote a healing thereof. The orthopedic fixation system 5 includes an orthopedic implant 10 according to a first embodiment engageable with the bone, bones, or bone pieces across a fixation zone thereof. The orthopedic implant 10 includes a first plate 11 engageable with the bone, bones, or bone pieces at a first side of the fixation zone and a second plate 12 engageable with the bone, bones, or bone pieces at a second side of the fixation zone. The first plate 11 and the second plate 12, upon engagement with the bone, bones, or bone pieces, reside in opposed relationship atop the bone, bones, or bone pieces across the fixation zone. The orthopedic fixation system 5 further includes a compression insert 13 according to a first embodiment engageable with the orthopedic implant 10. More particularly, the compression insert 13 engages with the first plate 11 and the second plate 12 across the fixation zone of the bone, bones, or bone pieces thereby securing the first plate 11 with the second plate 12 such that the first plate 11 and the second plate 12 affix the bone, bones, or bone pieces.

Figure 2A:
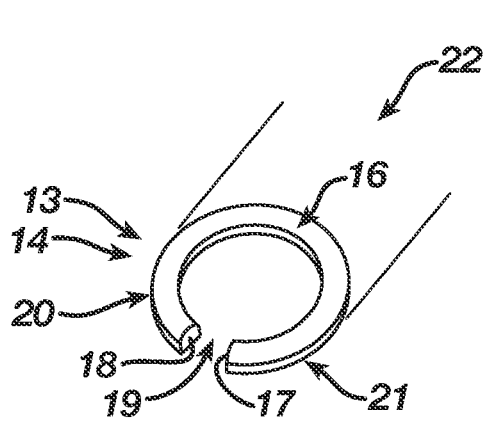
FIG. 2A is a top isometric view illustrating the compression insert according to the first embodiment in a natural shape.
Figure 2B:
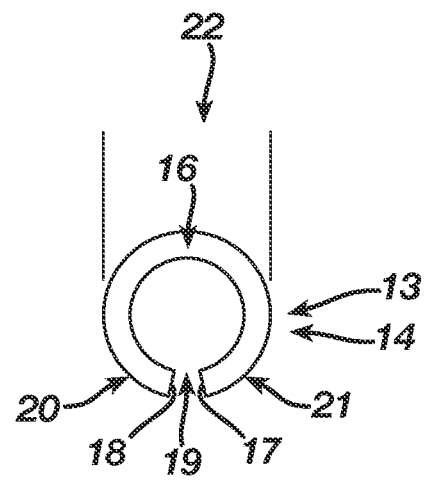
FIG. 2B is a top view illustrating the compression insert according to the first embodiment in the natural shape.
Figure 3A:
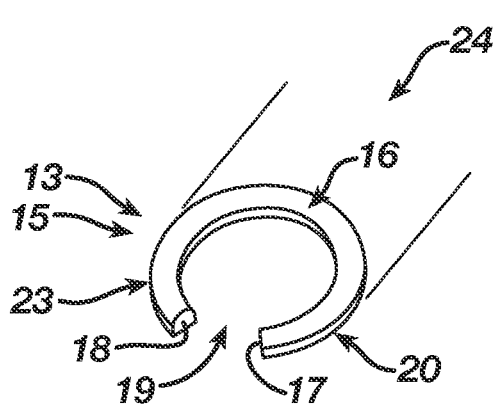
FIG. 3A is a top isometric view illustrating the compression insert according to the first embodiment in the insertion shape.
Figure 3B:
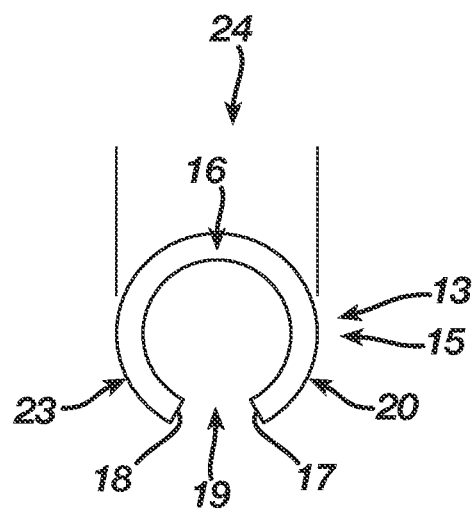
FIG. 3B is a top view illustrating the compression insert according to the first embodiment in the insertion shape.

FIGS. 2A-2B illustrate the compression insert 13 according to the first embodiment in a natural shape 14, whereas FIGS. 3A-3B illustrate the compression insert 13 in the insertion shape 15. The compression insert 13 in the first embodiment may be manufactured from a shape memory material with superelastic or temperature dependent properties (e.g., Nitinol) such that the compression insert 13 transitions between the natural shape 14 and the insertion shape 15. The compression insert 13 when deformed from the natural shape 14 to the insertion shape 15 stores energy deliverable to the orthopedic implant 10. In accordance with its manufacture from shape memory material, the compression insert 13 begins in the natural shape 14, is transitionable to the insertion shape 15, and, once engaged with the orthopedic implant 10, attempts to transition from the insertion shape 15 to the natural shape 14 whereby the compression insert 13 delivers the energy stored therein to the orthopedic implant 10. As will be more fully described herein, an engagement of the compression insert 13 of the first embodiment with the orthopedic implant 10 of the first embodiment, and, more particularly, with the first plate 11 and the second plate 12 thereof across a fixation zone of bone, bones, or bone pieces, followed by an attempted transition of the compression insert 13 from the insertion shape 15 to the natural shape 14 facilitates the orthopedic implant 10 continuously compressing bone, bones, or bone pieces to promote fusion thereof.

The compression insert 13 includes a transition section 16 and terminates in a first end 17 and a second end 18 defining a gap 19 therebetween. The transition section 16 in the first embodiment resides opposite from the first end 17 and the second end 18 and the gap 19 defined therebetween such that the transition section 16, based upon the compression insert 13 including the gap 19, facilitates transition of the compression insert 13 between the natural shape 14 and the insertion shape 15. The compression insert 13 in the first embodiment is a ring 20 split to create the first end 17 and the second end 18 and the gap 19 therebetween. The regular inherent shape of the compression insert 13, as illustrated in FIGS. 2A-2B, is the natural shape 14 where the transition section 16, based upon the compression insert 13 including the gap 19, locates the compression insert 13 in the natural shape 14, which consists of a closed position 21 whereby the compression insert 13 includes a first width 22, which, in the first embodiment, is a first diameter 22. Nevertheless, as illustrated in FIGS. 3A-3B, the compression insert 13 is deformable under the action of superelasticity or temperature dependent shape memory to the insertion shape 15 where the transition section 16, based upon the compression insert 13 including the gap 19, deforms to store energy while also moving the compression insert 13 from the natural shape 14 to the insertion shape 15, which consists of an open position 23 whereby the compression insert 13 includes a second width 24, which, in the first embodiment, is a second diameter 24, that is greater than the first width or diameter 22. Although the compression insert 13 in the first embodiment includes the ring 20 split to form the gap 19, one of ordinary skill in the art will recognize alternative shapes for the compression insert 13, such as, for example, polygons, provided a line segment of the polygon is split to form a gap. Since the insertion shape 15 is not the regular inherent shape of the compression insert 13, the orthopedic implant 10, when coupled with the compression insert 13, typically is mechanically constrained using an implant retainer whereby the implant retainer holds the orthopedic implant 10 such that the compression insert 13 is prevented from returning to the natural shape 14 thereof. Alternatively, the compression insert 13 may be mechanically constrained using an insert retainer that maintains the compression insert 13 in the insertion form 15 until an engagement of the compression insert 13 with the orthopedic implant 10 and a release of the compression insert 13 from the insert retainer.

Referring to FIGS. 1 and 4A-5C, the first plate 11 exhibits a three-dimensional form whereby the first plate 11 between an upper surface 25 and a lower surface 26 includes a thickness 27 sufficient for the first plate 11 to resist deformation after implantation. The upper surface 25 is substantially planar to present the first plate 11 with a lowest possible profile, whereas the lower surface 26 is substantially planar in order for the first plate 11 at the lower surface 26 to seat flush atop bone, bones, or bone pieces. The lower surface 26 may include relief cuts that limit contact of the lower surface 26 with the bone, bones, or bone pieces. The first plate 11 in the first embodiment is manufactured from any biocompatible metal or metal alloy, such as, for example, titanium, nitinol, stainless steel, titanium alloy, and cobalt chrome alloy.

The first plate 11 includes a body section 28 that provides structural rigidity to the first plate 11 and an anchoring section 29 that provides for a securing of the first plate 11 with bone, bones, or bone pieces. The body section 28 and thus the first plate 11, due to the thickness 27 of the first plate 11, includes a front face 30, which preferably is substantially planar in order to permit the first plate 11 to reside adjacent the second plate 12. The anchoring section 29 of the first plate 11 according to the first embodiment includes at least one anchoring member 31 projecting from the body section 28 such that the anchoring member 31 is located remote from the front face 30. The anchoring member 31 facilitates a securing of the first plate 11 with bone, bones, or bone pieces, and, in accordance therewith, the anchoring member 31 includes an opening 34 therethrough configured to receive a suitable fixation device, such as a biocompatible locking, non-locking, or self-tapping bone screw, that secures the anchoring member 31 and thus the first plate 11 with bone, bones, or bone pieces. Although the anchoring member 31 adequately secures the first plate 11 with bone, bones, or bone pieces, the anchoring section 29 of the first plate 11 in the first embodiment includes an anchoring member 32 with an opening 35 therethrough and an anchoring member 33 with an opening 36 therethrough projecting from the body section 28 such that the anchoring members 32 and 33 are located remote from the front face 30. The anchoring members 32 and 33 in providing additional connection points for the first plate 11 with bone, bones, or bone pieces improve a securing of the first plate 11 with the bone, bones, or bone pieces. The anchoring members 31-33 in the first embodiment are discrete elements spaced along the body section 28 about the front face 30 thereof whereby a securing of the first plate 11 with bone, bones, or bone pieces distributes the fixation devices inserted through the anchoring members 31-33 via their respective openings 34-36 over a length of the bone, bones, or bone pieces, thereby enhancing the securing of the first plate 11 with the bone, bones, or bone pieces. The first plate 11 in the body section 28 may include openings 37 and 38 therethrough configured to receive a suitable fixation device in order to provide additional connection points for the first plate 11 with bone, bones, or bone pieces that improve a securing of the first plate 11 with the bone, bones, or bone pieces. The body section 28 and the anchoring section 29 may be contoured to match patient anatomy.

The first plate 11 in the body section 28 thereof defines an insert slot 40 including an inner surface 41 and an outer surface 42. The insert slot 40 is configured to receive therein a portion of the compression insert 13 such that the compression insert 13 engages with the first plate 11. The insert slot 40 traverses the body section 28 from a first opening 43 to a second opening 44. The first opening 43 and the second opening 44 are located at the front face 30 of the first plate 11 in order to permit the compression insert 13 to extend from the first plate 11 for engagement with the second plate 12. The insert slot 40 between the inner and outer surfaces 41 and 42 includes dimensions sufficient for the insert slot 40 to receive the compression insert 13 therein. The insert slot 40 further includes dimensions, particularly with respect to a length thereof, substantially equal to a length of a portion of the compression insert 13, which, in the first embodiment, comprises a bi-section of the compression insert 13 including the gap 19 taken at the first width 22 of the compression insert 13 when the compression insert 13 resides in the natural shape 14. The insert slot 40, accordingly, due to dimensions thereof being substantially equal to the bi-sectional length of the compression insert 13 in the natural shape 14, includes a width 45 along the front face 30 of the first plate 11 substantially equal to the first width 22 of the compression insert 13 produced when the compression insert 13 resides in the natural shape 14. The width 45 of the insert slot 40 along the front face 30 of the first plate 11 is substantially equal to the first width 22 of the compression insert 13 in the natural shape 14 in order for the compression insert 13 to engage with the body section 28 at the inner surface 41 of the insert slot 40, thereby ensuring the compression insert 13 remains within the first plate 11, while further permitting the compression insert 13 to extend from the insert slot 40 for engagement with the second plate 12.

The second plate 12 is substantially, completely similar in design and operation relative to the first plate 11 such that, for the sake of brevity, only differences therebetween will be described herein. Moreover, one of ordinary skill in the art will recognize that like parts of the second plate 12 labeled with like numerals of the first plate 11 incorporate a design and function as previously set forth in the detailed description of the first plate 11. During use of the orthopedic implant 10, the second plate 12 is employed substantially the same as the first plate 11, except the second plate 12 is reversed relative to the first plate 11. Illustratively, when the first plate 11 engages with bone, bones, or bone pieces at a first side of a fixation zone with the front face 30 thereof residing adjacent the fixation zone, the second plate 12 is reversed relative to the first plate 11 such that the second plate 12 engages with the bone, bones, or bone pieces at a second side of the fixation zone with the front face 30 thereof residing adjacent the fixation zone. In accordance therewith, the second plate 12 mirrors the first plate 11 whereby the front face 30 of the second plate 12 aligns across the fixation zone with the front face 30 of the first plate 11.

Figure 4A:
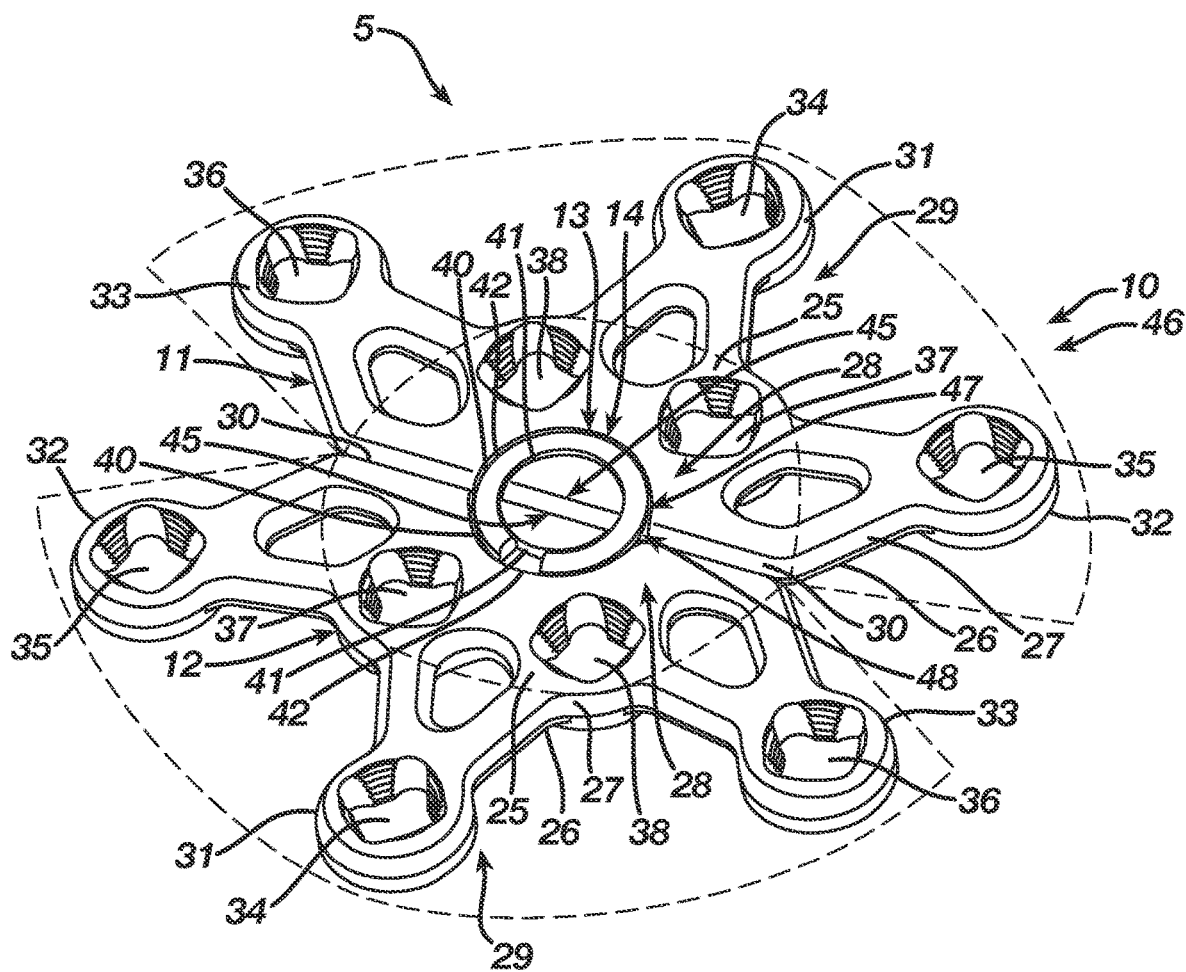
FIG. 4A is a top isometric view illustrating the orthopedic fixation system with the compression insert according to the first embodiment in the natural shape engaged with the orthopedic implant according to the first embodiment.
Figure 4B:
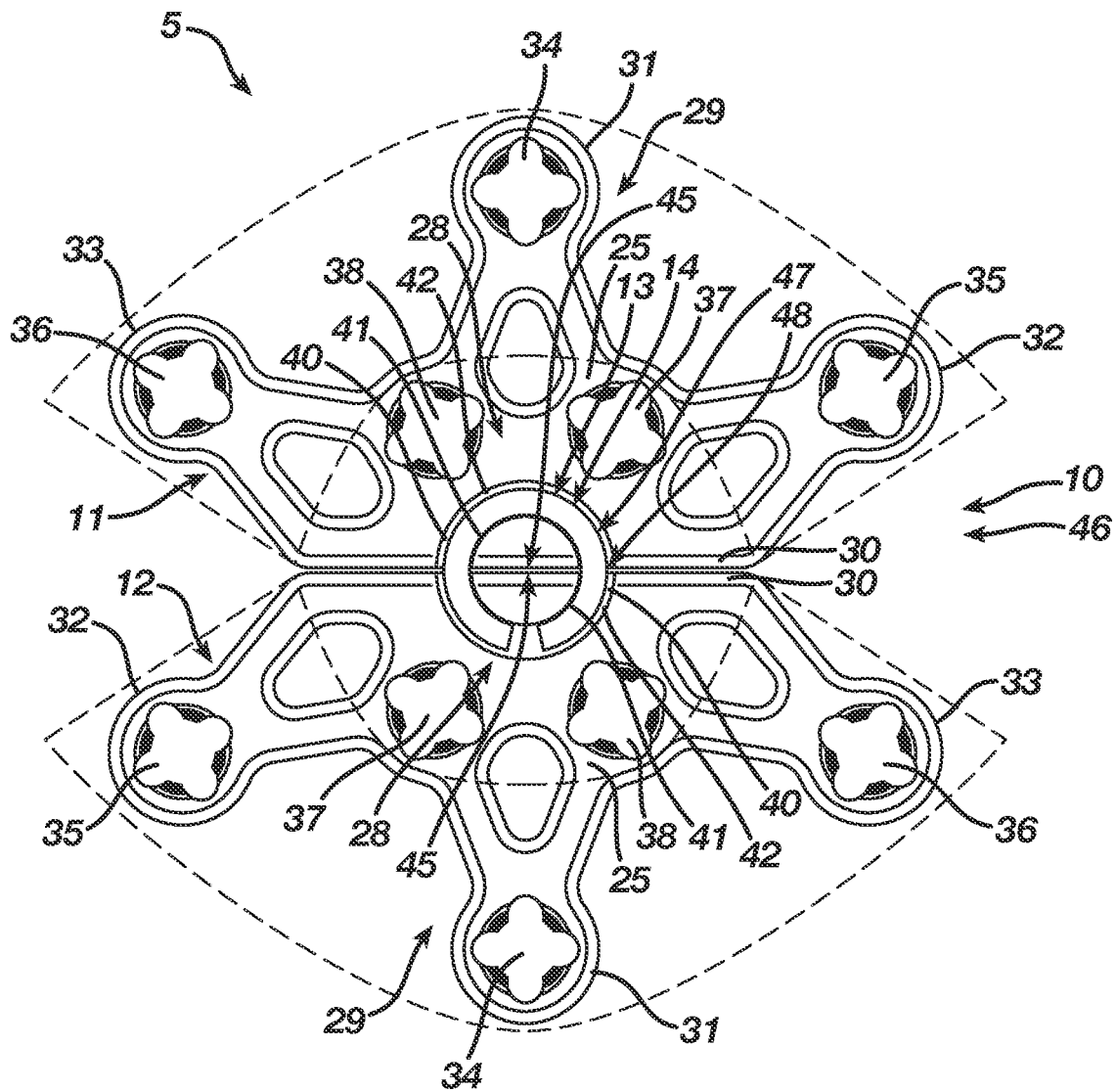
FIG. 4B is a top view illustrating the orthopedic fixation system with the compression insert according to the first embodiment in the natural shape engaged with the orthopedic implant according to the first embodiment.
Figure 4C:
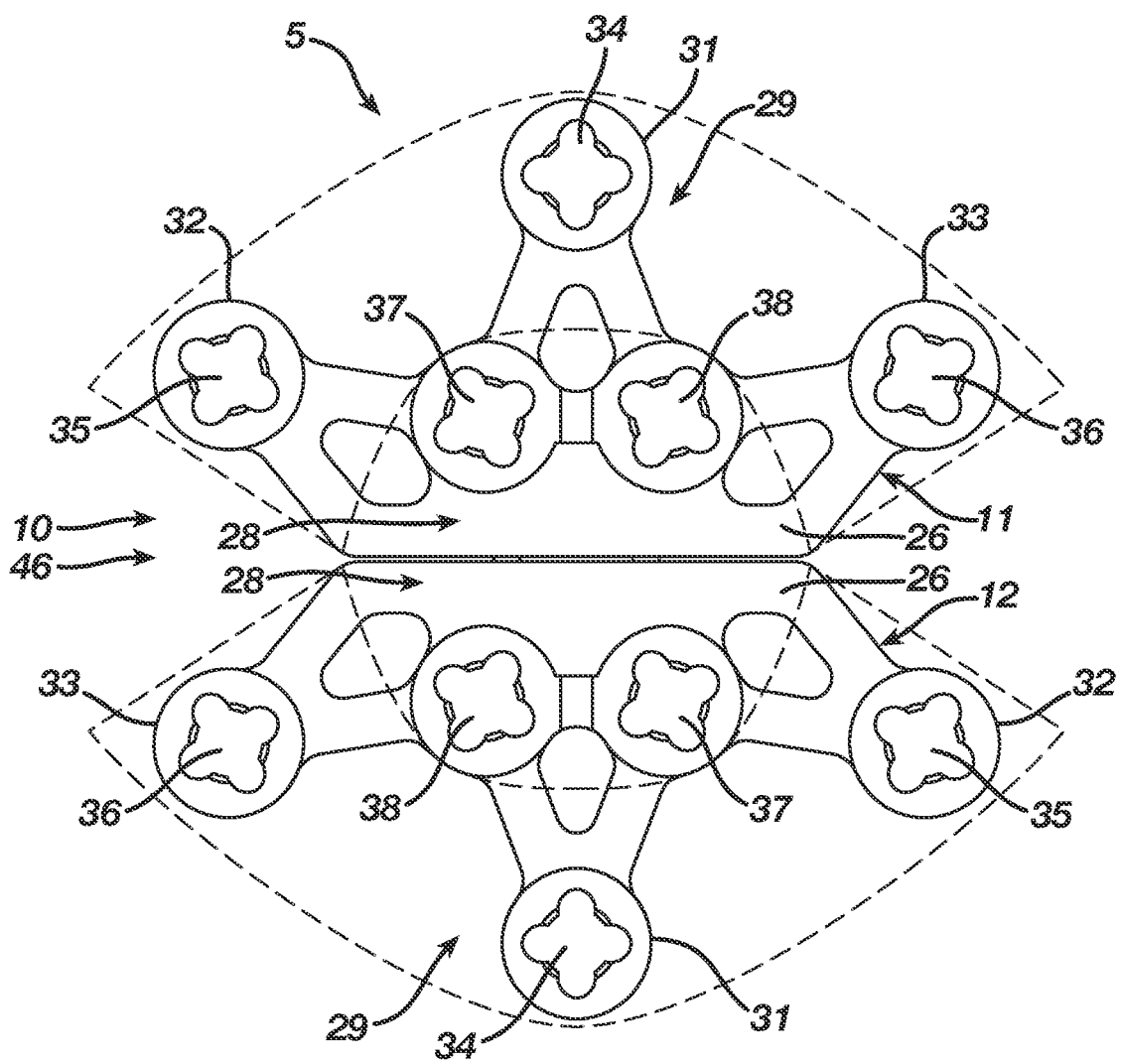
FIG. 4C is a bottom view illustrating the orthopedic fixation system with the compression insert according to the first embodiment in the natural shape engaged with the orthopedic implant according to the first embodiment.

FIGS. 4A-4C illustrate the orthopedic implant 10 according to the first embodiment residing in a natural position 46 configured for receipt therein of the compression insert 13 when transitioned to the natural shape 14. The orthopedic implant 10 in the natural position 46 includes the first plate 11 at the front face 30 thereof facing the second plate 12 at the front face 30 thereof such that the front faces 30 are aligned while being located directly adjacent. When the first plate 11 and the second plate 12 are aligned with the front faces 30 thereof directly adjacent, the insert slot 40 of the first plate 11 at the first opening 43 and the second opening 44 aligns with the insert slot 40 of the second plate 12 at the second opening 44 and the first opening 43. The insert slots of the first plate 11 and the second plate 12, when the orthopedic implant 10 resides in the natural position 46, align to provide the orthopedic implant 10 with an insert retaining pathway 47, which, in the first embodiment of the orthopedic implant 10, comprises a continuous pathway traversing the first plate 11 and the second plate 12, and, in particular, the body sections 28 of the first plate 11 and the second plate 12. The insert retaining pathway 47, accordingly, due to the widths 45 of the insert slots 40 being substantially equal to the first width 22 of the compression insert 13 in combination with the first plate 11 and the second plate 12 being aligned such that the front faces 30 thereof reside directly adjacent, includes a first width 48 taken along the front faces of the first plate 11 and the second plate 12 that is substantially equal to the first width 22 of the compression insert 13 produced when the compression insert 13 resides in the natural shape 14. The first width 48 of the insert retaining pathway 47 along the front faces 30 of the first plate 11 and the second plate 12 is substantially equal to the first width 22 of the compression insert 13 in the natural shape 14 in order for the insert retaining pathway 47 to hold therein the compression insert 13 engaged with the body sections 28 of the first plate 11 and the second plate 12 at the inner surfaces 41 of the insert slots 40, thereby ensuring the compression insert 13 remains within the first plate 11 and the second plate 12 and thus the orthopedic implant 10.

Figure 5A:
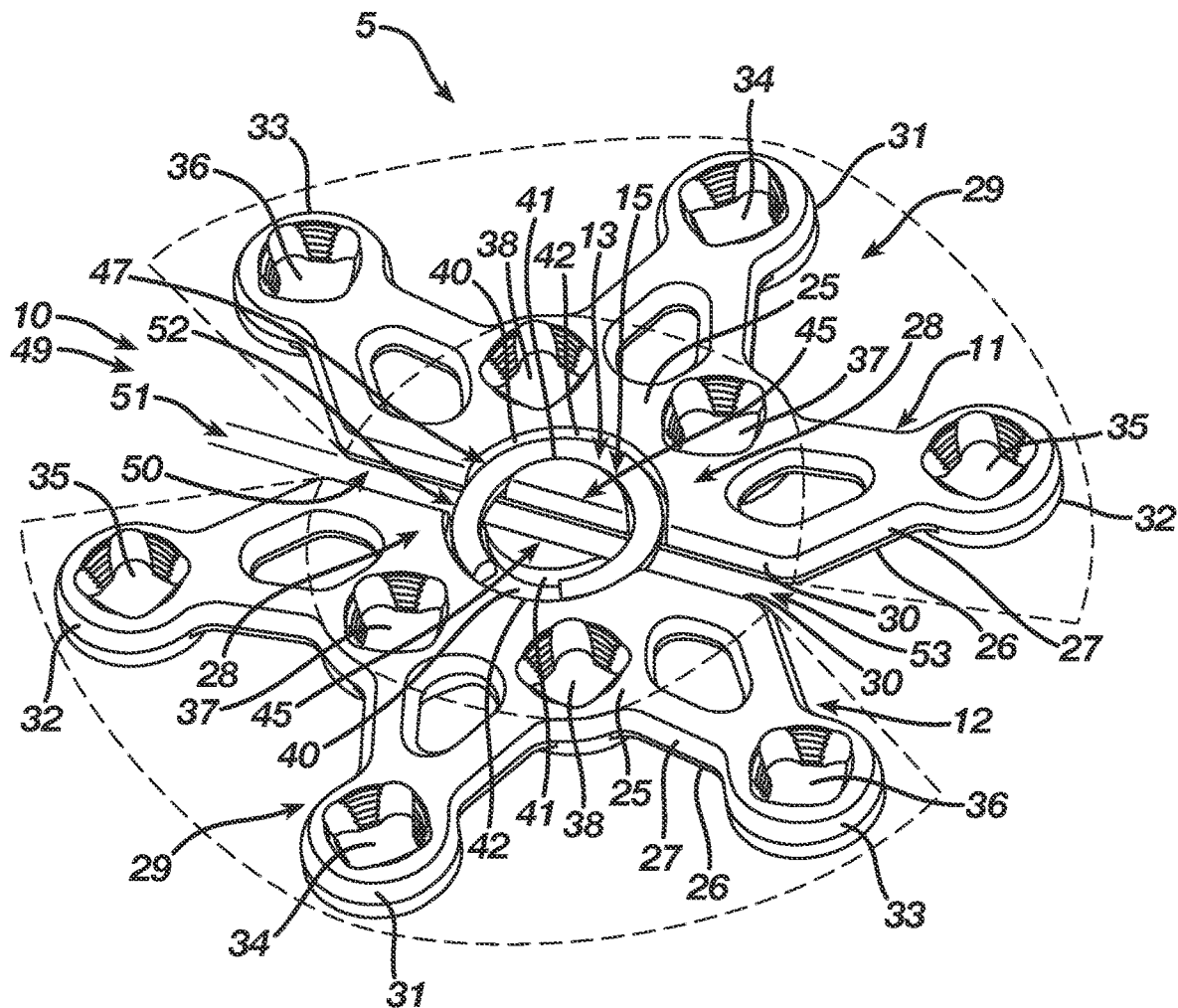
FIG. 5A is a top isometric view illustrating the orthopedic fixation system with the compression insert according to the first embodiment in the insertion shape engaged with the orthopedic implant according to the first embodiment.
Figure 5B:
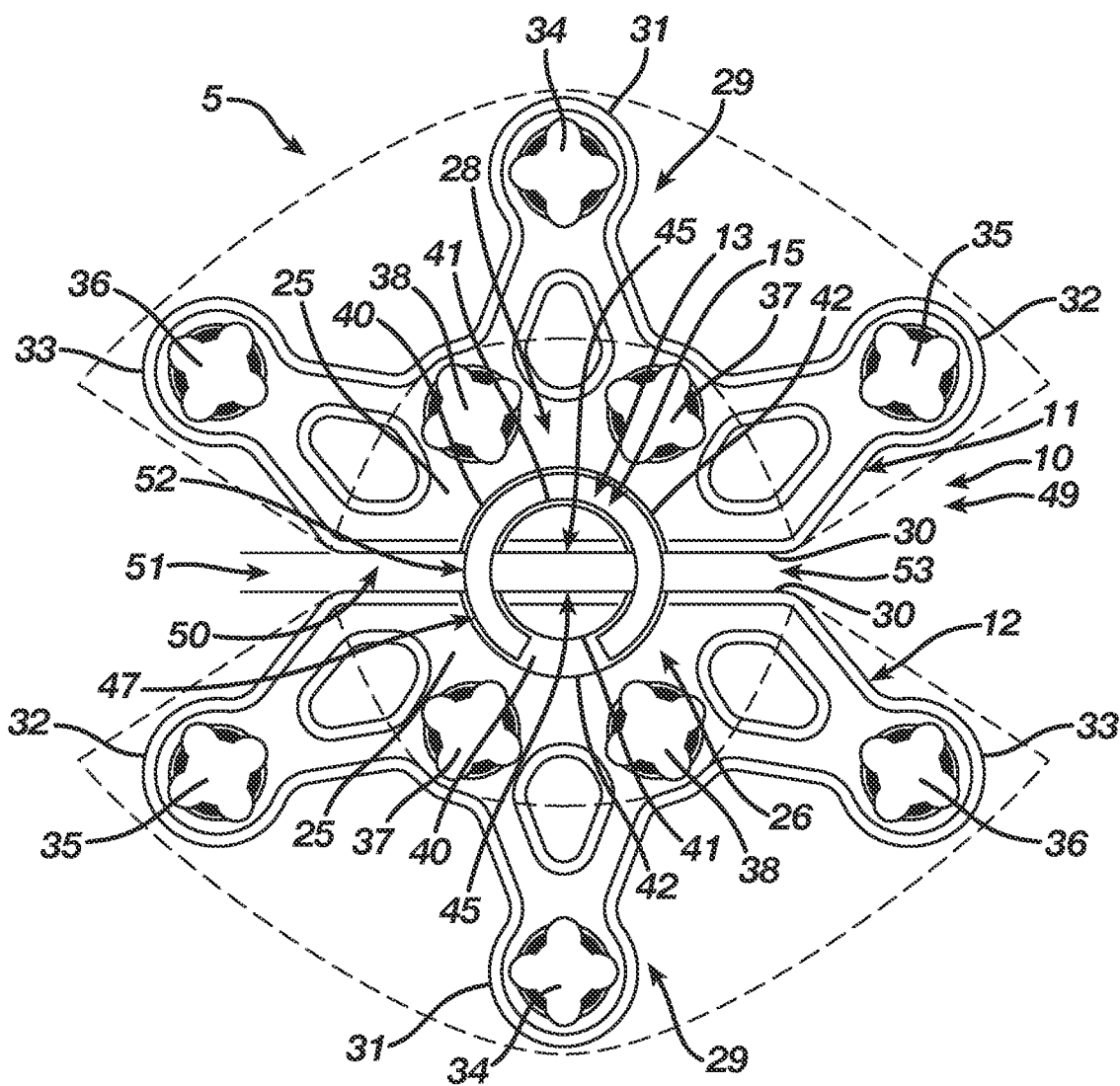
FIG. 5B is a top view illustrating the orthopedic fixation system with the compression insert according to the first embodiment in the insertion shape engaged with the orthopedic implant according to the first embodiment.
Figure 5C:
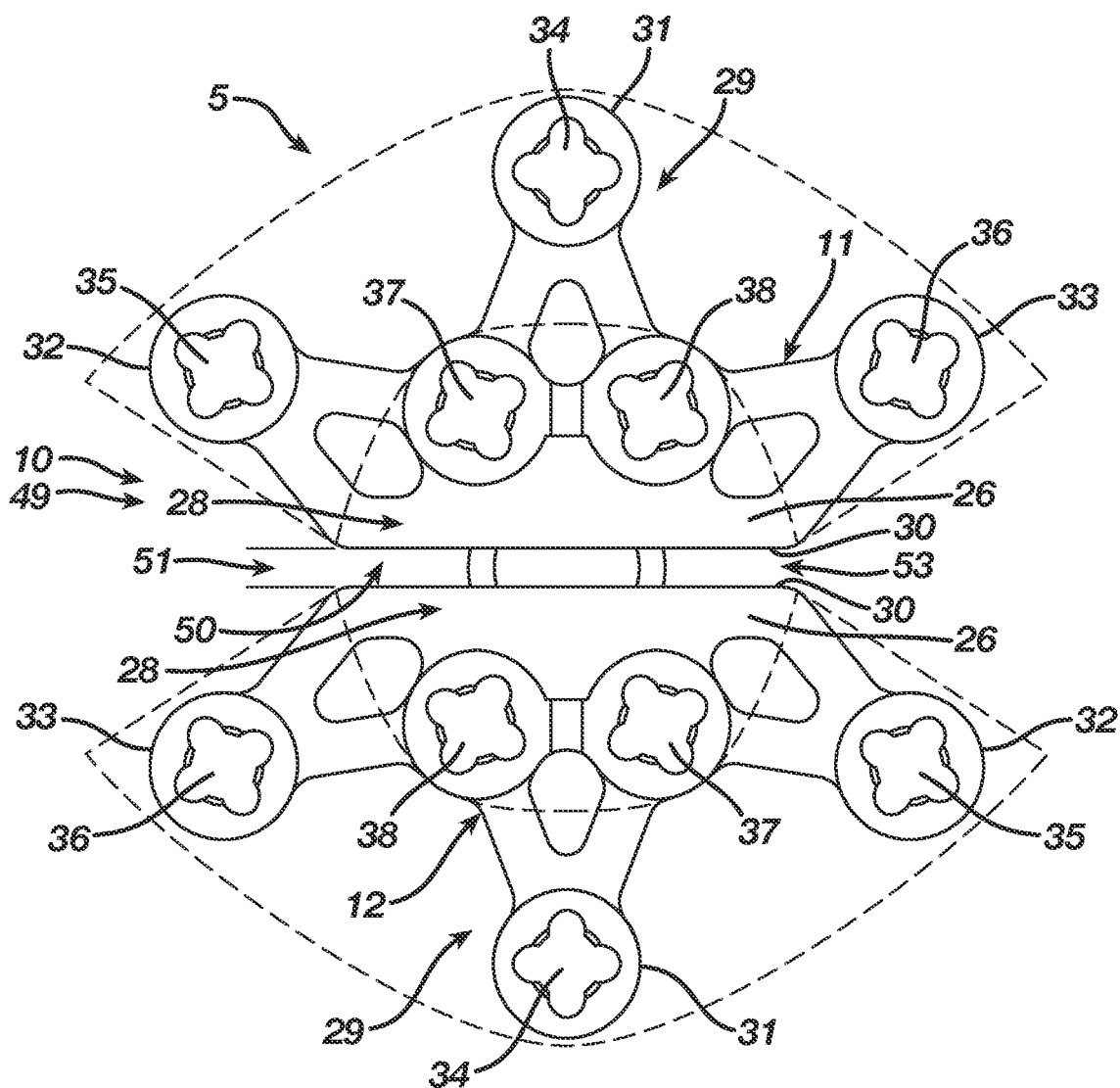
FIG. 5C is a bottom view illustrating the orthopedic fixation system with the compression insert according to the first embodiment in the insertion shape engaged with the orthopedic implant according to the first embodiment.

FIGS. 5A-5C illustrate the orthopedic implant 10 according to the first embodiment residing in an insertion position 49 configured for receipt therein of the compression insert 13 when deformed into the insertion shape 15. The orthopedic implant 10 in the insertion position 49 includes the first plate 11 at the front face 30 thereof facing the second plate 12 at the front face 30 thereof such that the front faces 30 are aligned while being spaced apart to produce an expansion 50 having a width 51. When the first plate 11 and the second plate 12 are aligned with the front faces 30 thereof spaced apart to produce the expansion 50, the insert slot 40 of the first plate 11 at the first opening 43 and the second opening 44 aligns with the insert slot 40 of the second plate 12 at the second opening 44 and the first opening 43. The insert slots 40 of the first plate 11 and the second plate 12, when the orthopedic implant 10 resides in the insertion position 49, align to provide the orthopedic implant 10 with the insert retaining pathway 47, which, in the first embodiment of the orthopedic implant 10, traverses the body sections 28 of the first plate 11 and the second plate 12, including the expansion 50. In accordance therewith, the first plate 11 and the second plate 12, on account of their being spaced apart in the insertion position 49 of the orthopedic implant 10 to produce the expansion 50 having the width 51, provide the insert retaining pathway 47 with a configuration that facilitates an insertion of the compression insert 13 into the insert retaining pathway 47 when the compression insert 13 resides in the insertion shape 15. More particularly, the expansion 50 between the first plate 11 and the second plate 12 expands the insert retaining pathway 47 to a size sufficient for receipt therein of the compression insert 13 in the insertion shape 15. The insert retaining pathway 47, therefore, due to the widths 45 of the insert slots 40 being substantially equal to the first width 22 of the compression insert 13 in combination with the first plate 11 and the second plate 12 being aligned such that the front faces 30 thereof are spaced apart to produce the expansion 50 having the width 51, includes through an expansion thereof a second width 52 taken along the front faces 30 of the first plate 11 and the second plate 12 at a centerline 53 of the expansion 50 that is substantially equal to the second width 24 of the compression insert 13 produced when the compression insert 13 resides in the insertion shape 15. In the first embodiment, the width 51 of the expansion 50 is selected to expand the insert slot 40 of the first plate 11 away from the insert slot 40 of the second plate 12 a distance that enlarges the insert retaining pathway 47 to the second width 52 that substantially equals the second width 24 of the compression insert 13 in the insertion shape 15. The second width 52 of the insert retaining pathway 47 along the front faces 30 of the first plate 11 and the second plate 12 at the centerline 53 of the expansion 50 is substantially equal to the second width 24 of the compression insert 13 in the insertion shape 15 in order for the insert retaining pathway 47 to receive therein the compression insert 13 in the insertion shape 15.

When utilizing the orthopedic fixation system 5 to affix bone, bones, or bone pieces and promote a healing thereof, the orthopedic implant 10 while located in the insertion position 49 engages with the bone, bones, or bone pieces across a fixation zone thereof. More particularly, the first plate 11 engages with the bone, bones, or bone pieces at a first side of the fixation zone, whereas the second plate 12 engages with the bone, bones, or bone pieces at a second side of the fixation zone. The first plate 11 and the second plate 12, upon engagement with the bone, bones, or bone pieces, are aligned at their front faces 30 while being spaced apart across the fixation zone by the expansion 50 having the width 51 such that the orthopedic implant 10 via the first plate 11 and the second plate 12 and the expansion 50 thereof includes the insert retaining pathway 47 having the second width 52 that is substantially equal to the second width 24 of the compression insert 13 produced when the compression insert 13 resides in the insertion shape 15. The compression insert 13, which has been deformed to the insertion shape 15 whereby the compression insert 13 stores energy, inserts into the insert retaining pathway 47 on account of the insert retaining pathway 47 including the second width 52. Upon insertion into the insert retaining pathway 47 including a release of any mechanical constraint, the compression insert 13 attempts to transition from the insertion shape 15 to the natural shape 14 such that the compression insert 13 engages with the body sections 28 of the first plate 11 and the second plate 12 at the inner surfaces 41 of the insert slots 40, thereby ensuring the compression insert 13 remains within the first plate 11 and the second plate 12 and thus the orthopedic implant 10. Moreover, the compression insert 13, due to its attempted transition from the insertion shape 15 to the natural shape 14, delivers the energy stored therein to the first plate 11 and the second plate 12 and thus the orthopedic implant 10, resulting in the orthopedic implant 10 attempting to move from the insertion position 49, which includes the expansion 50, to the natural position 46. In accordance therewith, the orthopedic implant 10 continuously compresses the bone, bones, or bone pieces at the fixation zone thereof whereby the orthopedic fixation system 5 affixes the bone, bones, or bone pieces in order to promote a fusion and a healing thereof. One of ordinary skill in the art will recognize that the sizes of the first plate 11, the second plate 12, the insert slots 40, the expansion 50, and the compression insert 13 are dependent upon the anatomy requiring fixation including the size and configuration of the bone, bones, or bone pieces requiring fixation.

Figure 6A:
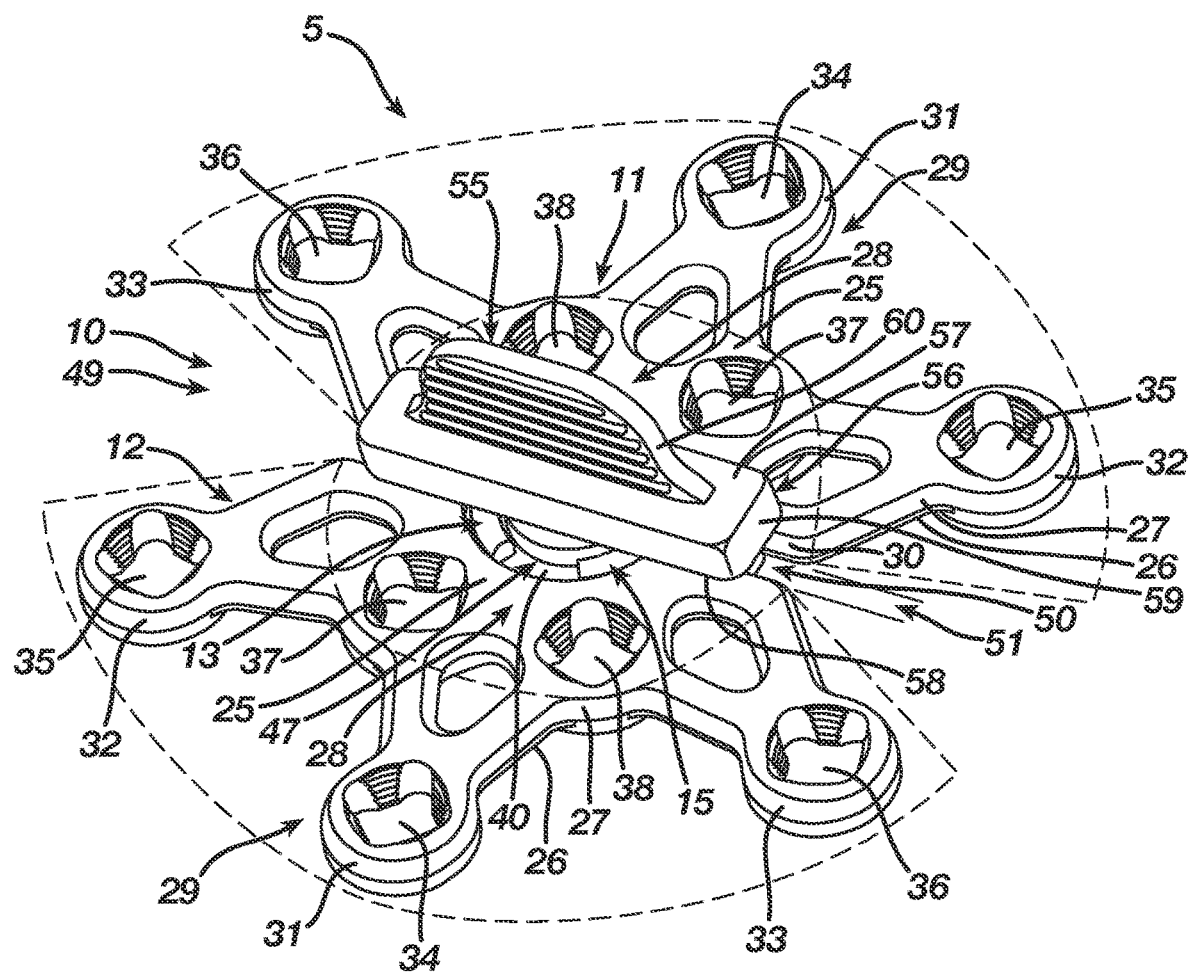
FIG. 6A is a top isometric view illustrating the orthopedic fixation system with an implant retainer according to a first embodiment and the compression insert according to the first embodiment in the insertion shape engaged with the orthopedic implant according to the first embodiment.
Figure 6B:
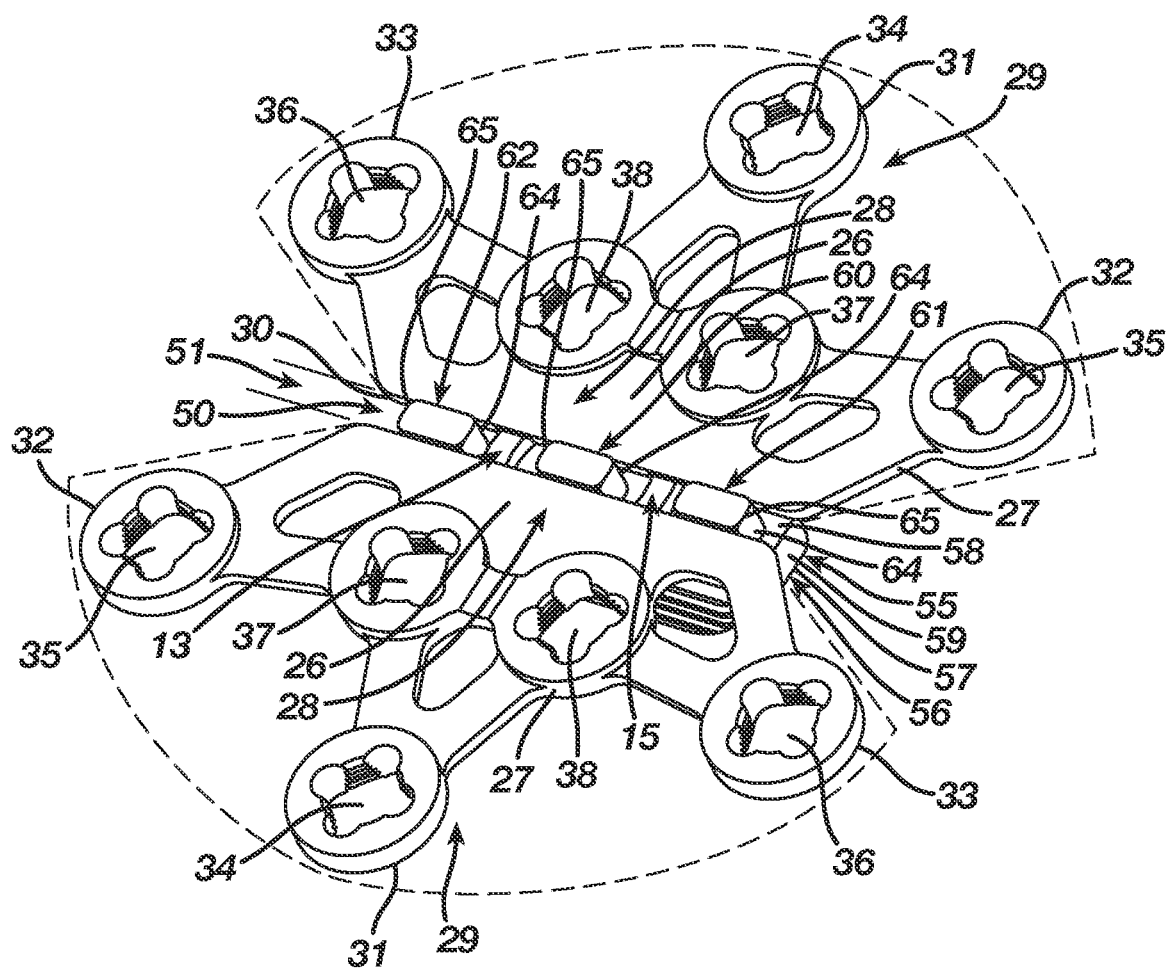
FIG. 6B is a bottom view illustrating the orthopedic fixation system with the implant retainer according to the first embodiment and the compression insert according to the first embodiment in the insertion shape engaged with the orthopedic implant according to the first embodiment.

The orthopedic fixation system 5 as illustrated in FIGS. 6A-6B includes an implant retainer 55 according to a first embodiment configured to hold the compression insert 13 in the insertion shape 15 within the orthopedic implant 10 while retaining the orthopedic implant 10 in the insertion position 49. The implant retainer 55 includes a body 56 that exhibits a three-dimensional form having a length, width, and height, and, in particular, an upper surface 57 and a lower surface 58 defining therebetween a thickness 59 that provides strength to the body 56. The lower surface 58 is substantially planar in order for the implant retainer 55 to seat flush atop the orthopedic implant 10. The implant retainer 55 includes a grip 60 extending from the upper surface 57 of the body 56 that facilitates grasping of the implant retainer 55. The implant retainer 55 includes at least a first block 61 projecting from the lower surface 58 of the body 56 and preferably a first block 61, a second block 62, and a third block 63 projecting from the lower surface 58 of the body 56. The first block 61 is located centrally on the body 56, whereas the second block 62 and the third block 63 are located along the body 56 in alignment with the first block 61 while being spaced apart therefrom such that the second block 62 and the third block 63 reside adjacent opposite ends of the body 56. The first block 61 is located centrally on the body 56 with the second block 62 and the third block 63 spaced apart therefrom in order for the first block 61 to engage the orthopedic fixation system 5 interior of the compression insert 13 while the second block 62 and the third block 63 engage the orthopedic fixation system 5 exterior of the compression insert 13. The first block 61, the second block 62, and the third block 63 each project from the lower surface 58 of the body 56 a distance 64 less than or equal to the thickness 27 of the first plate 11 and the second plate 12 whereby the implant retainer 55 does not interfere with the ability of the orthopedic implant 10 to sit flush atop bone, bones, or bone pieces. The first block 61, the second block 62, and the third block 63 each include a width 65 substantially equal to the width 51 of the expansion between the first plate 11 and the second plate 12 when the orthopedic implant 10 resides in the insertion position 49. In accordance therewith, the implant retainer 55, after orienting the orthopedic implant 10 in the insertion position 49 followed by a placement of the compression insert 13 in the insertion shape 15 within the insert retaining pathway 47, engages with the orthopedic implant 10. More particularly, the body 56 of the implant retainer 55 sits atop the orthopedic implant 10 while the first block 61 inserts into the expansion 50 interior of the compression insert 13 and the second block 62 and the third block 63 insert into the expansion 50 exterior of the compression insert 13. The implant retainer 55, via the first block 61, the second block 62, and the third block 63 and the widths 65 thereof, holds the first plate 11 spaced apart from the second plate 12 such that the implant retainer 55 prevents transition of the compression insert 13 from the insertion shape 15 to the natural shape 14 thereby maintaining the orthopedic implant 10 in the insertion position 49.

Figure 7A:
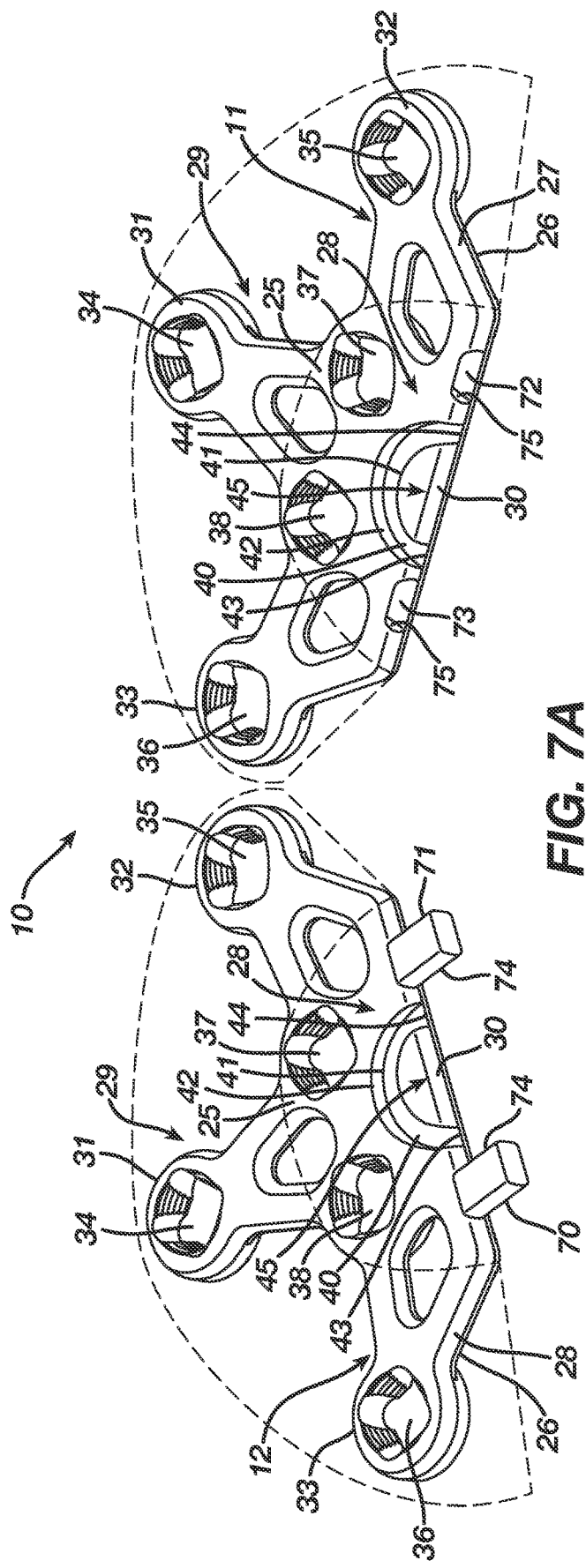
FIGS. 7A-7B are top isometric views illustrating the orthopedic implant according to the first embodiment including a load resistance feature.
Figure 7B:
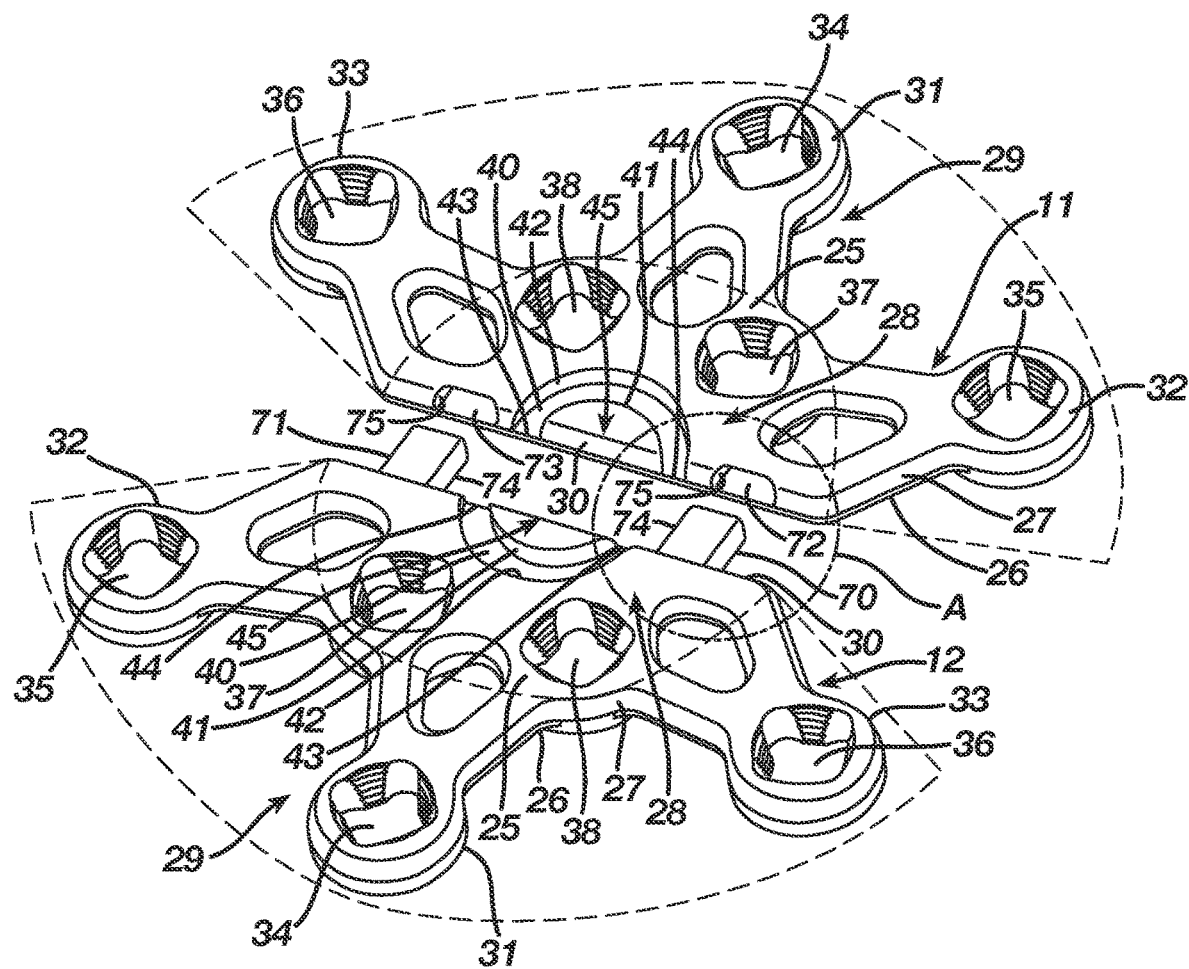
Figure 7C:
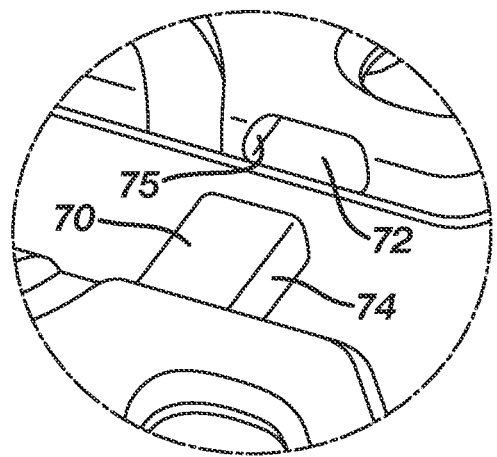
FIG. 7C is an enlarged top isometric view taken at circle A of FIG. 7B illustrating the load resistance feature of the orthopedic implant according to the first embodiment.

FIGS. 7A-7C illustrate the orthopedic implant 10 according to the first embodiment including a load resistance feature in the form of at least one stabilizer and a cavity configured complementary in shape with the stabilizer to receive the stabilizer therein. Although a single stabilizer and complementary cavity will provide load resistance to the orthopedic implant 10, the orthopedic implant 10 according to the first embodiment includes a first stabilizer 70 and a first cavity 72 and a second stabilizer 71 and a second cavity 73. The first stabilizer 70 and the second stabilizer 71 in the first embodiment are three-dimensional blocks, whereas the first cavity 72 and the second cavity 73 are cavities complementary in shape respectively with the first stabilizer 70 and the second stabilizer 71. In the first embodiment of the orthopedic implant 10, the second plate 12 includes the first stabilizer 70 projecting from the front face 30 adjacent but exterior to the first opening 43 of the insert slot 40, and the first plate 11 defines therein the first cavity 72 at the front face 30 adjacent but exterior to the second opening 44 of the insert slot 40. Similarly, the second plate 12 includes the second stabilizer 71 projecting from the front face 30 adjacent but exterior to the second opening 44 of the insert slot 40, and the first plate 11 defines therein the second cavity 73 at the front face 30 adjacent but exterior to the first opening 43 of the insert slot 40. The first stabilizer 70 and the first cavity 72 and the second stabilizer 71 and the second cavity 73 are correspondingly located respectively in the second plate 12 and the first plate 11 whereby, when the first plate 11 and the second plate 12 align at the front faces 30 thereof, the first stabilizer 70 aligns with the first cavity 72 and the second stabilizer 71 aligns with the second cavity 73. In accordance therewith, the first stabilizer 70 inserts into the first cavity 72 and the second stabilizer 71 inserts into the second cavity 73 during a use of the orthopedic fixation system 5 to affix bone, bones, or bone pieces. More particularly, after the first plate 11 engages with the bone, bones, or bone pieces at a first side of a fixation zone and the second plate 12 engages with the bone, bones, or bone pieces at a second side of the fixation zone, the first stabilizer 70 resides in engagement with the first cavity 72 and the second stabilizer 71 resides in engagement with the second cavity 73 such that the first plate 11 and the second plate 12 are coupled together exterior of their insert slots 40. This coupling provides the orthopedic implant 10 with load resistance on the basis the linking of the first plate 11 with the second plate 12 prevents loads experienced by the first plate 11 and the second plate 12, such as, for example, torsional or bending forces, from altering the relative positions of the first plate 11 and the second plate 12 on the bone, bones, or bone pieces. It should be understood that the first stabilizer 70 and the second stabilizer 71 each include a length 74 and the first cavity 72 and the second cavity 73 each include a depth 75, whereby, when the orthopedic implant 10 resides the insertion position 49, at least a segment of the first stabilizer 70 and a segment of the second stabilizer 71 insert respectively into the first cavity 72 and the second cavity 73, and, when the orthopedic implant 10 resides the natural position 46, the first stabilizer 70 and the second stabilizer 71 substantially, completely insert respectively into the first cavity 72 and the second cavity 73. One of ordinary skill in the art will recognize the first stabilizer 70 and the first cavity 72 and the second stabilizer 71 and the second cavity 73 may be reversed relative to the first plate 11 and the second plate 12.

Figure 7D:
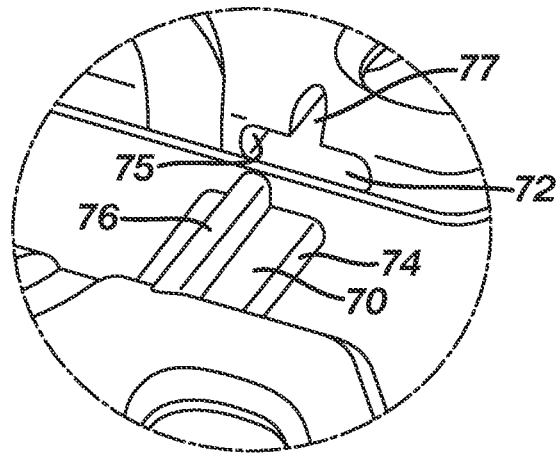
FIGS. 7D-7E are enlarged top isometric views illustrating alternative load resistance features of the orthopedic implant according to the first embodiment.

As illustrated in FIG. 7D, the first stabilizer 70 and/or the second stabilizer 71 in an alternative load resistance feature includes a wall 76 extending perpendicularly from the first stabilizer 70 and/or the second stabilizer 71. In order to accommodate the wall 76, the first cavity 72 and/or the second cavity 73 includes a slot 77 located perpendicular relative to the first cavity 72 and/or the second cavity 73. The wall 76 and corresponding slot 77 increase the surface area contact between the first stabilizer 70 and/or the second stabilizer 71 and the first cavity 72 and/or the second cavity 73.

Figure 7E:
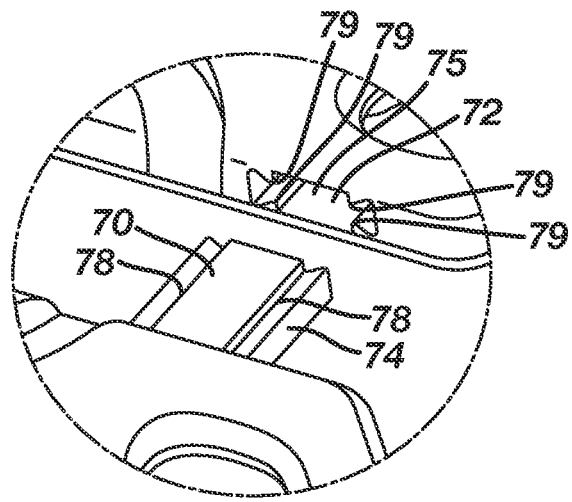
Figure 8A:
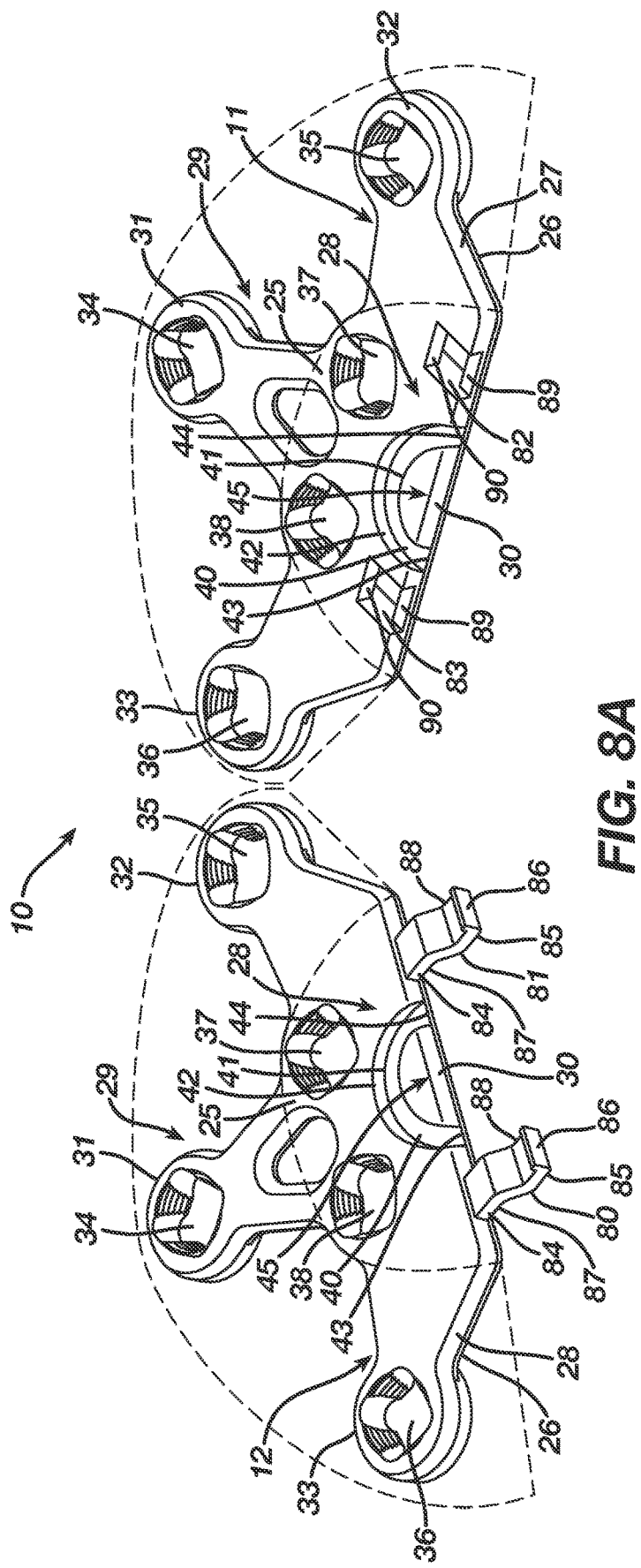
FIGS. 8A-8B are top isometric views illustrating the orthopedic implant according to the first embodiment including an alternative load resistance feature.
Figure 8B:
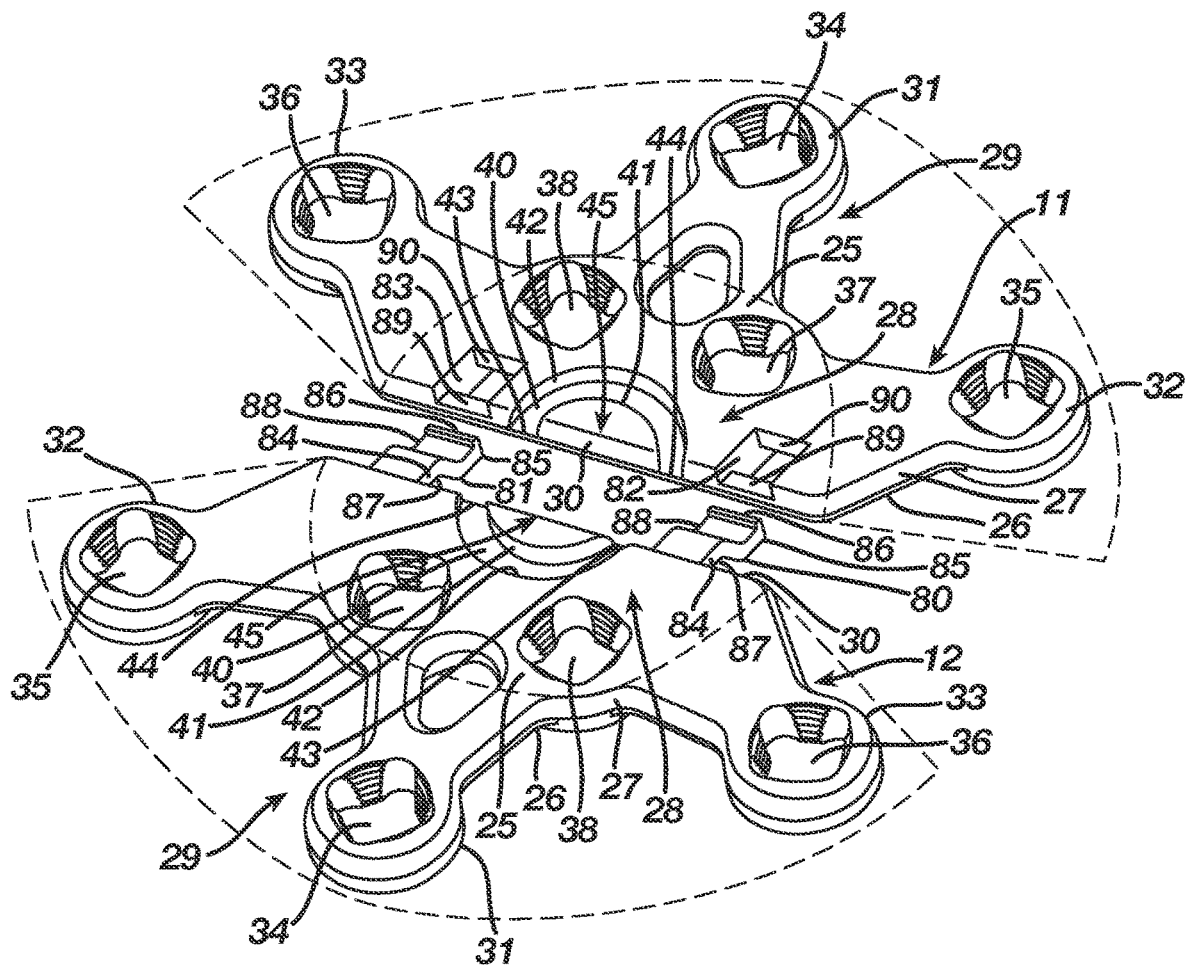
Figure 8C:
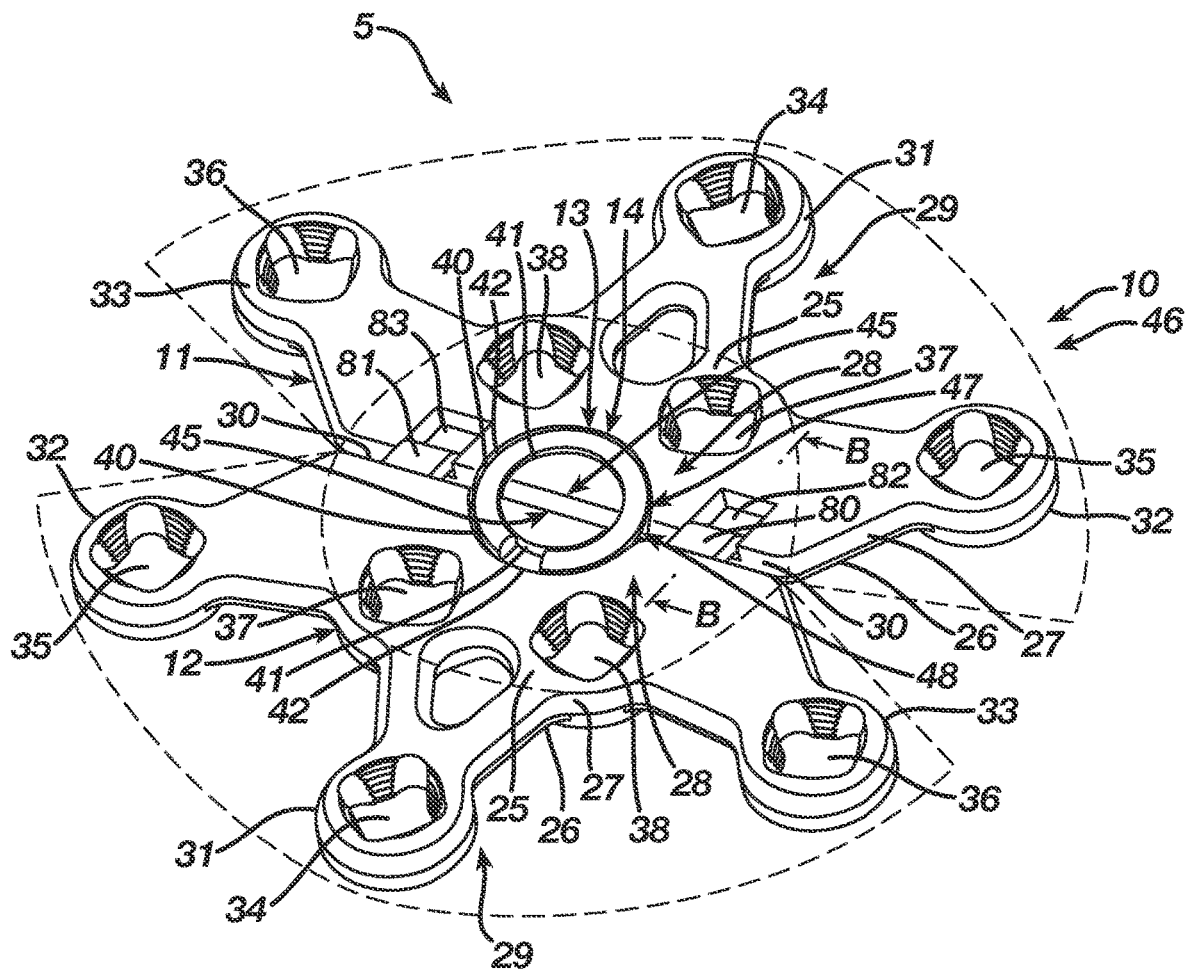
FIG. 8C is top isometric view illustrating the orthopedic implant according to the first embodiment including engagement of the alternative load resistance feature.
Figure 8D:
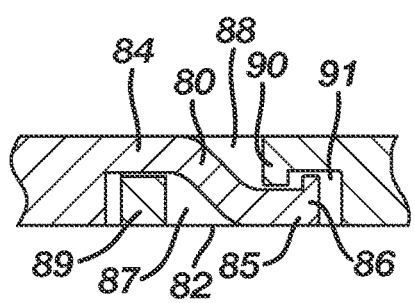
FIG. 8D is a cross-sectional view taken along lines B-B of FIG. 8C illustrating the orthopedic implant according to the first embodiment including engagement of the alternative load resistance feature.
Figure 9A:
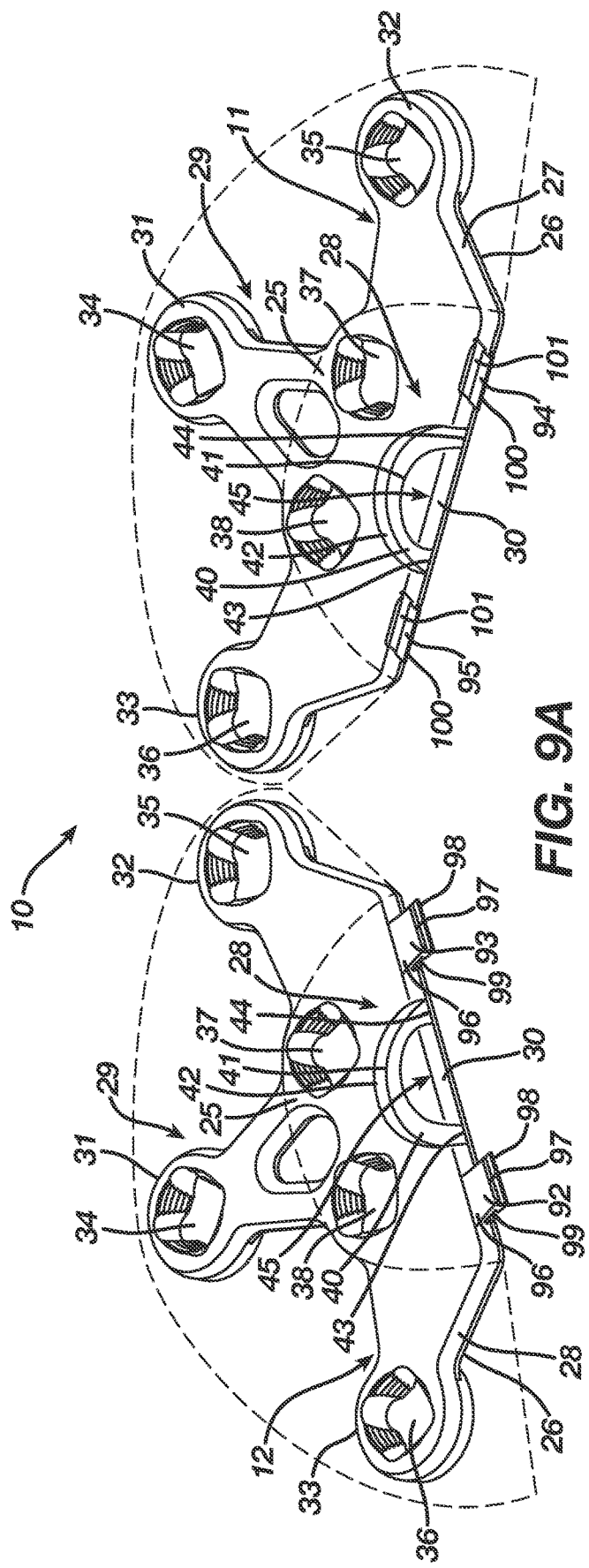
FIGS. 9A-9B are top isometric views illustrating the orthopedic implant according to the first embodiment including an alternative load resistance feature.
Figure 9B:
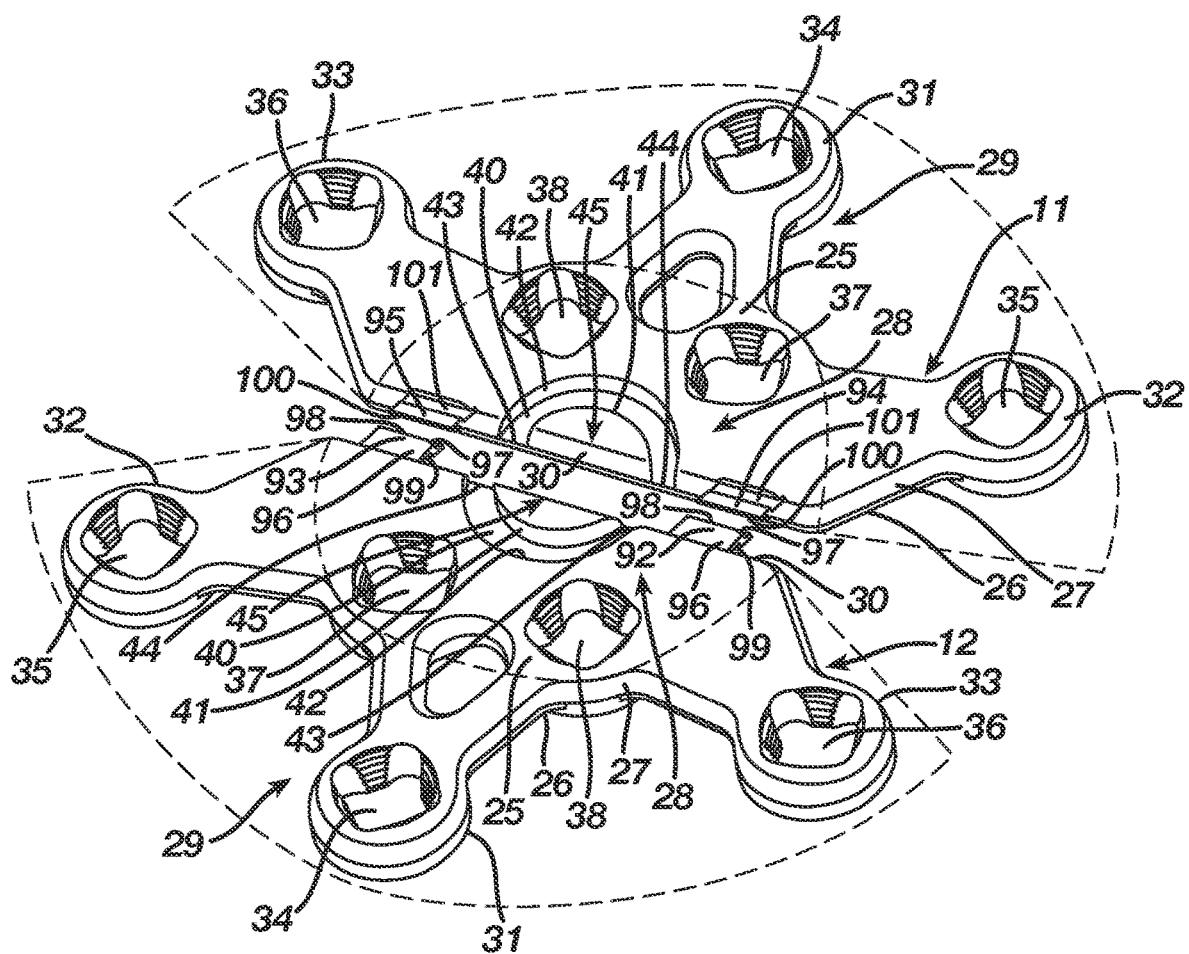
Figure 9C:
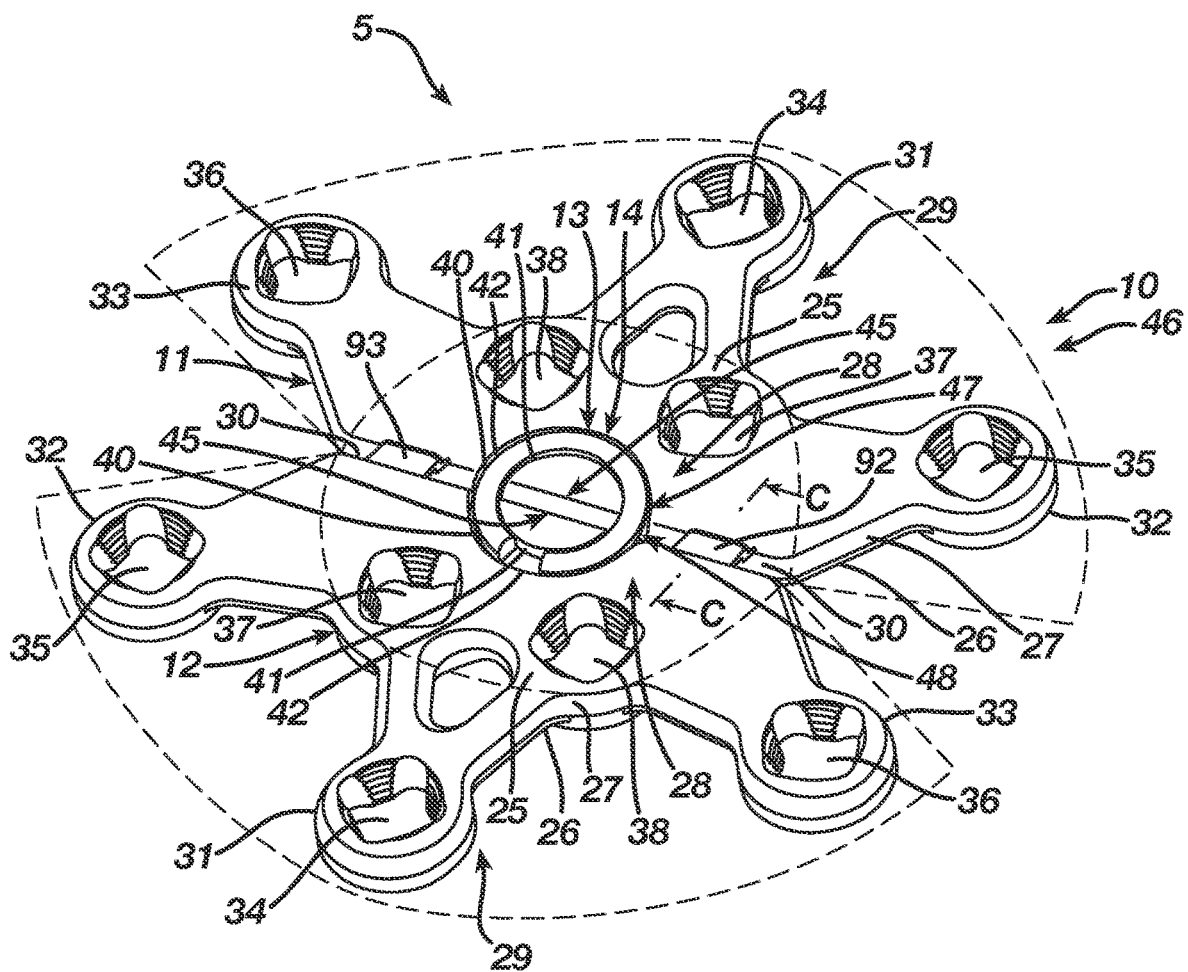
FIG. 9C is top isometric view illustrating the orthopedic implant according to the first embodiment including engagement of the alternative load resistance feature.
Figure 9D:
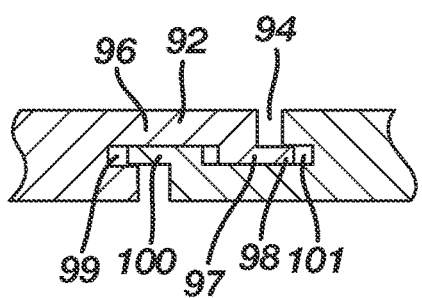
FIG. 9D is a cross-sectional view taken along lines C-C of FIG. 9C illustrating the orthopedic implant according to the first embodiment including engagement of the alternative load resistance feature.

As illustrated in FIG. 7E, the first stabilizer 70 and/or the second stabilizer 71 in an alternative load resistance feature includes grooves 78 cut into the upper and lower surfaces of the first stabilizer 70 and/or the second stabilizer 71 adjacent the sides thereof. In order to accommodate the grooves 78, the first cavity 72 and/or the second cavity 73 includes protrusions 79 extending from the upper and lower surfaces defining the first cavity 72 and/or the second cavity 73 adjacent the sides defining the first cavity 72 and/or the second cavity 73. The grooves 78 and corresponding protrusions 79 increase the surface area contact between the first stabilizer 70 and/or the second stabilizer 71 and the first cavity 72 and/or the second cavity 73.

FIGS. 8A-8D illustrate the orthopedic implant 10 according to the first embodiment including an alternative load resistance feature in the form of at least one alternative stabilizer and an alternative cavity configured complementary in shape with the stabilizer to receive the stabilizer therein. Although a single stabilizer and complementary cavity will provide load resistance to the orthopedic implant 10, the orthopedic implant 10 according to the first embodiment includes a first stabilizer 80 and a first cavity 82 and a second stabilizer 81 and a second cavity 83. The first stabilizer 80 and the first cavity 82 and the second stabilizer 81 and the second cavity 83 are substantially similar in design and operation relative to the first stabilizer 70 and the first cavity 72 and the second stabilizer 71 and the second cavity 73 such that, for the sake of brevity, only differences therebetween will be described herein. Moreover, one of ordinary skill in the art will recognize that the first stabilizer 80 and the first cavity 82 and the second stabilizer 81 and the second cavity 83 incorporate a design and load resistance function as previously set forth in the detailed description of the first stabilizer 70 and the first cavity 72 and the second stabilizer 71 and the second cavity 73. The first and second stabilizers 80 and 81 each include a proximal end 84 and a distal end 85 terminating in a hook 86. The proximal end 84 and the distal end 85 lie in different planes with the proximal end 84 above the distal end 85 in order to provide the first and second stabilizers 80 and 81 with a space 87 below the proximal end 84 and a space 88 above the distal end 85. The first and second cavities 82 and 83 each include a protrusion 89 extending from a lower surface at a front thereof and a protrusion 90 extending from an upper surface near a rear thereof that creates a space 91. In order for the first and second stabilizers 80 and 81 respectively to fit within the first and second cavities 82 and 83, insertion of the first and second stabilizers 80 and 81 respectively into the first and second cavities 82 and 83 includes the space 88 receiving therein the protrusion 90 and the space 87 receiving therein the protrusion 89 whereby the hook 86 enters the space 91 behind the protrusion 90.

FIGS. 9A-9D illustrate the orthopedic implant 10 according to the first embodiment including an alternative load resistance feature in the form of at least one alternative stabilizer and an alternative cavity configured complementary in shape with the stabilizer to receive the stabilizer therein. Although a single stabilizer and complementary cavity will provide load resistance to the orthopedic implant 10, the orthopedic implant 10 according to the first embodiment includes a first stabilizer 92 and a first cavity 94 and a second stabilizer 93 and a second cavity 95. The first stabilizer 92 and the first cavity 94 and the second stabilizer 93 and the second cavity 95 are substantially similar in design and operation relative to the first stabilizer 70 and the first cavity 72 and the second stabilizer 71 and the second cavity 73 such that, for the sake of brevity, only differences therebetween will be described herein. Moreover, one of ordinary skill in the art will recognize that the first stabilizer 92 and the first cavity 94 and the second stabilizer 93 and the second cavity 95 incorporate a design and load resistance function as previously set forth in the detailed description of the first stabilizer 70 and the first cavity 72 and the second stabilizer 71 and the second cavity 73. The first and second stabilizers 92 and 93 each include a proximal end 96 and a distal end 97 terminating in a lip 98. The proximal end 96 defines therein a space 99 at a bottom thereof. The first and second cavities 94 and 95 at a front thereof have a lip 100 while defining a space 101 near a rear thereof. In order for the first and second stabilizers 92 and 93 respectively to fit within the first and second cavities 94 and 95, insertion of the first and second stabilizers 92 and 93 respectively into the first and second cavities 94 and 95 includes the space 99 receiving therein the lip 100 and the space 101 receiving therein the lip 98.

Figure 10A:
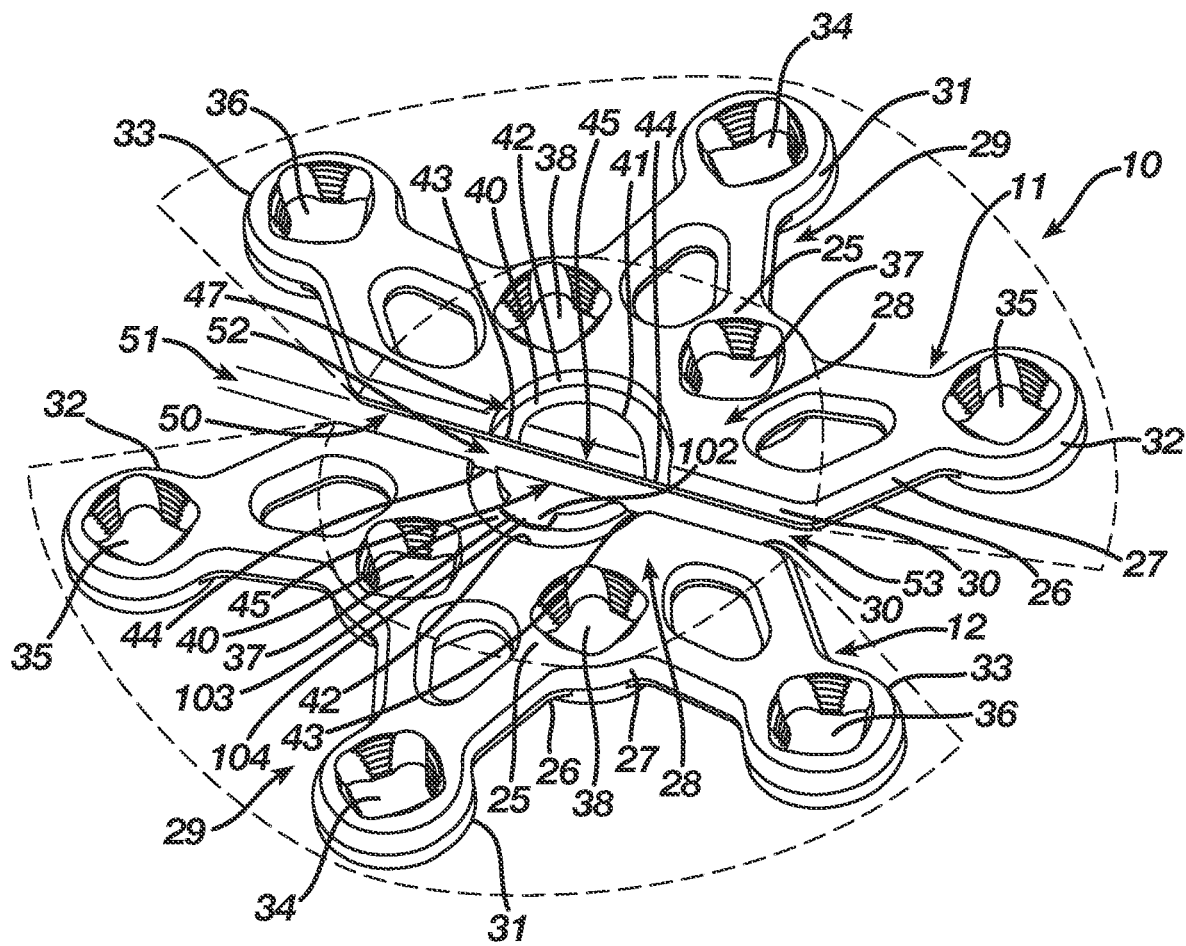
FIG. 10A is a top isometric view illustrating the orthopedic implant according to the first embodiment including an insert retainer.
Figure 10B:
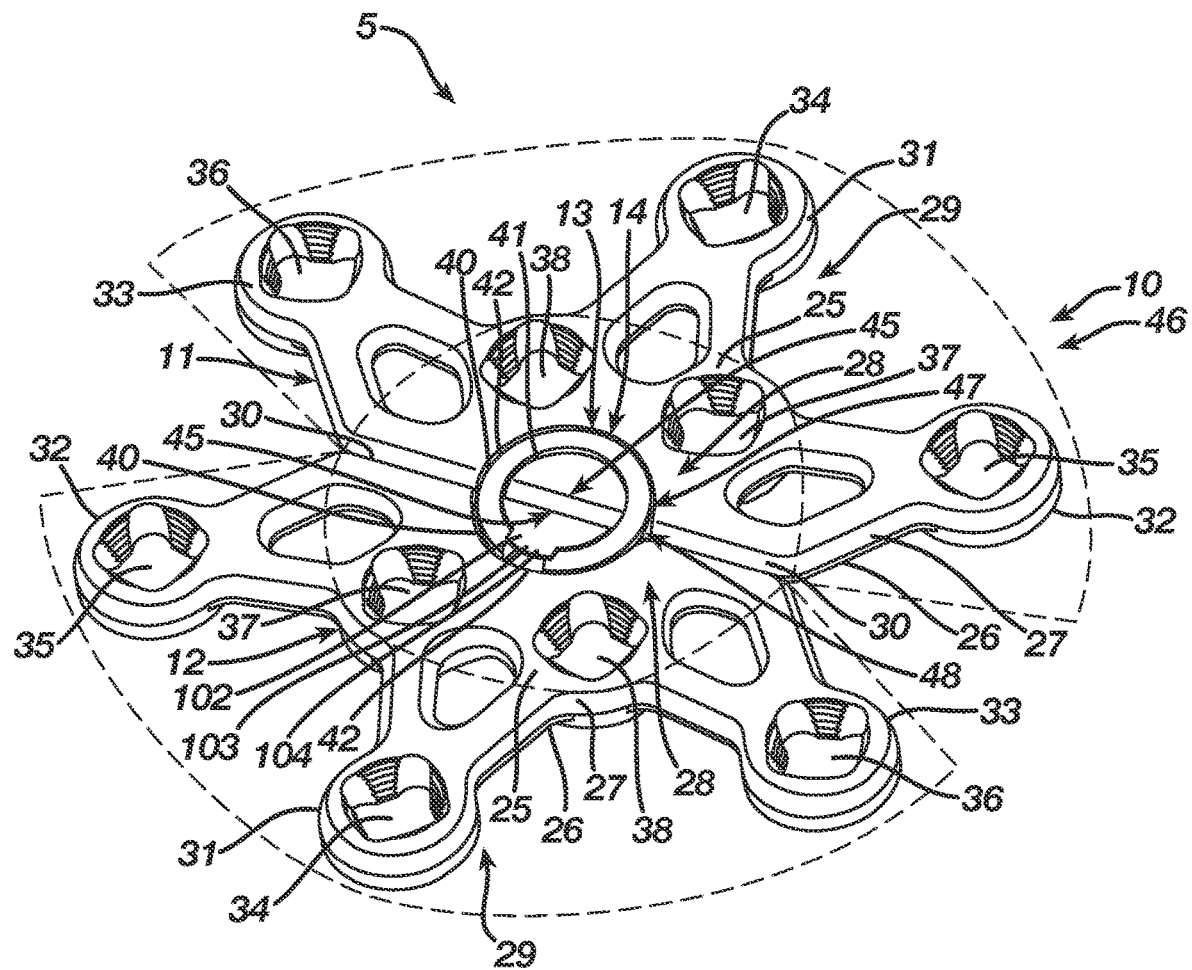
FIG. 10B is a top isometric view illustrating the orthopedic fixation system with the compression insert according to the first embodiment in the natural shape retained by the insert retainer in engagement with the orthopedic implant according to the first embodiment.

FIGS. 10A-10B illustrate the orthopedic implant 10 according to the first embodiment including an insert retainer 102 in the form of a projection 103 extending from the body section 28 of the second plate 12 over the insert slot 40 located centrally relative to the first opening 43 and the second opening 44. The projection 103 in the first embodiment includes a length 104 less than the gap 19 of the compression insert 13 when the compression insert 13 resides in the insertion shape 15 but greater than the gap 19 of the compression insert 13 when the compression insert 13 resides in the natural shape 14. In accordance therewith, the compression insert 13 when in the insertion shape 15 bypasses the implant retainer 102, whereas the implant retainer 102 blocks the compression insert 13 as the compression insert 13 attempts transition from the insertion shape 15 to the natural shape 14. As previously described, the orthopedic implant 10, when employed to affix bone, bones, or bone pieces, begins in the insertion position 49 with the insert retaining pathway 47 including the second width 52 whereby the compression insert 13 while residing in the insertion shape 15 inserts into the insert retaining pathway 47. The projection 103 due to the length 104 thereof allows bypass of the compression insert 13 during insertion of the compression insert 13 into the insert retaining pathway 47. Nevertheless, during attempted transition of the compression insert 13 from the insertion shape 15 to the natural shape 14 and the resulting attempted transition of the orthopedic implant 10 from the insertion position 49 to the natural position 46, the projection 103 due to the length 104 thereof blocks the compression insert 13 thereby retaining the compression insert 13 within the insert retaining pathway 47 because the first end 17 and the second end 18 of the compression insert 13 move under the projection 103. While the insert retainer 102 in the first embodiment is located on the second plate 12, one of ordinary skill in the art will recognize the insert retainer 102 may be located on the first plate 11 in the event the compression insert 13 is inserted with the first and second ends 17 and 18 thereof positioned in the insert slot 40 of the first plate 11.

Figure 11A:
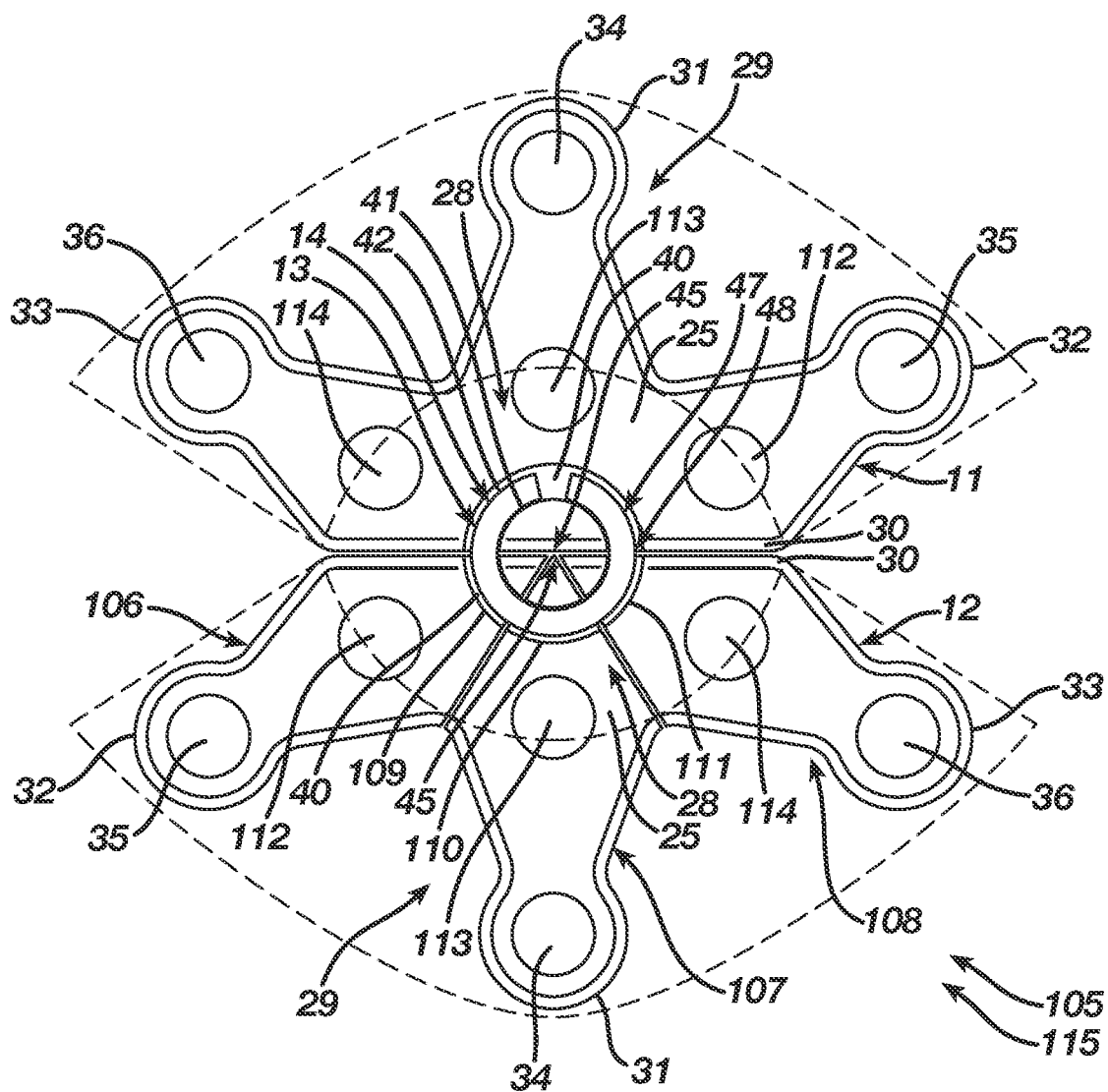
FIG. 11A is a top view illustrating the orthopedic fixation system with the compression insert according to the first embodiment in the insertion shape engaged with an orthopedic implant according to an alternative embodiment.
Figure 11B:
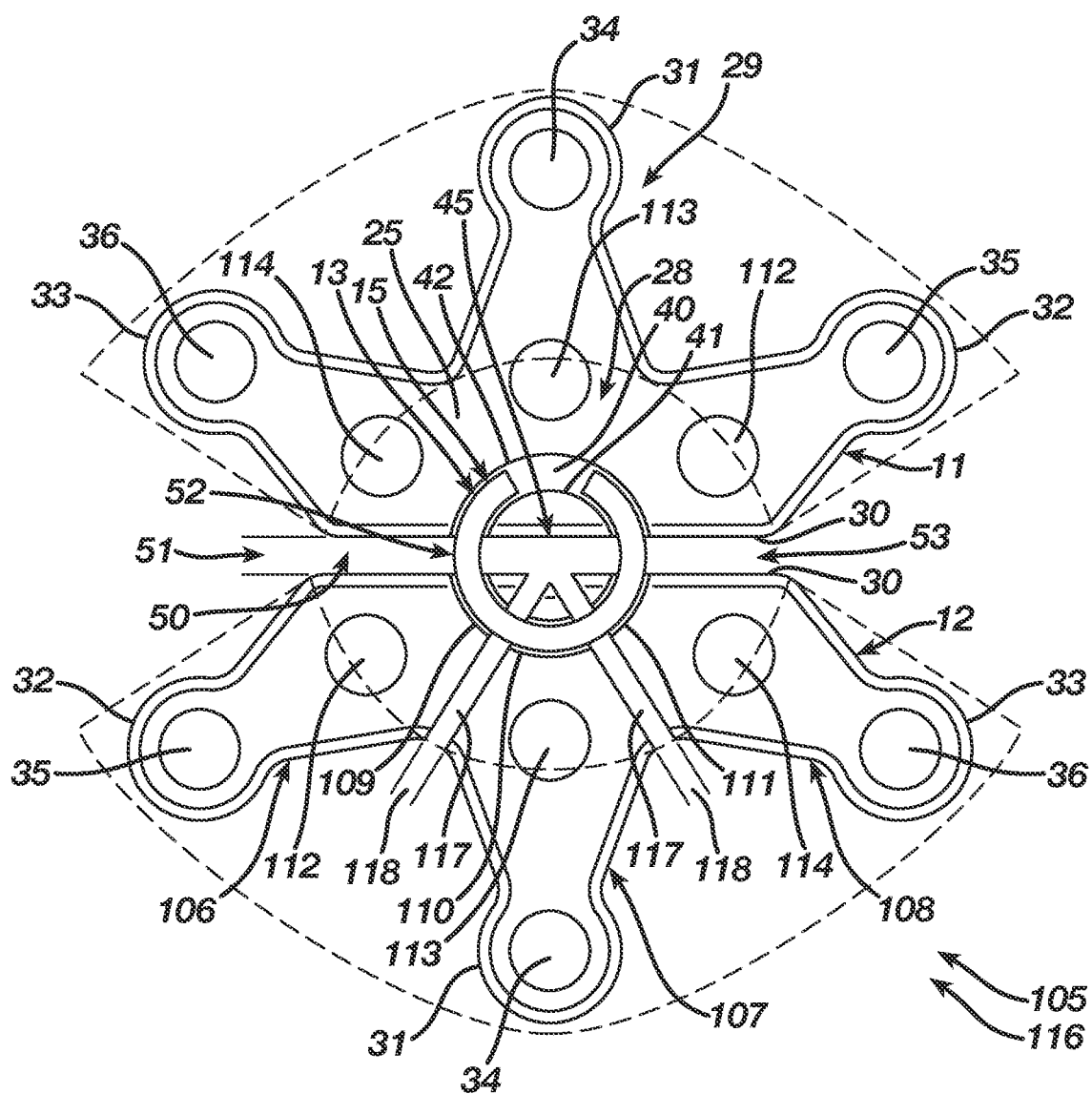
FIG. 11B is a top view illustrating the orthopedic fixation system with the compression insert according to the first embodiment in the natural shape engaged with the orthopedic implant according to the alternative embodiment.
Figure 12A:
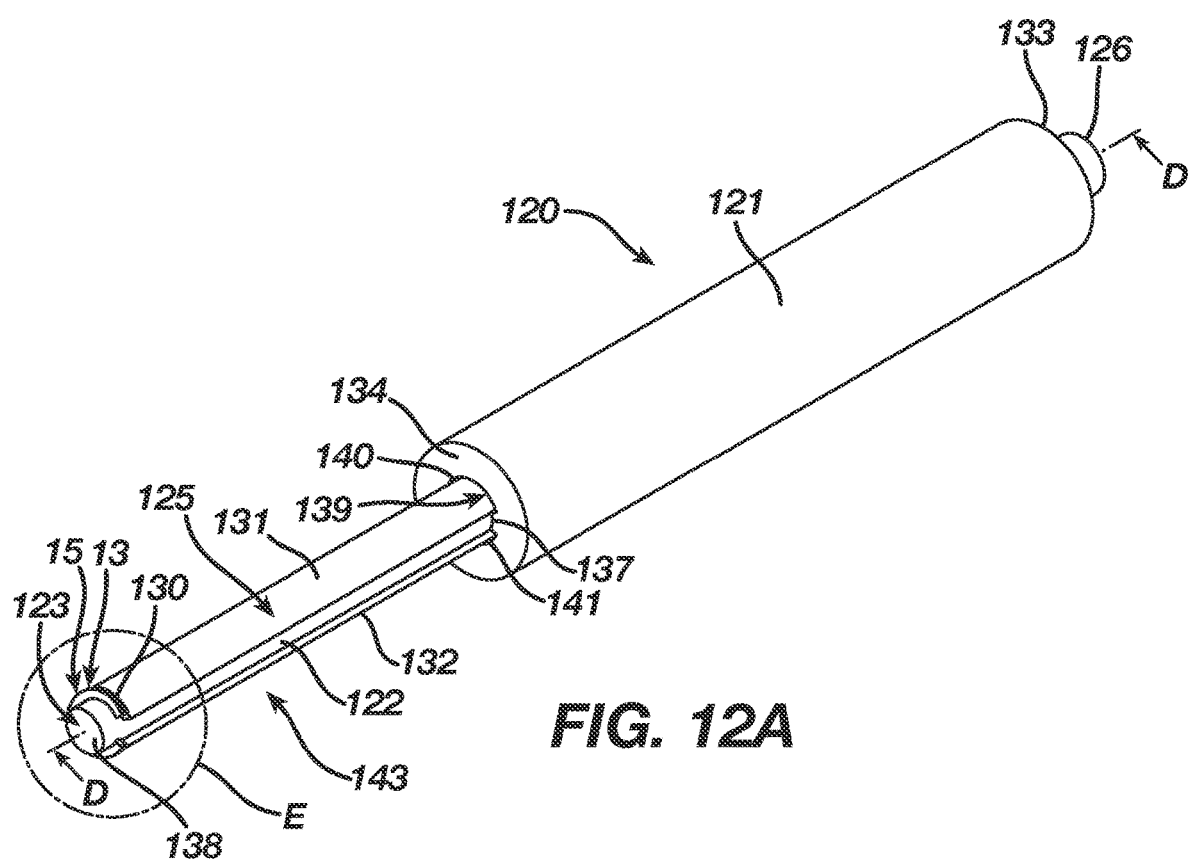
FIG. 12A is an isometric view illustrating an insert delivery device for the compression insert according to the first embodiment.
Figure 12B:
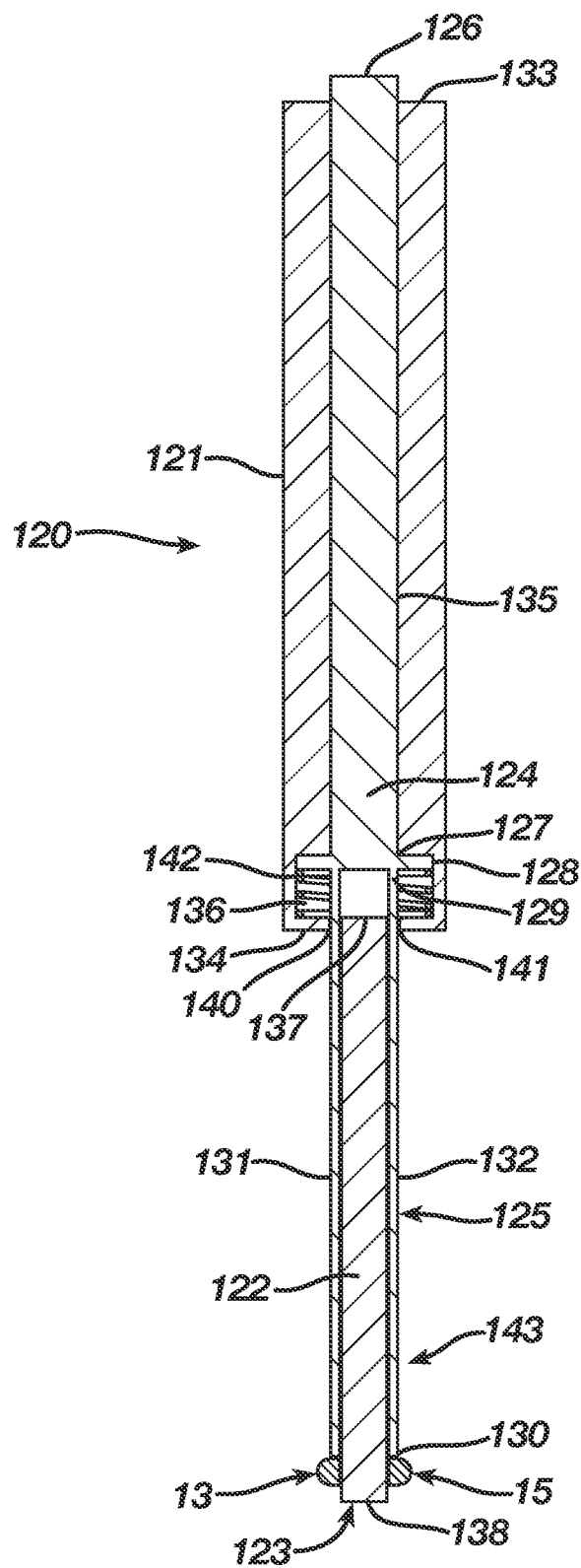
FIG. 12B is a cross-sectional view taken along lines D-D of FIG. 12A illustrating the insert delivery device for the compression insert according to the first embodiment.
Figure 12C:
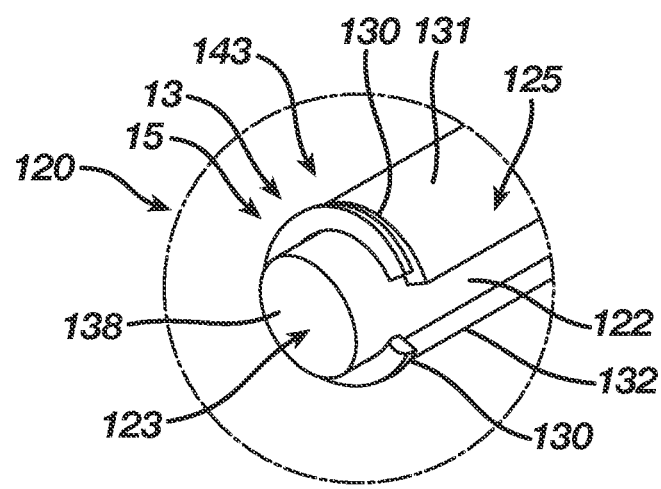
FIG. 12C is an enlarged isometric view taken along circle E of FIG. 12A illustrating the insert delivery device for the compression insert according to the first embodiment.
Figure 12D:
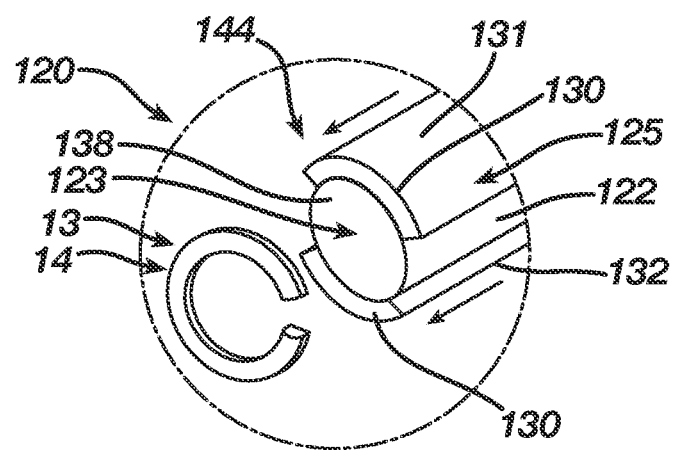
FIG. 12D is an enlarged isometric view illustrating the insert delivery device for the compression insert according to the first embodiment.

FIGS. 11A-11B illustrate the orthopedic fixation system 5 including the compression insert 13 according to the first embodiment and an orthopedic implant 105 alternative to the orthopedic implant 10 of the first embodiment. The orthopedic implant 105 is substantially similar in design and operation relative to the orthopedic implant 10 according to the first embodiment such that, for the sake of brevity, only differences therebetween will be described herein. Moreover, one of ordinary skill in the art will recognize that like parts of the orthopedic implant 105 labeled with like numerals of the orthopedic implant 10 incorporate a design and function as previously set forth in the detailed description of the orthopedic implant 10 according to the first embodiment. The orthopedic implant 10 in the first embodiment includes the first plate 11 and the second plate 12 whereby the first plate 11 and the second plate 12 are unitary. Alternatively, the orthopedic implant 105 includes the first plate 11 or the second plate 12 or both the first plate 11 and the second plate 12 divided into plate segments. In accordance therewith, the second plate 12 as illustrated in FIGS. 11A-11B includes the anchoring member 32 divided from the anchoring member 31 to form a first plate segment 106 and if desired the anchoring member 32 divided from the anchoring member 31 to form a second plate segment 107 and a third plate segment 108. When the anchoring members 32 and 33 are divided from the anchoring member 31, the insert slot 40 divides into a first insert slot segment 109 in the first plate segment 106, a second insert slot segment 110 in the second plate segment 107, and a third insert slot segment 111 in the third plate segment 106. Although the insert slot 40 divides into the first, second, and third insert slot segments 109-111, the first, second, and third insert slot segments 109-111, when the first, second, and third plate segments 106-108 are located directly adjacent, align to include the width 45 along the front face 30 of the second plate 12 substantially equal to the first width 22 of the compression insert 13 produced when the compression insert 13 resides in the natural shape 14. While the anchoring members 32 and 33 divide from the anchoring member 31 at a point equidistant therebetween, one of ordinary skill in the art will recognize the anchoring members 32 and 33 may be divided from the anchoring member 31 at any point provided the resulting plate segment includes an insert slot segment. The first, second, and third plate segments 106-108 may include a respective opening 112, 113, and 114 therethrough configured to receive a suitable fixation device in order to provide additional connection points for the first, second, and third plate segments 106-108 with bone, bones, or bone pieces that improve a securing of the first, second, and third plate segments 106-108 with the bone, bones, or bone pieces.

FIG. 11A illustrates the orthopedic implant 105 residing in a natural position 115 configured for receipt therein of the compression insert 13 when transitioned to the natural shape 14. The orthopedic implant 105 in the natural position 115 includes the first plate 11 at the front face 30 thereof facing the second plate 12 at the front face 30 thereof such that the front faces 30 are aligned while being located directly adjacent. When the first plate 11 and the second plate 12 are aligned with the front faces 30 thereof being located directly adjacent, the first, second, and third plate segments 106-108 of the second plate 12 are located directly adjacent such that the first, second, and third insert slot segments 109-111 align to form the insert slot 40 including the width 45. In accordance therewith, the insert slot 40 of the first plate 11 at the first opening 43 and the second opening 44 aligns with the insert slot 40 of the second plate 12 at the second opening 44 and the first opening 43. The insert slot 40 of the first plate 11 and the insert slot 40 of the second plate 12 formed by the first, second, and third insert slot segments 109-111, when the orthopedic implant 105 resides in the natural position 115, align to provide the orthopedic implant 105 with the insert retaining pathway 47, which, in the orthopedic implant 105 of the alternative embodiment, comprises a continuous pathway traversing the first plate 11 and the second plate 12, and, in particular, the body section 28 of the first plate 11 and the first, second, and third plate segments 106-108 of the second plate 12. The insert retaining pathway 47, accordingly, due to the widths 45 of the insert slots 40 being substantially equal to the first width 22 of the compression insert 13 in combination with the first plate 11 and the second plate 12 being aligned such that the front faces 30 thereof reside directly adjacent, includes a first width 48 taken along the front faces 30 of the first plate 11 and the second plate 12 that is substantially equal to the first width 22 of the compression insert 13 produced when the compression insert 13 resides in the natural shape 14. The first width 48 of the insert retaining pathway 47 along the front faces 30 of the first plate 11 and the second plate 12 is substantially equal to the first width 22 of the compression insert 13 in the natural shape 14 in order for the insert retaining pathway 47 to hold therein the compression insert 13 engaged with the body section 28 of the first plate 11 at the inner surface 41 of the insert slot 40 and the first, second, and third plate segments 106-108 of the second plate 12 at the inner surface 41 of the insert slot 40, thereby ensuring the compression insert 13 remains within the first plate 11 and the second plate 12 and thus the orthopedic implant 105.

FIG. 11B illustrates the orthopedic implant 105 residing in an insertion position 116 configured for receipt therein of the compression insert 13 when deformed into the insertion shape 15. The orthopedic implant 105 in the insertion position 116 includes the first plate 11 at the front face 30 thereof facing the second plate 12 at the front face 30 thereof such that the front faces 30 are aligned while being spaced apart to produce the expansion 50 having the width 51. In addition, the first and third plate segments 106 and 108 are spaced apart from the second plate segment 107 by an expansion 117 having a width 118 while the first and third insert slot segments 109 and 111 are aligned with the second insert slot segment 108. When the first plate 11 and the second plate 12 are aligned with the front faces 30 thereof spaced apart to produce the expansion 50 and the first and third plate segments 106 and 108 spaced apart from the second plate segment 107 by the expansion 117, the insert slot 40 of the first plate 11 aligns at the first opening 43 with the first slot segments 109 and at the second opening 44 with the third insert slot segment 111. The insert slot 40 of the first plate 11 and the first, second, and third insert slot segments 109-111 of the second plate 12, when the orthopedic implant 105 resides in the insertion position 116, align to provide the orthopedic implant 105 with the insert retaining pathway 47, which, in the orthopedic implant 105 of the alternative embodiment, traverses the body section 28 of the first plate 11 and the first, second, and third plate segments 106-108 of the second plate 12, including the expansions 50 and 117. In accordance therewith, the first plate 11 and the second plate 12, on account of their spacing apart in the insertion position 116 of the orthopedic implant 105 to produce the expansion 50 having the width 51 and the expansions 117 having the width 118, provide the insert retaining pathway 47 with a configuration that facilitates an insertion of the compression insert 13 into the insert retaining pathway 47 when the compression insert 13 resides in the insertion shape 15. More particularly, the expansion 50 between the first plate 11 and the second plate 12 and the expansions 117 between the first and third plate segments 106 and 108 and the second plate segment 107 expand the insert retaining pathway 47 to a size sufficient for receipt therein of the compression insert 13 in the insertion shape 15. The insert retaining pathway 47, therefore, due to the width 45 of the insert slot 40 of the first plate 11 being substantially equal to the first width 22 of the compression insert 13 in combination with the first plate 11 being spaced apart from the second plate 12 by the expansion 50 having the width 51 and the first and third plate segments 106 and 108 being spaced apart from the second plate segment 107 by the expansion 117 having the width 118, includes through an expansion thereof a second width 52 taken along the front faces 30 of the first plate 11 and the second plate 12 at the centerline 53 of the expansion 50 that is substantially equal to the second width 24 of the compression insert 13 produced when the compression insert 13 resides in the insertion shape 15. In the alternative embodiment, the width 51 of the expansion 50 is selected to expand the slot 40 of the first plate 11 away from the first, second, and third insert slot segments 109-111 of the second plate 12 and the width 118 of the expansions 117 is selected to expand the first and third plate segments 106 and 108 away from the second plate segment 108 a distance that enlarges the insert retaining pathway 47 to the second width 52 that substantially equals the second width 24 of the compression insert 13 in the insertion shape 15. The second width 52 of the insert retaining pathway 47 along the front faces 30 of the first plate 11 and the second plate 12 at the centerline 53 of the expansion 50 is substantially equal to the second width 24 of the compression insert 13 in the insertion shape 15 in order for the insert retaining pathway 47 to receive therein the compression insert 13 in the insertion shape 15.

When utilizing the orthopedic fixation system 5 to affix bone, bones, or bone pieces and promote a healing thereof, the orthopedic implant 105 while located in the insertion position 116 engages with the bone, bones, or bone pieces across a fixation zone thereof. More particularly, the first plate 11 engages with the bone, bones, or bone pieces at a first side of the fixation zone, whereas the first, second, and third plate segments 106-108 of the second plate 12 engage with the bone, bones, or bone pieces at additional sides of the fixation zone. The first, second, and third plate segments 106-108, upon engagement with the bone, bones, or bone pieces, are aligned while being spaced apart across the additional sides of the fixation zone by the expansions 117 having the width 118. The first plate 11, upon engagement with the bone, bones, or bone pieces, is aligned with the second plate 12 while being spaced apart therefrom across the first side of the fixation zone by the expansion 50 having the width 51. The orthopedic implant 105, therefore, via the first plate 11 and the second plate 12 and the expansions 50 and 117 thereof, includes the insert retaining pathway 47 having the second width 52 that is substantially equal to the second width 24 of the compression insert 13 produced when the compression insert 13 resides in the insertion shape 15. The compression insert 13, which has been deformed to the insertion shape 15 whereby the compression insert 13 stores energy, inserts into the insert retaining pathway 47 on account of the insert retaining pathway 47 including the second width 52. Upon insertion into the insert retaining pathway 47 including a release of any mechanical constraint, the compression insert 13 attempts to transition from the insertion shape 15 to the natural shape 14 such that the compression insert 13 engages with the body section 28 of the first plate 11 at the insert slot 40 and the first, second, and third plate segments 106-108 of the second plate 12 at the first, second, and third insert slot segments 109-111, thereby ensuring the compression insert 13 remains within the first plate 11 and the second plate 12 and thus the orthopedic implant 105. Moreover, the compression insert 13, due to its attempted transition from the insertion shape 15 to the natural shape 14, delivers the energy stored therein to the first plate 11 and the second plate 12 and thus the orthopedic implant 105, resulting in the orthopedic implant 105 attempting to move from the insertion position 116, which includes the expansions 50 and 117, to the natural position 115. In accordance therewith, the orthopedic implant 105 continuously compresses the bone, bones, or bone pieces at the fixation zone thereof whereby the orthopedic fixation system 5 affixes the bone, bones, or bone pieces in order to promote a fusion and a healing thereof. One of ordinary skill in the art will recognize that the sizes of the first plate 11, the first, second, and third plate segments 106-108 of the second plate 12, the insert slot 40, the first, second, and third insert slot segments 109-111, the expansions 50 and 117, and the compression insert 13 are dependent upon the size and configuration of the bone, bones, or bone pieces requiring fixation.

Although the orthopedic implant 105 in the alternative embodiment disclosed the second plate 12 including the first, second, and third plate segments 106-108, one of ordinary skill in the art will recognize the second plate 12 may include only a first plate segment and a larger second plate segment. Moreover, the second plate segment 12 may be unitary while the first plate 11 divides into a first plate segment and a larger second plate segment or first, second, and third plate segments. If the first plate 11 is divided to include plate segments, the first plate 11 similar to the second plate 12 would include the openings 112, 113, and 114. Still further, the first plate 11 and the second plate 12 both may be divided to include plate segments. The orthopedic implant 105 provides improvements in orthopedic surgeries in that the first, second, and third plate segments 106-108 produce compression in comminuted pole fractures of the patella as well as continuous radial compression of multiple bones or bone pieces resulting in a drawing of the multiple bones or bone pieces into a central point until a fusion thereof.

FIGS. 12A-12D illustrate an insert delivery device 120 for the compression insert 13 according to the first embodiment. The insert delivery device 120 includes a barrel 121 with a shaft 122 extending therefrom and a plunger 124 with a blade 125 extending therefrom integrated with the barrel 121 and the shaft 122. The plunger 124 includes a first or top end 126 and a second or bottom end 127 with a flange 128 thereabout. The blade 125 at a proximal end 129 extends from the second or bottom end 127 of the plunger 124 to a distal end 130. The blade 125 includes a first blade 131 located in opposed relationship with a second blade 132 in order to facilitate an interface of the blade 125 at opposite sides of the compression insert 13; nevertheless, one of ordinary skill in the art will recognize the blade 125 may remain unitary.

The barrel 121 includes a first or top end 133, a second or bottom end 134, and a channel 135 therebetween including a cavity 136 adjacent the second or bottom end 134. The shaft 122 at a proximal end 137 extends from the second or bottom end 138 of the barrel 121 to a distal end 138. The shaft 122 includes a width 123, which is a diameter 123, such that, when the compression insert 13 fits on the shaft 122, the shaft 122 maintains the compression insert 13 constrained in the insertion shape 15. The barrel 121 in the second or bottom end 138 thereof includes a slot 139 configured to receive therethrough the blade 125. The slot 139 includes a first slot 140 located in opposed relationship with a second slot 141 whereby the first slot 140 receives therethrough the first blade 131 and the second slot 141 receives therethrough the second blade 132 in order to facilitate an exit of the first and second blades 131 and 132 from the barrel 121; nevertheless, one of ordinary skill in the art will recognize the slot 139 may remain unitary.

The channel 135 is configured to receive therethrough the plunger 124 which is sized to extend from the first or top end 133 of the barrel 121. The cavity 136 is configured to receive therein the flange 128 of the plunger 124 and further is sized to permit movement of the flange 128 within the cavity 136 and thus the plunger 124 relative to the barrel 121. The first blade 131 and the second blade 132 respectively extend through the first slot 140 and the second slot 141 and further along the shaft 122. The cavity 136 includes an elastic device 142 such as a spring located between the flange 128 and the second or bottom end 138 of the barrel 121 that maintains the plunger 124 in a pre-delivery position 143 whereby the first blade 131 and the second blade 132 at the distal ends 130 thereof reside above the distal end 138 of the shaft 122. A movement of the plunger 124 through a pushing thereof at the first or top end 126 transitions the plunger 124 from the pre-delivery position 143 to a delivery position 144 whereby the flange 128 compresses the elastic device 142 as the first blade 131 and the second blade 132 respectively extend further through the first slot 140 and the second slot 141 until the distal ends 130 thereof reside directly adjacent the distal end 138 of the shaft 122. The elastic device 142 upon a release of the plunger 124 acts upon the flange 128 to return the plunger 124 from the delivery position 144 to the pre-delivery position 143.

A loading of the insert delivery device 120 residing in the pre-delivery position 143 includes placing a compression insert 13 deformed from the natural shape 14 to the insertion shape 15 onto the shaft 122 located between the distal end 138 of the shaft 122 and the first blade 131 and the second blade 132 at the distal ends 130 thereof. After loading of the insert delivery device 120 with the compression insert 13, the compression insert 13 using the insert delivery device 120 may be positioned above an orthopedic implant 10 engaged with bone, bones, or bone pieces while residing in the insertion position 49 whereby the insert retaining pathway 47 thereof includes the second width 52. A movement of the plunger 124 from the pre-delivery position 143 to the delivery position 144 progresses the first blade 131 and the second blade 132 along the shaft 122 until the distal ends 130 thereof reside directly adjacent the distal end 138 of the shaft 122. In accordance therewith, the first blade 131 and the second blade 132 engage the compression insert 13 and then push the compression insert 13 from the shaft 122 and thus the insert delivery device 120 such that the compression insert 13 in the insertion shape 15 inserts into the insert retaining pathway 47. Upon release from the insert delivery device 120, the compression insert 13 attempts to transition from the insertion shape 15 to the natural shape 14, resulting in the orthopedic implant 10 attempting to move from the insertion position 49 to the natural position 46, thereby continuously compressing the bone, bones, or bone pieces in order to affix the bone, bones, or bone pieces for a fusion and a healing thereof. Once the compression insert 13 disengages from the shaft 122 and thus the insert delivery device 120, a release of the plunger 124 allows the plunger 124 to return from the delivery position 144 to the pre-delivery position 143.

Figure 13:
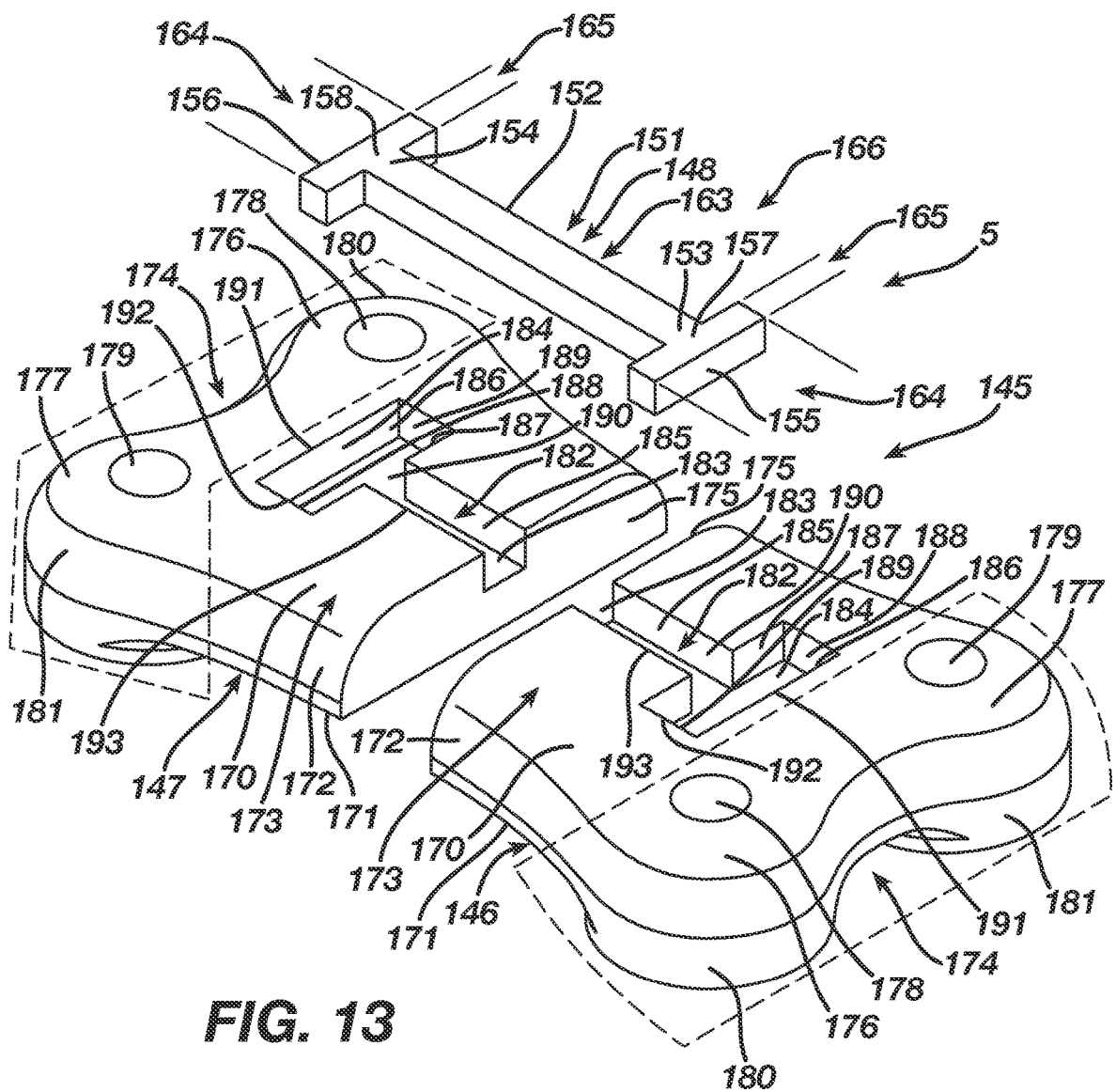
FIG. 13 is a top isometric view illustrating the orthopedic fixation system with a compression insert according to a second embodiment in an insertion shape disengaged from an orthopedic implant according to a second embodiment.

FIG. 13 illustrates the orthopedic fixation system 5 including an orthopedic implant 145 according to a second embodiment engageable with the bone, bones, or bone pieces across a fixation zone thereof. The orthopedic implant 145 includes a first plate 146 engageable with the bone, bones, or bone pieces at a first side of the fixation zone and a second plate 147 engageable with the bone, bones, or bone pieces at a second side of the fixation zone. The first plate 146 and the second plate 147, upon engagement with the bone, bones, or bone pieces, reside in opposed relationship atop the bone, bones, or bone pieces across the fixation zone. The orthopedic fixation system 5 further includes a compression insert 148 according to a second embodiment engageable with the orthopedic implant 145. More particularly, the compression insert 148 engages with the first plate 146 and the second plate 147 across the fixation zone of the bone, bones, or bone pieces thereby securing the first plate 146 with the second plate 147 such that the first plate 146 and the second plate 147 affix the bone, bones, or bone pieces.

Figure 14A:
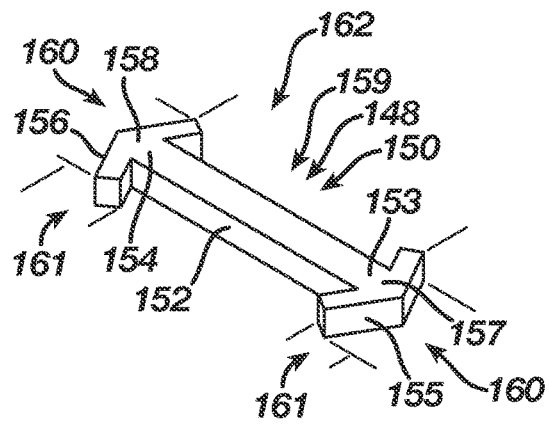
FIG. 14A is a top isometric view illustrating the compression insert according to the second embodiment in the natural shape.
Figure 14B:
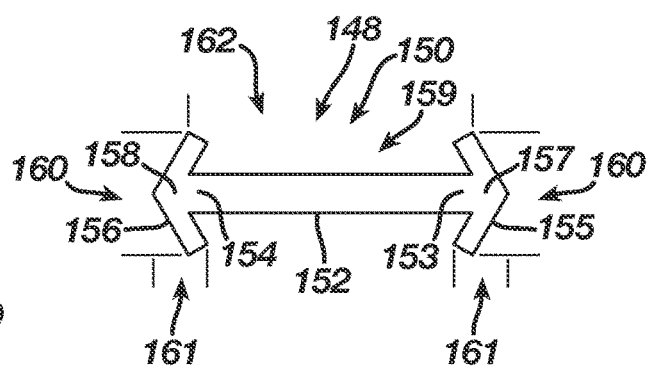
FIG. 14B is a top view illustrating the compression insert according to the second embodiment in the natural shape.
Figure 15A:
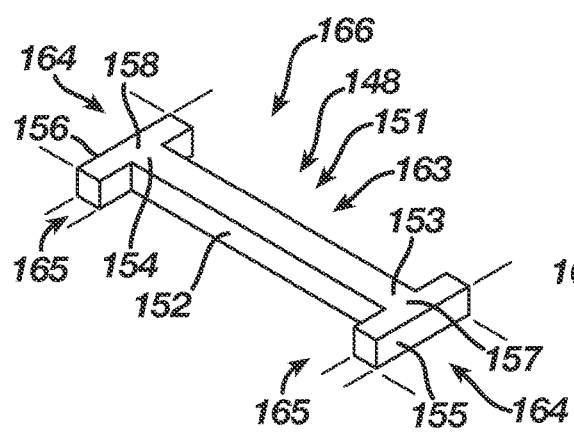
FIG. 15A is a top isometric view illustrating the compression insert according to the second embodiment in the insertion shape.
Figure 15B:
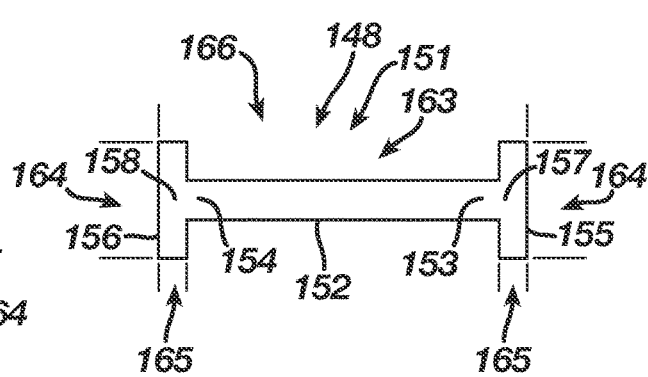
FIG. 15B is a top view illustrating the compression insert according to the second embodiment in the insertion shape.

FIGS. 14A-14B illustrate the compression insert 148 according to the second embodiment in a natural shape 150, whereas FIGS. 15A-15B illustrate the compression insert 148 in the insertion shape 151. The compression insert 148 in the second embodiment may be manufactured from a shape memory material with superelastic or temperature dependent properties (e.g., Nitinol) such that the compression insert 148 transitions between the natural shape 150 and the insertion shape 151. The compression insert 148 when deformed from the natural shape 150 to the insertion shape 151 stores energy deliverable to the orthopedic implant 145. In accordance with its manufacture from shape memory material, the compression insert 148 begins in the natural shape 150, is transitionable to the insertion shape 151, and, once engaged with the orthopedic implant 145, attempts to transition from the insertion shape 151 to the natural shape 150 whereby the compression insert 148 delivers the energy stored therein to the orthopedic implant 145. As will be more fully described herein, an engagement of the compression insert 148 of the second embodiment with the orthopedic implant 145 of the second embodiment, and, more particularly, with the first plate 146 and the second plate 147 thereof across a fixation zone of bone, bones, or bone pieces, followed by an attempted transition of the compression insert 148 from the insertion shape 151 to the natural shape 150 facilitates the orthopedic implant 145 continuously compressing bone, bones, or bone pieces to promote fusion thereof.

The compression insert 148 includes a shaft 152 terminating at a first end 153 in a first beam 155 positioned in the second embodiment transverse relative to the shaft 152 and at a second end 154 in a second beam 156 positioned in the second embodiment transverse relative to the shaft 152. The first beam 155 adjacent the first end 153 includes a first transition section 157. Likewise, the second beam 156 adjacent the second end 154 includes a second transition section 158. The first transition section 157 and the second transition section 158 in the second embodiment facilitate transition of the compression insert 148 between the natural shape 150 and the insertion shape 151. The first transition section 157 and the second transition section 158 further due to the location thereof at opposite first and second ends 153 and 154 of the shaft 152 facilitate engagement of the compression insert 148 with the first plate 146 and the second plate 147. The regular inherent shape of the compression insert 148, as illustrated in FIGS. 14A-14B, is the natural shape 150 where the first transition section 157 and the second transition section 158 locate the compression insert 148 in the natural shape 150, which consists of a closed position 159 whereby the first transition section 157 and the second transition section 158 respectively contract the first beam 155 and the second beam 156 such that the first beam 155 and the second beam 156 each include a first width 160 and a first height 161 while being spaced apart at a first distance 162. Nevertheless, as illustrated in FIGS. 15A-15B, the compression insert 148 is deformable under the action of superelasticity or temperature dependent shape memory to the insertion shape 151 where the first transition section 157 and the second transition section 158 deform to store energy while also moving the compression insert 148 from the natural shape 150 to the insertion shape 151, which consists of an open position 163 whereby the first transition section 157 and the second transition section 158 respectively expand the first beam 155 and the second beam 156 such that the first beam 155 and the second beam 156 each include a second width 164 that is greater than the first width 164 and a second height 165 that is less than the first height 161 while being spaced apart at a second distance 166 that is greater than the first distance 162. Since the insertion shape 151 is not the regular inherent shape of the compression insert 148, the orthopedic implant 145, when coupled with the compression insert 148, typically is mechanically constrained using an implant retainer whereby the implant retainer holds the orthopedic implant 145 such that the compression insert 148 is prevented from returning to the natural shape 150 thereof. Alternatively, the compression insert 148 may be mechanically constrained using an insert retainer that maintains the compression insert 148 in the insertion shape 151 until an engagement of the compression insert 148 with the orthopedic implant 145 and a release of the compression insert 148 from the insert retainer.

Referring to FIGS. 13 and 16A-17C, the first plate 146 exhibits a three-dimensional form whereby the first plate 146 between an upper surface 170 and a lower surface 171 includes a thickness 172 sufficient for the first plate 146 to resist deformation after implantation. The upper surface 170 is substantially planar to present the first plate 146 with a lowest possible profile, whereas the lower surface 171 is substantially planar in order for the first plate 146 at the lower surface 171 to seat flush atop bone, bones, or bone pieces. The first plate 146 in the second embodiment is manufactured from any biocompatible metal or metal alloy, such as, for example, titanium, nitinol, stainless steel, titanium alloy, and cobalt chrome alloy.

The first plate 146 includes a body section 173 that provides structural rigidity to the first plate 146 and an anchoring section 174 that provides for a securing of the first plate 146 with bone, bones, or bone pieces. The body section 173 and thus the first plate 146, due to the thickness 172 of the first plate 146, includes a front face 175, which preferably is substantially planar in order to permit the first plate 146 to reside adjacent the second plate 147. The anchoring section 174 of the first plate 146 according to the second embodiment includes at least one anchoring member 176 projecting from the body section 173 such that the anchoring member 176 is located remote from the front face 175. The anchoring member 176 facilitates a securing of the first plate 146 with bone, bones, or bone pieces, and, in accordance therewith, the anchoring member 176 includes an opening 178 therethrough configured to receive a suitable fixation device, such as a biocompatible locking, non-locking, or self-tapping bone screw, that secures the anchoring member 176 and thus the first plate 146 with bone, bones, or bone pieces. Although the anchoring member 176 adequately secures the first plate 146 with bone, bones, or bone pieces, the anchoring section 174 of the first plate 146 in the second embodiment includes an anchoring member 177 with an opening 179 therethrough projecting from the body section 173 such that the anchoring member 177 is located remote from the front face 175. The anchoring member 177 in providing additional connection points for the first plate 146 with bone, bones, or bone pieces improve a securing of the first plate 146 with the bone, bones, or bone pieces. The anchoring members 176-177 in the second embodiment are unitary elements of varying size and shape to allow contouring located at respective corners 180 and 181 of the first plate 146 opposite from the front face 175 thereof whereby a securing of the first plate 146 with bone, bones, or bone pieces distributes the fixation devices inserted through the anchoring members 176-177 via their respective openings 178-179 over a length of the bone, bones, or bone pieces, thereby enhancing the securing of the first plate 146 with the bone, bones, or bone pieces.

The first plate 146 in the body section 173 thereof defines an insert slot 182 including an opening 183 at the front face 175. The insert slot 182 includes a chamber 184 communicating with a channel 185 defining the opening 183 at the front face 175. The chamber 184 includes an upper surface 186, a lower surface 187, and side surfaces 188 and 189 and further an opening 190 in the lower surface 187 that connects the chamber 184 with the channel 185 opposite from the opening 184 therein. The insert slot 182 is configured to receive therein a portion of the compression insert 148 such that the compression insert 148 engages with the first plate 146. The opening 184 into the channel 185 is located at the front face 175 of the first plate 146 in order to permit the compression insert 148 to extend from the first plate 146 for engagement with the second plate 147. The chamber 184 includes dimensions, particularly with respect to a width 191 between the side surfaces 188 and 189 and a height 192 between the upper surface 186 and the lower surface 187, greater than the second width 164 of the first beam 155 or the second beam 156 when the compression insert 148 resides in the insertion shape 151 and minimally greater than the first height 161 of the first beam 155 or the second beam 156 when the compression insert 148 resides in the natural shape 150. The insert slot 182, accordingly, due to the dimensions of the chamber 184 with respect to the width 191 being greater than the second width 164, is configured to receive therein either the first beam 155 or the second beam 156 expanded to the open position 163 of the compression insert 148 in the insertion shape 151 whereby the first beam 155 or the second beam 156 resides at the second width 164. Moreover, the insert slot 182, due to the dimensions of the chamber 184 with respect to the height 192 being greater than the first height 161, is configured to allow the first beam 155 or the second beam 156 to contract in a transition from the open position 163 to the closed position 159 of the compression insert 148 in the natural shape 150 whereby the first beam 155 or the second beam 156 resides at the first height 161. The channel 185 includes dimensions, particularly with respect to a length 193 thereof, sufficient for the channel 185 to receive therein a portion of the shaft 152 of the compression insert 148 while the first beam 155 or the second beam 156, which has been contracted to the first height 161, seats within the chamber 184. The insert slot 182, accordingly, due to the dimensions of the channel 185, maintains a portion of the shaft 152 of the compression insert 148 therein with the first beam 155 or the second beam 156 seated in the chamber 184 while further permitting the compression insert 148 to extend from the insert slot 182 for engagement with the second plate 147.

The second plate 147 is substantially, completely similar in design and operation relative to the first plate 146 such that, for the sake of brevity, only differences therebetween will be described herein. Moreover, one of ordinary skill in the art will recognize that like parts of the second plate 147 labeled with like numerals of the first plate 146 incorporate a design and function as previously set forth in the detailed description of the first plate 146. During use of the orthopedic implant 145, the second plate 147 is employed substantially the same as the first plate 146, except the second plate 147 is reversed relative to the first plate 146. Illustratively, when the first plate 146 engages with bone, bones, or bone pieces at a first side of a fixation zone with the front face 175 thereof residing adjacent the fixation zone, the second plate 147 is reversed relative to the first plate 146 such that the second plate 147 engages with the bone, bones, or bone pieces at a second side of the fixation zone with the front face 175 thereof residing adjacent the fixation zone. In accordance therewith, the second plate 147 mirrors the first plate 146 whereby the front face 175 of the second plate 147 aligns across the fixation zone with the front face 175 of the first plate 146.

Figure 16A:
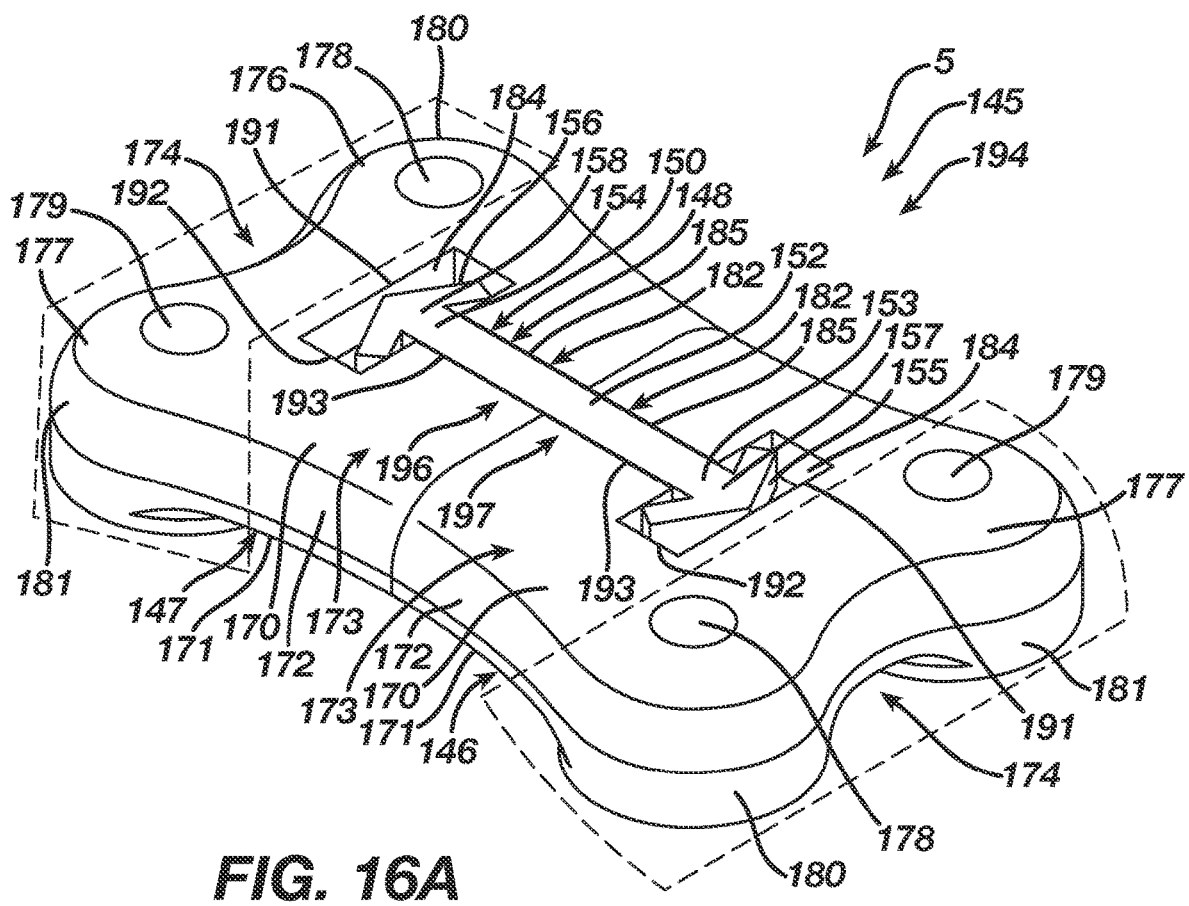
FIG. 16A is a top isometric view illustrating the orthopedic fixation system with the compression insert according to the second embodiment in a natural shape engaged with the orthopedic implant according to the second embodiment.
Figure 16B:
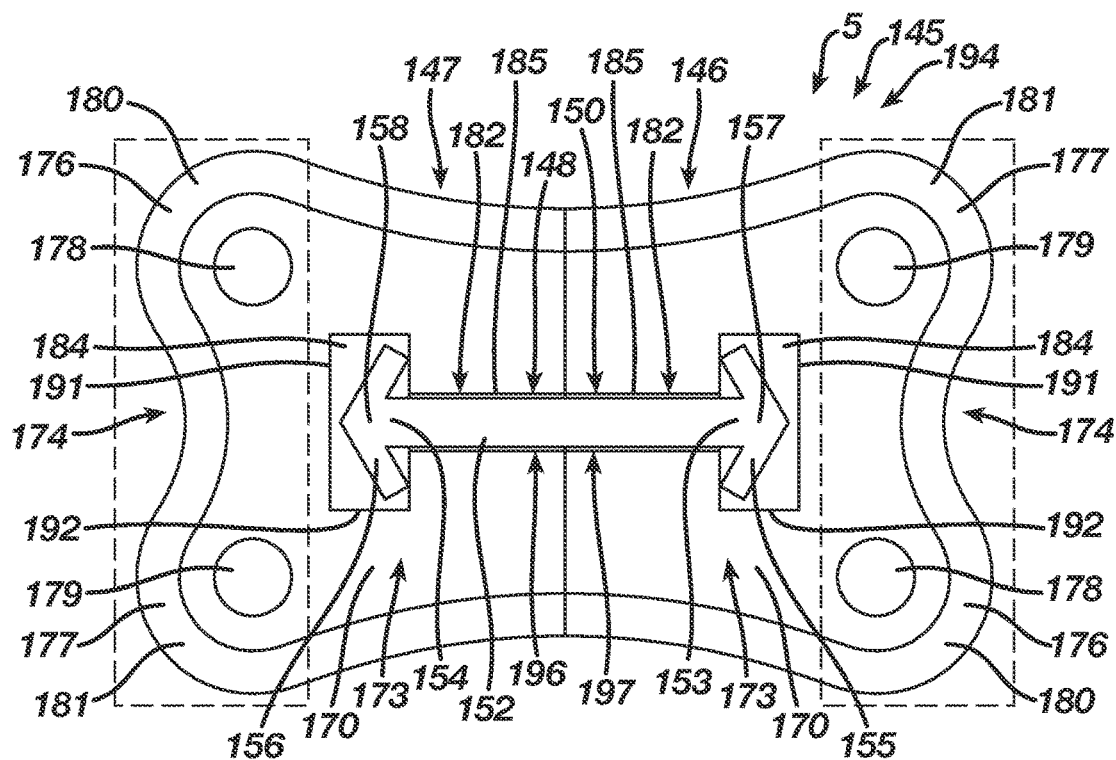
FIG. 16B is a top view illustrating the orthopedic fixation system with the compression insert according to the second embodiment in the natural shape engaged with the orthopedic implant according to the second embodiment.
Figure 16C:
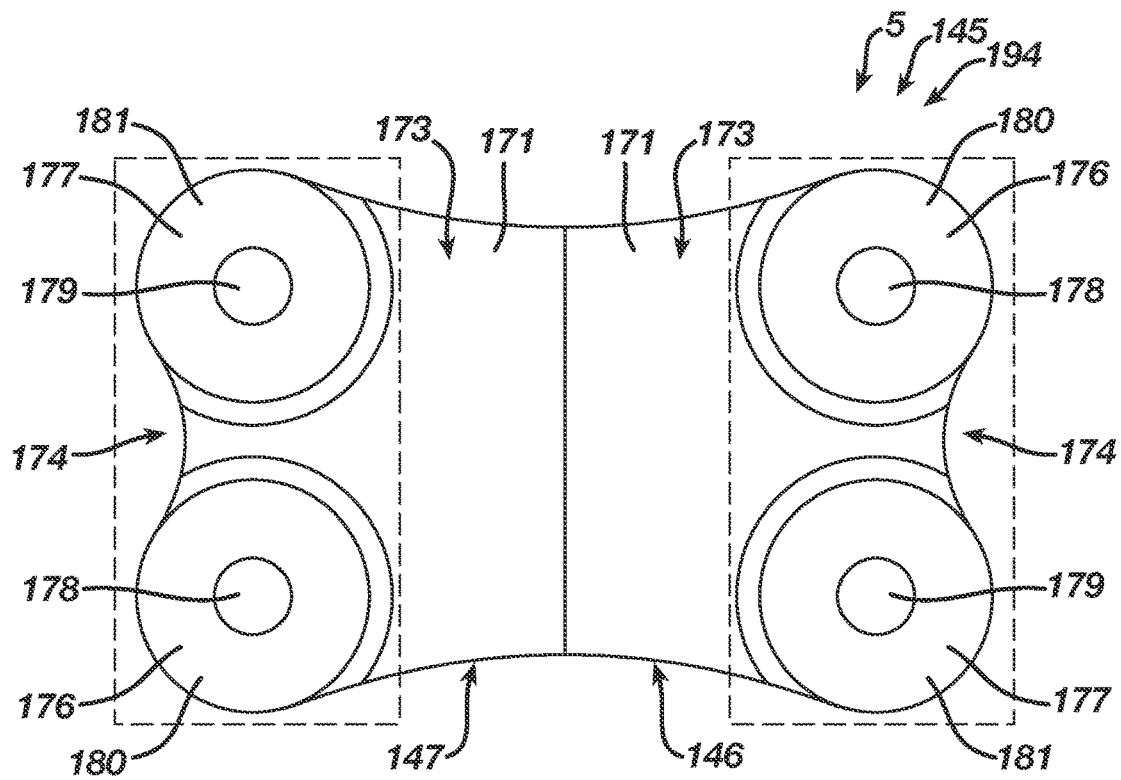
FIG. 16C is a bottom view illustrating the orthopedic fixation system with the compression insert according to the second embodiment in the natural shape engaged with the orthopedic implant according to the second embodiment.

FIGS. 16A-16C illustrate the orthopedic implant 145 according to the second embodiment residing in a natural position 194 configured for receipt therein of the compression insert 148 when transitioned to the natural shape 150. The orthopedic implant 145 in the natural position 194 includes the first plate 146 at the front face 175 thereof facing the second plate 147 at the front face 175 thereof such that the front faces 175 are aligned while being located directly adjacent. When the first plate 146 and the second plate 147 are aligned with the front faces 175 thereof directly adjacent, the insert slot 182 of the first plate 146 at the opening 183 thereof aligns with the insert slot 182 of the second plate 147 at the opening 183 thereof. The insert slots 182 of the first plate 146 and the second plate 147, when the orthopedic implant 145 resides in the natural position 194, align to provide the orthopedic implant 145 with an insert retaining pathway 196, which, in the second embodiment of the orthopedic implant 145, comprises a continuous pathway traversing the first plate 146 and the second plate 147, and, in particular, the body sections 173 of the first plate 146 and the second plate 147. The insert retaining pathway 196, accordingly, due to the length 193 of the channels 185 in the first plate 146 and the second plate 147 and the width 191 and the height 192 of the chambers 184 in the first plate 146 and the second plate 147 in combination with the first plate 146 and the second plate 147 being aligned such that the front faces 175 thereof reside directly adjacent, is configured with a first overall length 197 that seats therein the compression insert 148 in the natural shape 150 with the first beam 155 adjacent the upper surface 186 of the chamber 184 in the first plate 146 and the second beam 156 adjacent the upper surface 186 of the chamber 184 in the second plate 147. The first overall length 197 of the insert retaining pathway 196 is minimally greater than the first distance 162 of the compression insert 148 in the natural shape 150 in order for the insert retaining pathway 196 to hold therein the compression insert 148 engaged with the body sections 173 of the first plate 146 and the second plate 147 at the lower surfaces 187 of the chambers 184 for the insert slots 182, thereby ensuring the compression insert 148 remains within the first plate 146 and the second plate 147 and thus the orthopedic implant 145.

Figure 17A:
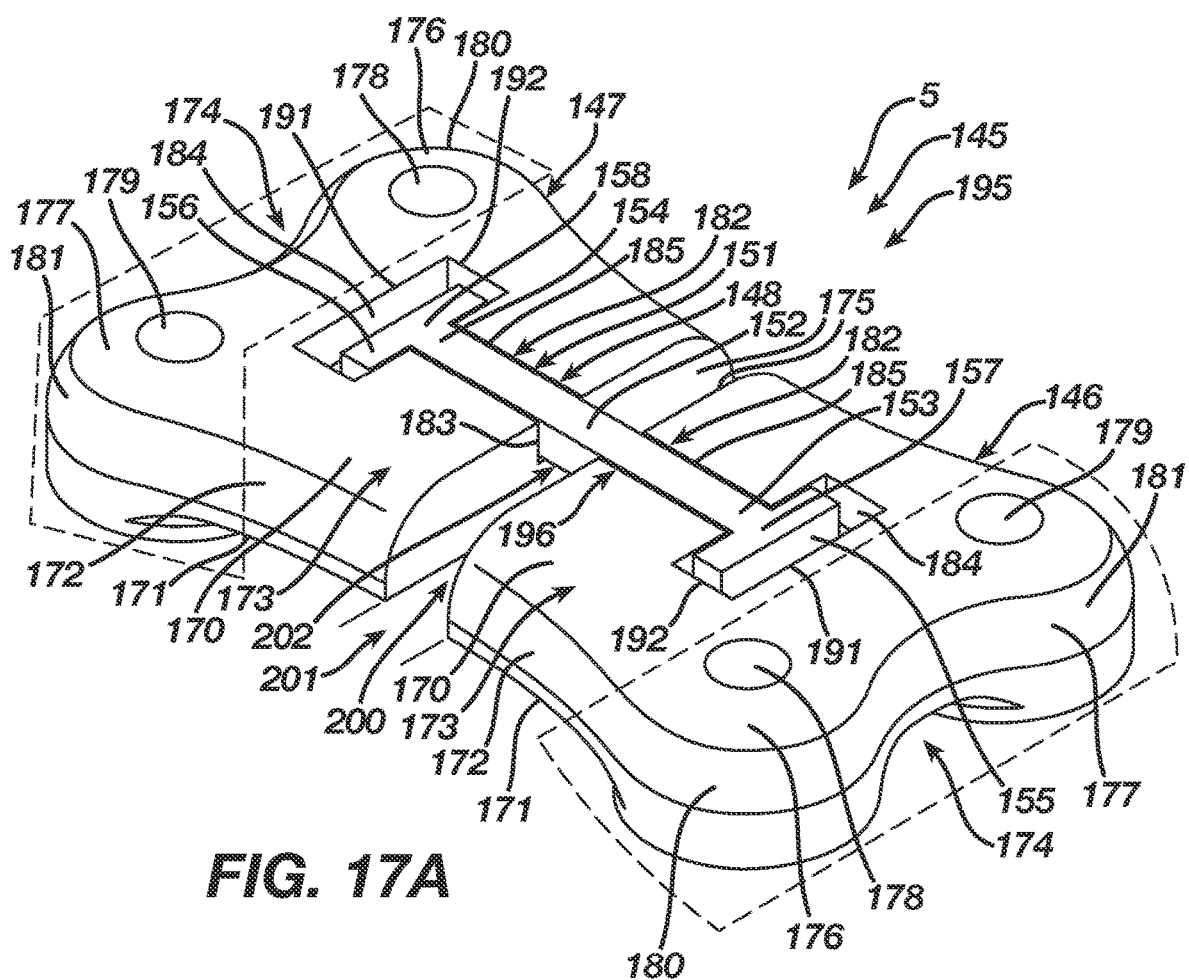
FIG. 17A is a top isometric view illustrating the orthopedic fixation system with the compression insert according to the second embodiment in the insertion shape engaged with the orthopedic implant according to the second embodiment.
Figure 17B:
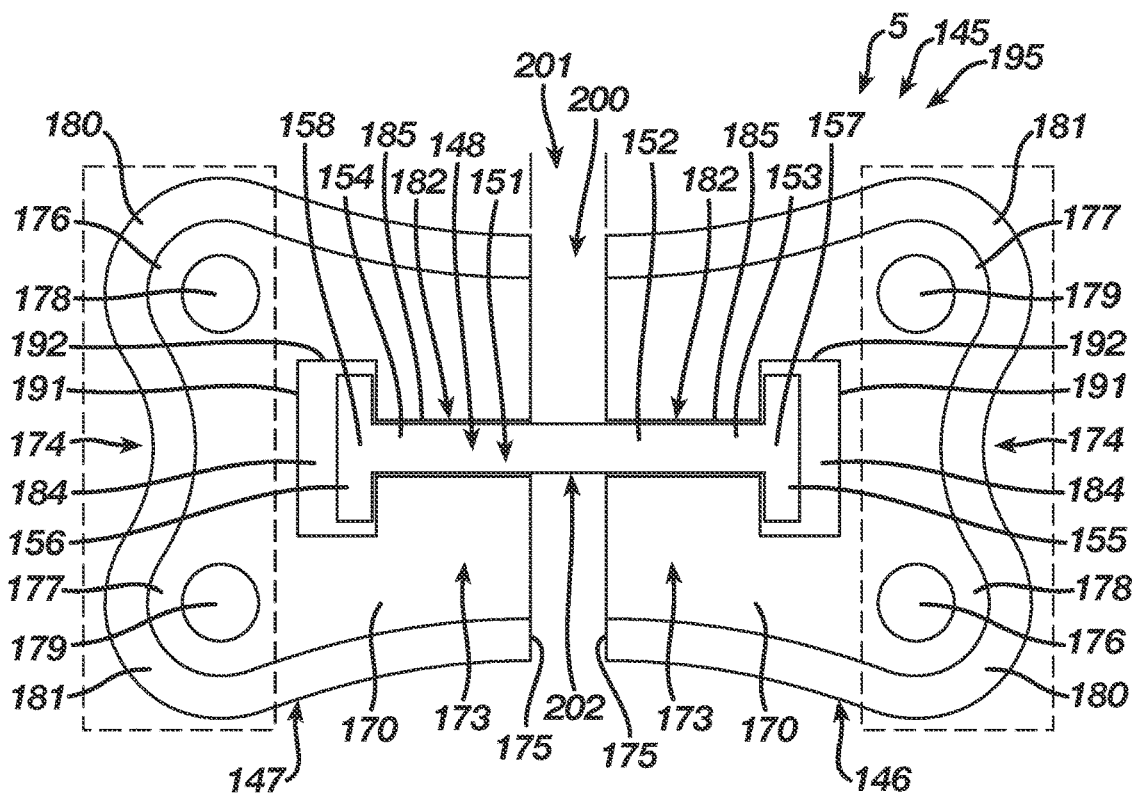
FIG. 17B is a top view illustrating the orthopedic fixation system with the compression insert according to the second embodiment in the insertion shape engaged with the orthopedic implant according to the second embodiment.
Figure 17C:
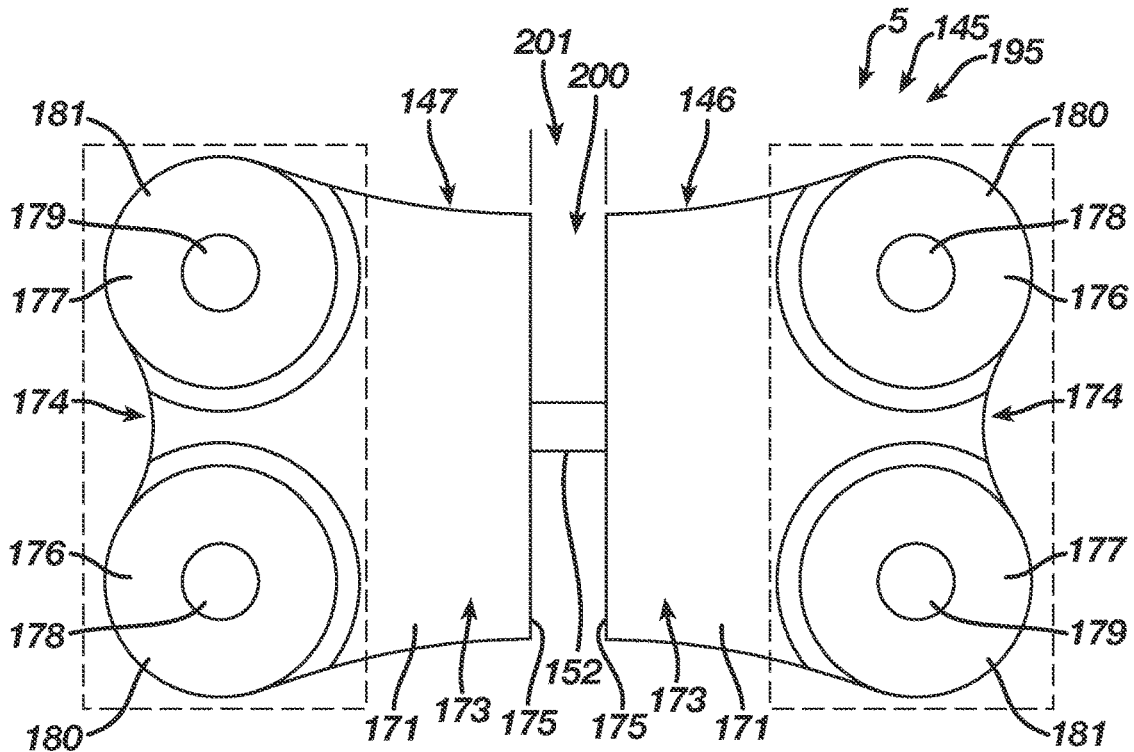
FIG. 17C is a bottom view illustrating the orthopedic fixation system with the compression insert according to the second embodiment in the insertion shape engaged with the orthopedic implant according to the second embodiment.

FIGS. 17A-17C illustrate the orthopedic implant 145 according to the second embodiment residing in an insertion position 195 configured for receipt therein of the compression insert 148 when deformed into the insertion shape 151. The orthopedic implant 145 in the insertion position 195 includes the first plate 146 at the front face 175 thereof facing the second plate 147 at the front face 175 thereof such that the front faces 175 are aligned while being spaced apart to produce an expansion 200 having a width 201. When the first plate 146 and the second plate 147 are aligned with the front faces 175 thereof spaced apart to produce the expansion 200, the insert slot 182 of the first plate 146 at the opening 183 thereof aligns with the insert slot 182 of the second plate 147 at the opening 183 thereof. The insert slots 182 of the first plate 146 and the second plate 147, when the orthopedic implant 145 resides in the insertion position 195, align to provide the orthopedic implant 145 with the insert retaining pathway 196, which, in the second embodiment of the orthopedic implant 145, traverses the body sections 173 of the first plate 146 and the second plate 147, including the expansion 200. In accordance therewith, the first plate 146 and the second plate 147, on account of their being spaced apart in the insertion position 195 of the orthopedic implant 145 to produce the expansion 200 having the width 201, provide the insert retaining pathway 196 with a configuration that facilitates an insertion of the compression insert 148 into the insert retaining pathway 196 when the compression insert 148 resides in the insertion shape 151. More particularly, the expansion 200 between the first plate 146 and the second plate 147 expands the insert retaining pathway 196 to a size sufficient for receipt therein of the compression insert 148 in the insertion shape 151 that also allows the compression insert 148 to continuously compresses the first plate 146 and the second plate 147. The insert retaining pathway 196, therefore, due to the length 193 of the channels 185 in the first plate 146 and the second plate 147 and the width 191 and the height 192 of the chambers 184 in the first plate 146 and the second plate 147 in combination with the first plate 146 and the second plate 147 being aligned such that the front faces 175 thereof are spaced apart to produce the expansion 200 having the width 201, is configured with a second overall length 202 greater than the first overall length 197 that seats therein the compression insert 148 in the insertion shape 151 with the first beam 155 abutting the lower surface 187 of the chamber 184 in the first plate 146 while being spaced apart from the upper surface 186 of the chamber 184 in the first plate 146 and the second beam 156 abutting the lower surface 187 of the chamber 184 in the second plate 147 while being spaced apart from the upper surface 186 of the chamber 184 in the second plate 147. In the second embodiment, the width 201 of the expansion 200 is selected to expand the insert slot 182 of the first plate 146 away from the insert slot 182 of the second plate 147 a distance that enlarges the insert retaining pathway 196 to the second overall length 202 whereby the first beam 155 abuts the lower surface 187 of the chamber 184 in the first plate 146 while being spaced apart from the upper surface 186 of the chamber 184 in the first plate 146 and the second beam 156 abuts the lower surface 187 of the chamber 184 in the second plate 147 while being spaced apart from the upper surface 186 of the chamber 184 in the second plate 147. The insert retaining pathway 196 includes the second overall length 202 in order for the insert retaining pathway 196 to receive therein the compression insert 148 in the insertion shape 151 such that the compression insert 148, which abuts the chambers 184 of the first and second plates 147 at the lower surfaces 187 thereof, continuously compresses the first plate 146 and the second plate 147.

When utilizing the orthopedic fixation system 5 to affix bone, bones, or bone pieces and promote a healing thereof, the orthopedic implant 145 while located in the insertion position 195 engages with the bone, bones, or bone pieces across a fixation zone thereof. More particularly, the first plate 146 engages with the bone, bones, or bone pieces at a first side of the fixation zone, whereas the second plate 147 engages with the bone, bones, or bone pieces at a second side of the fixation zone. The first plate 146 and the second plate 147, upon engagement with the bone, bones, or bone pieces, are aligned at their front faces 175 while being spaced apart across the fixation zone by the expansion 200 having the width 201 such that the orthopedic implant 145 via the first plate 146 and the second plate 147 and the expansion 200 thereof includes the insert retaining pathway 196 having the second overall length 202. The compression insert 148, which has been deformed to the insertion shape 151 whereby the compression insert 148 stores energy, inserts into the insert retaining pathway 196. The insert retaining pathway 196 on account of the second overall length 202 receives the compression insert 148 therein with the first beam 155 thereof abutting the lower surface 187 of the chamber 184 in the first plate 146 while being spaced apart from the upper surface 186 of the chamber 184 in the first plate 146 and the second beam 156 thereof abutting the lower surface 187 of the chamber 184 in the second plate 147 while being spaced apart from the upper surface 186 of the chamber 184 in the second plate 147. Upon insertion into the insert retaining pathway 196 including a release of any mechanical constraint, the compression insert 148 attempts to transition from the insertion shape 151 to the natural shape 150 such that the compression insert 148 engages with the chambers 184 of the first plate 146 and the second plate 147 at the lower surfaces 187 thereof, thereby ensuring the compression insert 148 remains within the first plate 146 and the second plate 147 and thus the orthopedic implant 145. Moreover, the compression insert 148, due to its attempted transition from the insertion shape 151 to the natural shape 150, delivers the energy stored therein to the first plate 146 and the second plate 147 at the lower surfaces 187 of the chambers 182 thereof and thus the orthopedic implant 145, resulting in the orthopedic implant 145 attempting to move from the insertion position 195, which includes the expansion 200, to the natural position 194. In accordance therewith, the orthopedic implant 145 continuously compresses the bone, bones, or bone pieces at the fixation zone thereof whereby the orthopedic fixation system 5 affixes the bone, bones, or bone pieces in order to promote a fusion and a healing thereof. One of ordinary skill in the art will recognize that the sizes of the first plate 146, the second plate 147, the insert slots 182 including the chambers 184 and the channels 185, the expansion 200, and the compression insert 148 are dependent upon the size and configuration of the bone, bones, or bone pieces requiring fixation.

Figure 18A:
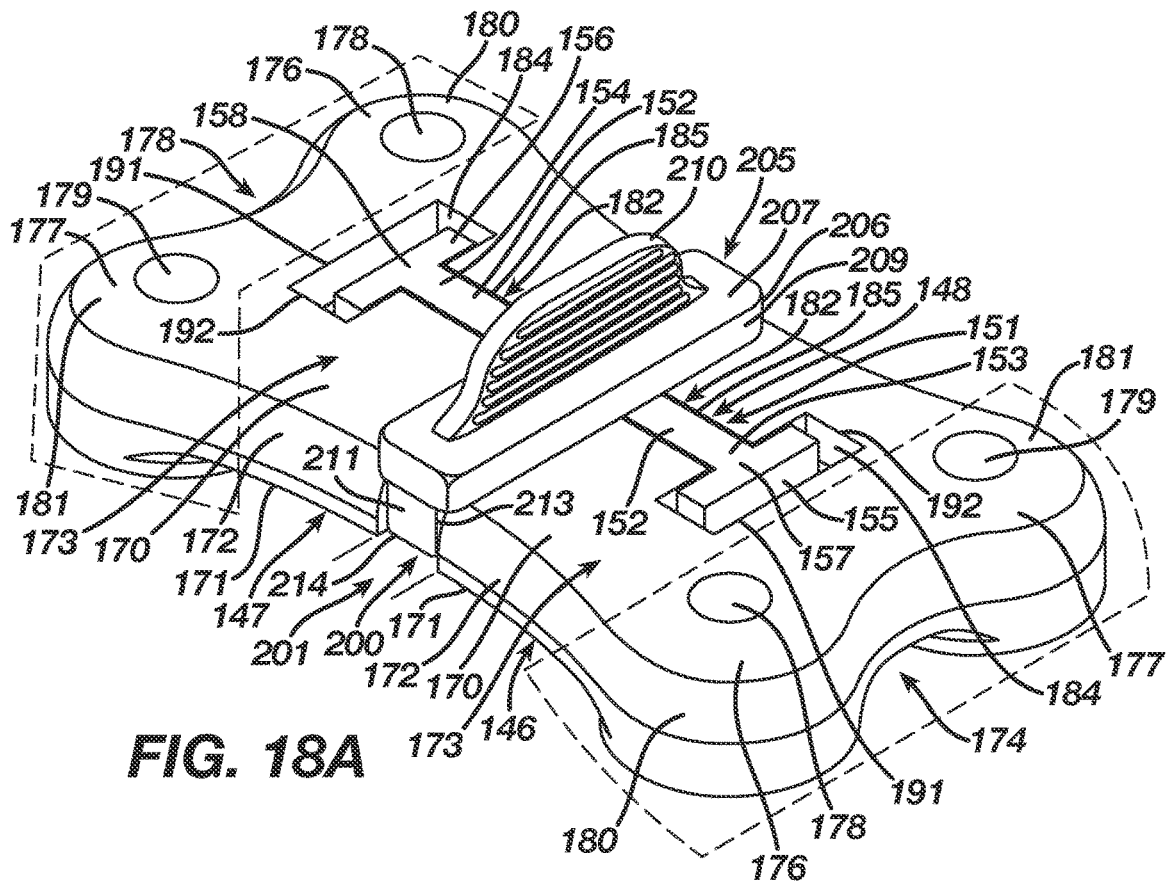
FIG. 18A is a top isometric view illustrating the orthopedic fixation system with an implant retainer according to a second embodiment and the compression insert according to the second embodiment in the insertion shape engaged with the orthopedic implant according to the second embodiment.
Figure 18B:
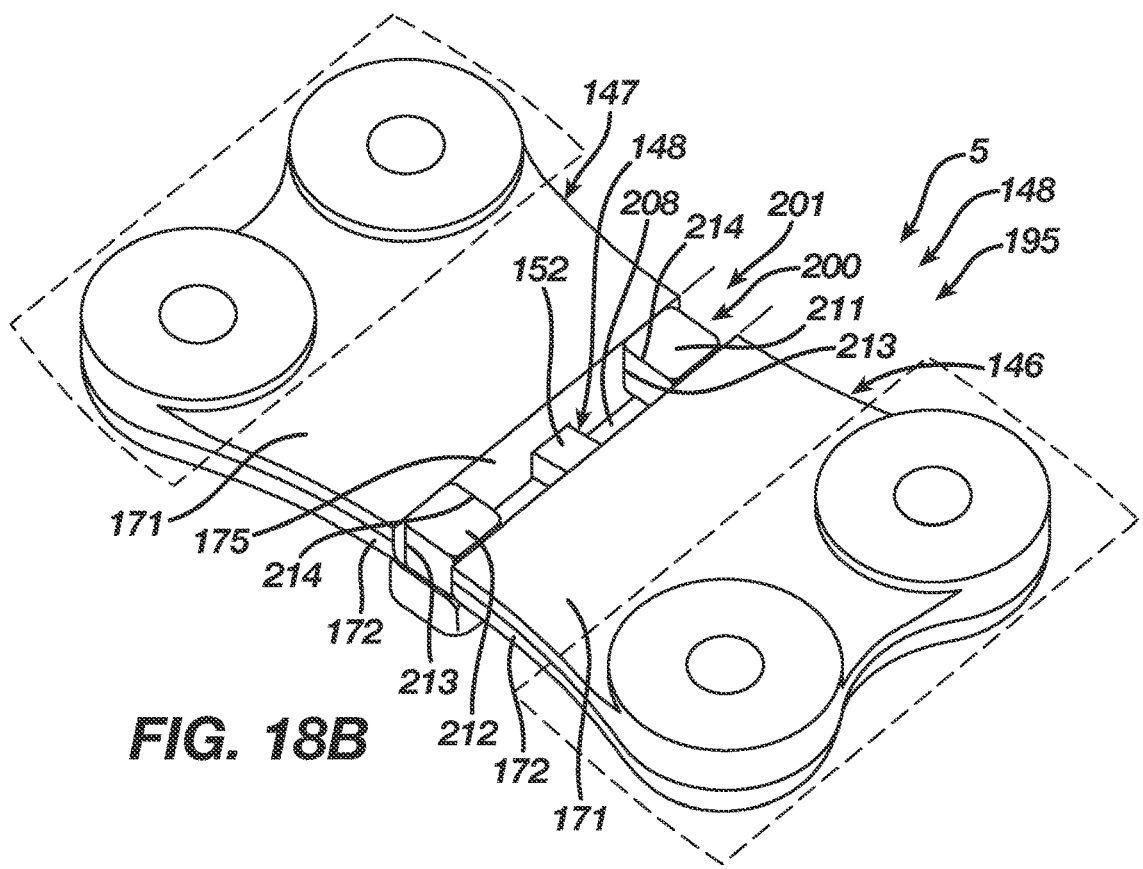
FIG. 18B is a bottom view illustrating the orthopedic fixation system with the implant retainer according to the second embodiment and the compression insert according to the second embodiment in the insertion shape engaged with the orthopedic implant according to the second embodiment.

The orthopedic fixation system 5 as illustrated in FIGS. 18A-18B includes an implant retainer 205 according to a second embodiment configured to hold the compression insert 148 in the insertion shape 151 within the orthopedic implant 145 while retaining the orthopedic implant 145 in the insertion position 195. The implant retainer 205 includes a body 206 that exhibits a three-dimensional form having a length, width, and height, and, in particular, an upper surface 207 and a lower surface 208 defining therebetween a thickness 209 that provides strength to the body 206. The lower surface 208 is substantially planar in order for the implant retainer 205 to seat flush atop the orthopedic implant 145. The implant retainer 205 includes a grip 210 extending from the upper surface 207 of the body 206 that facilitates grasping of the implant retainer 205. The implant retainer 205 includes at least a first block 211 projecting from the lower surface 208 of the body 206 and preferably a first block 211 and a second block 212 projecting from the lower surface 208 of the body 206. The first block 211 and the second block 212 in the second embodiment are located along the body 206 adjacent opposite ends thereof. The first block 211 and the second block 212 are located adjacent opposite ends of the body 206 in order for the first block 211 and the second block 212 to engage the orthopedic fixation system 5 exterior of the compression insert 148. The first block 211 and the second block 212 each project from the lower surface 208 of the body 206 a distance 213 less than or equal to the thickness 172 of the first plate 146 and the second plate 147 whereby the implant retainer 205 does not interfere with the ability of the orthopedic implant 145 to sit flush atop bone, bones, or bone pieces. The first block 211 and the second block 212 each include a width 214 substantially equal to the width 201 of the expansion 200 between the first plate 146 and the second plate 147 when the orthopedic implant 145 resides in the insertion position 195. In accordance therewith, the implant retainer 205, after orienting the orthopedic implant 145 in the insertion position 195 followed by a placement of the compression insert 148 in the insertion shape 151 within the insert retaining pathway 196, engages with the orthopedic implant 145. More particularly, the body 206 of the implant retainer 205 sits atop the orthopedic implant 145 while the first block 211 and the second block 212 insert into the expansion 200 exterior of the compression insert 148. The implant retainer 205, via the first block 211 and the second block 212 and the widths 214 thereof, holds the first plate 146 spaced apart from the second plate 147 such that the implant retainer 205 prevents transition of the compression insert 148 from the insertion shape 151 to the natural shape 150 thereby maintaining the orthopedic implant 145 in the insertion position 195.

Figure 19A:
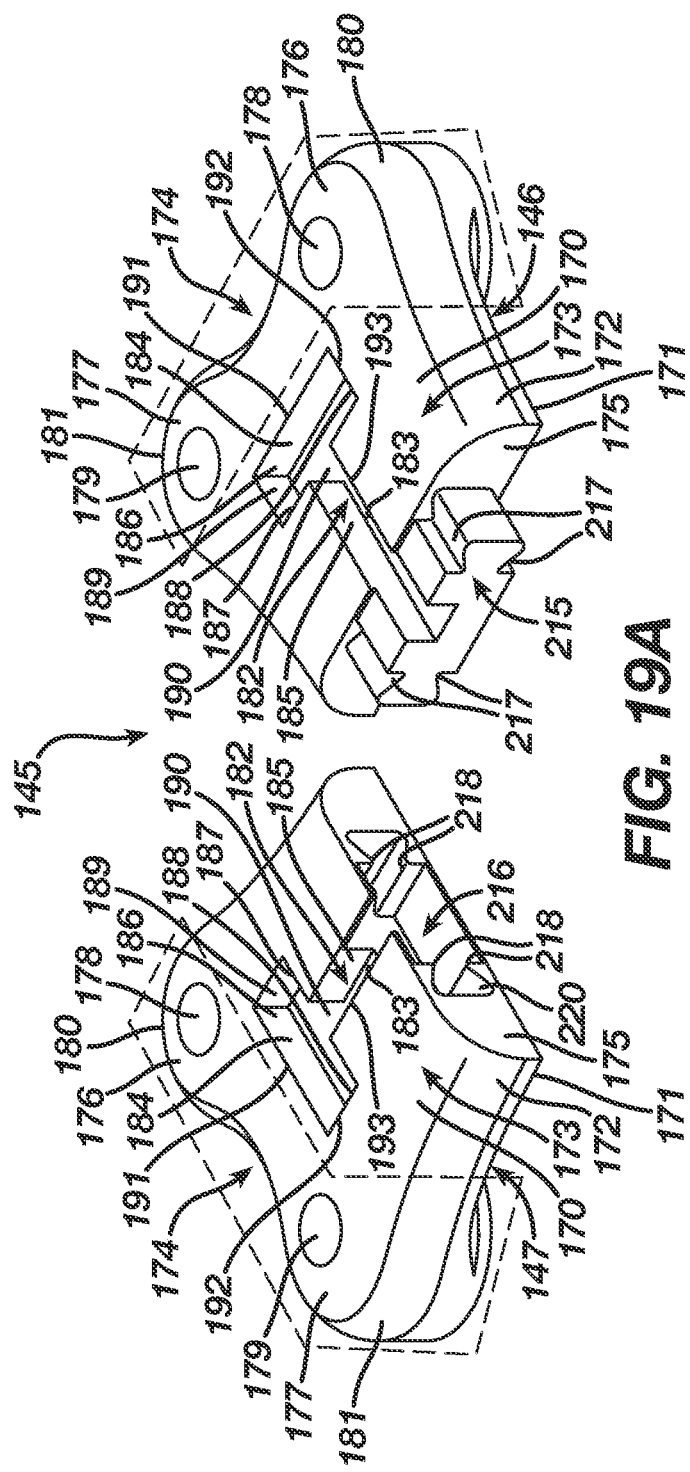
FIG. 19A is a top isometric view illustrating the orthopedic implant according to the second embodiment including load resistance features.
Figure 19B:
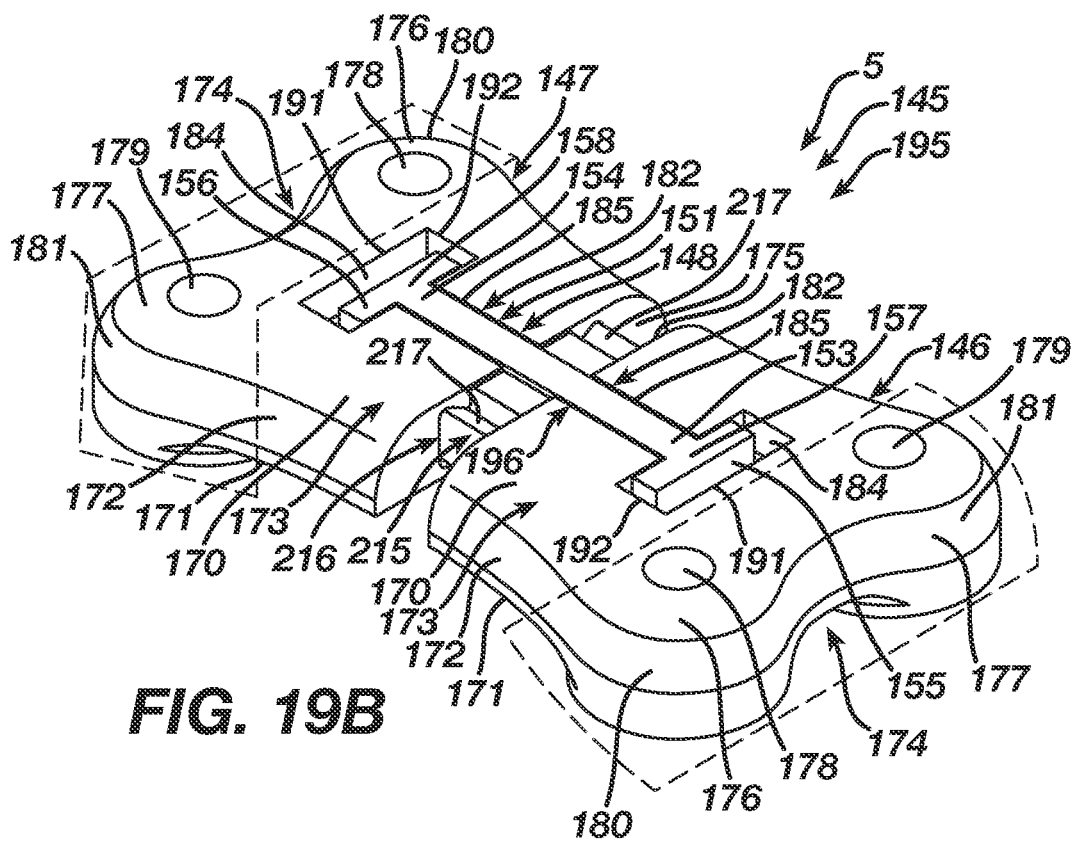
FIG. 19B is a top isometric view illustrating the orthopedic fixation system with the compression insert according to the second embodiment in the insertion shape engaged with the orthopedic implant according to the second embodiment including load resistance features.
Figure 19C:
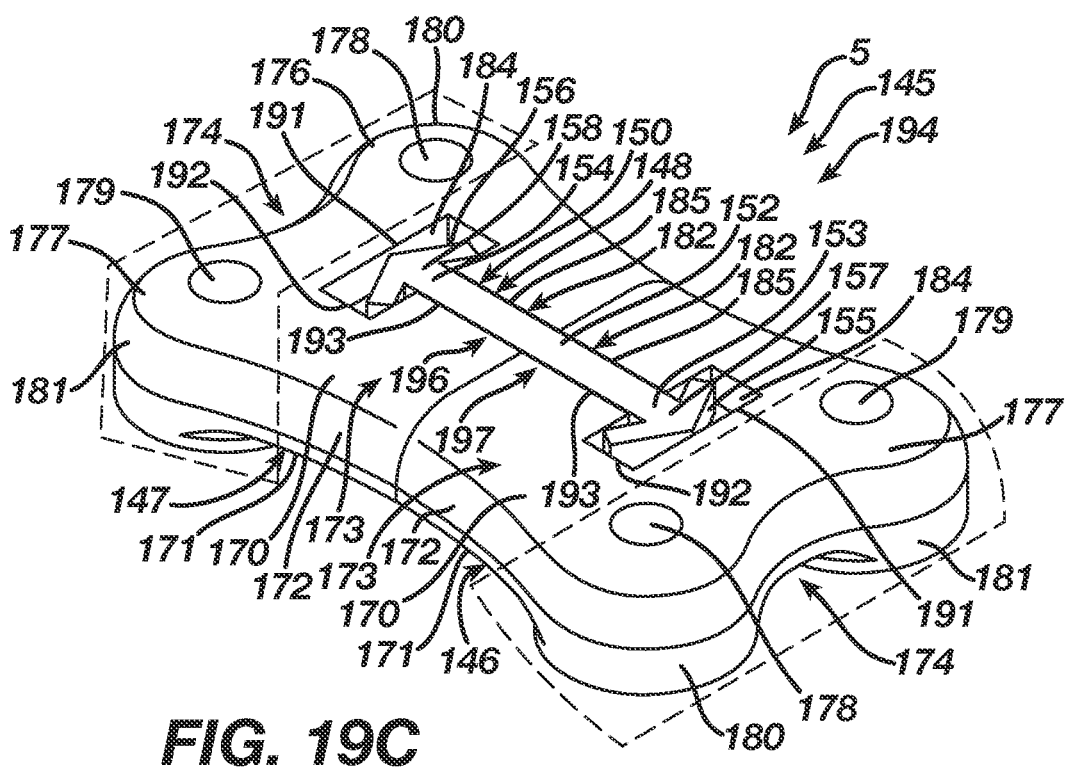
FIG. 19C is a top isometric view illustrating the orthopedic fixation system with the compression insert according to the second embodiment in the natural shape engaged with the orthopedic implant according to the second embodiment including load resistance features.
Figure 20A:
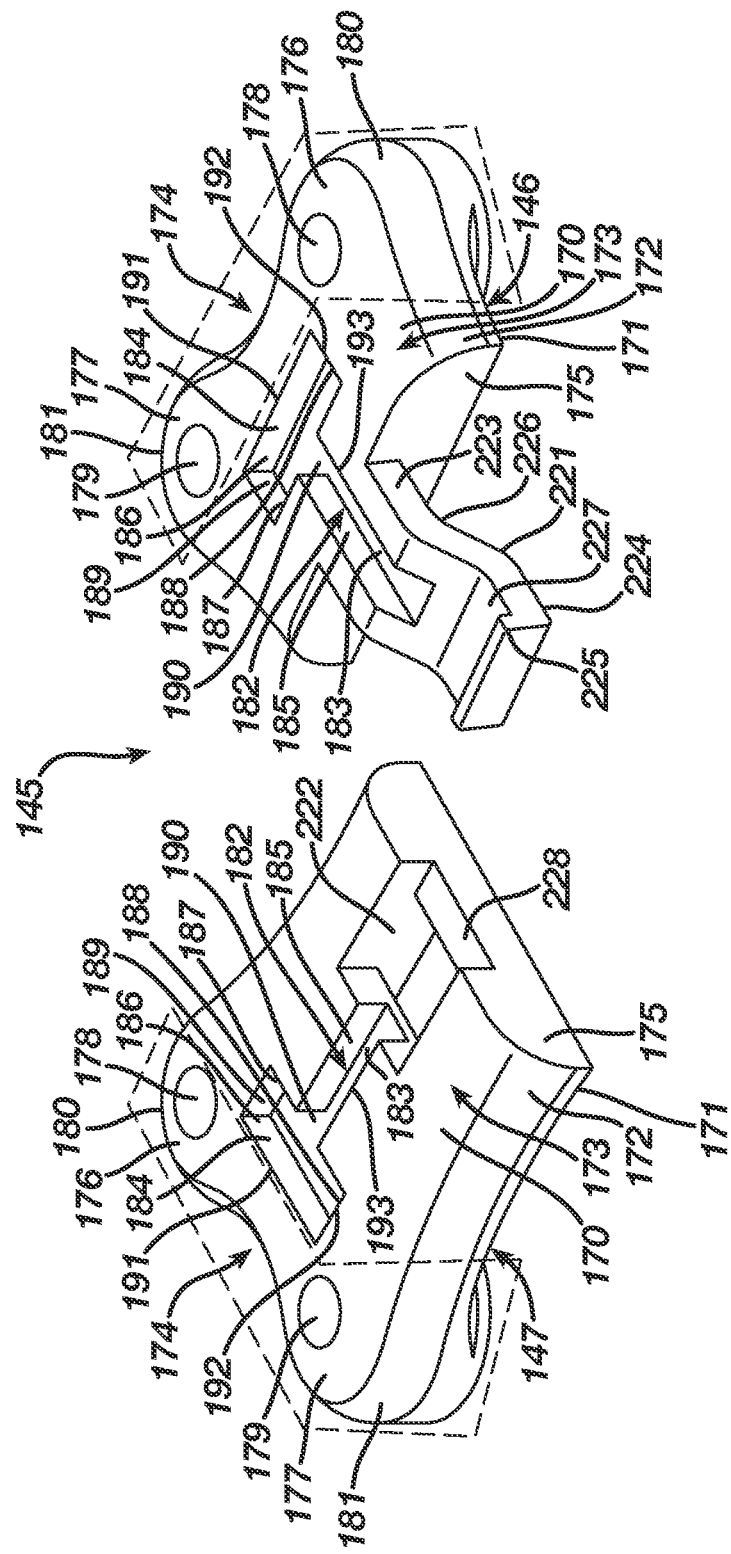
FIG. 20A is a top isometric view illustrating the orthopedic implant according to the second embodiment including alternative load resistance features.
Figure 20B:
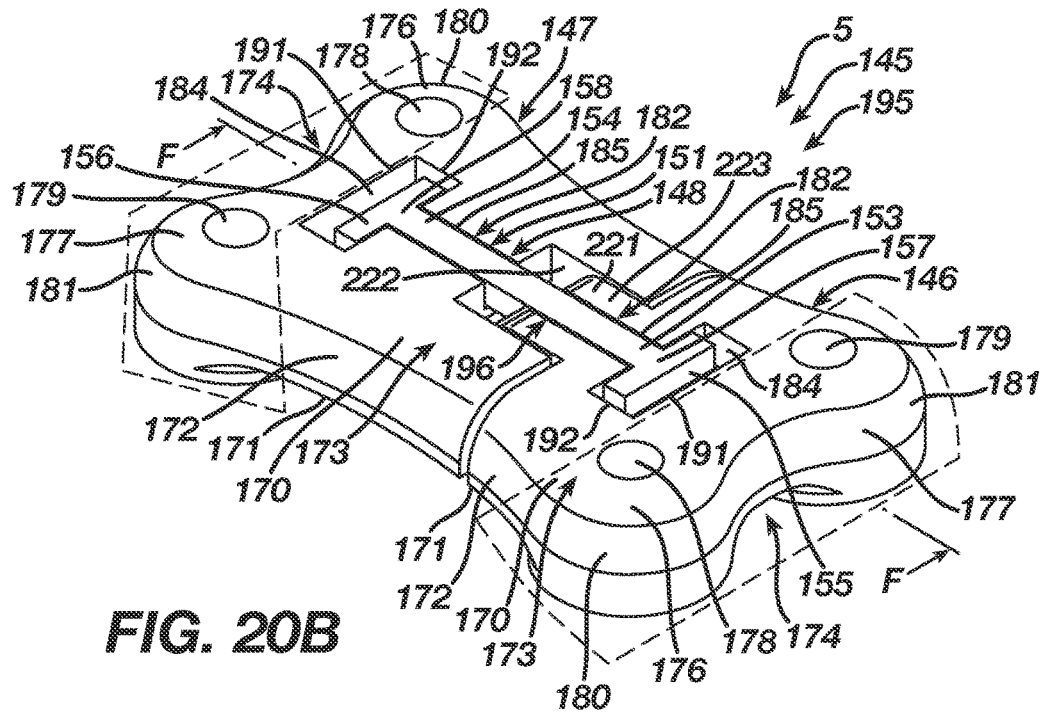
FIG. 20B is a top isometric view illustrating the orthopedic fixation system with the compression insert according to the second embodiment in the insertion shape engaged with the orthopedic implant according to the second embodiment including alternative load resistance features.
Figure 20C:
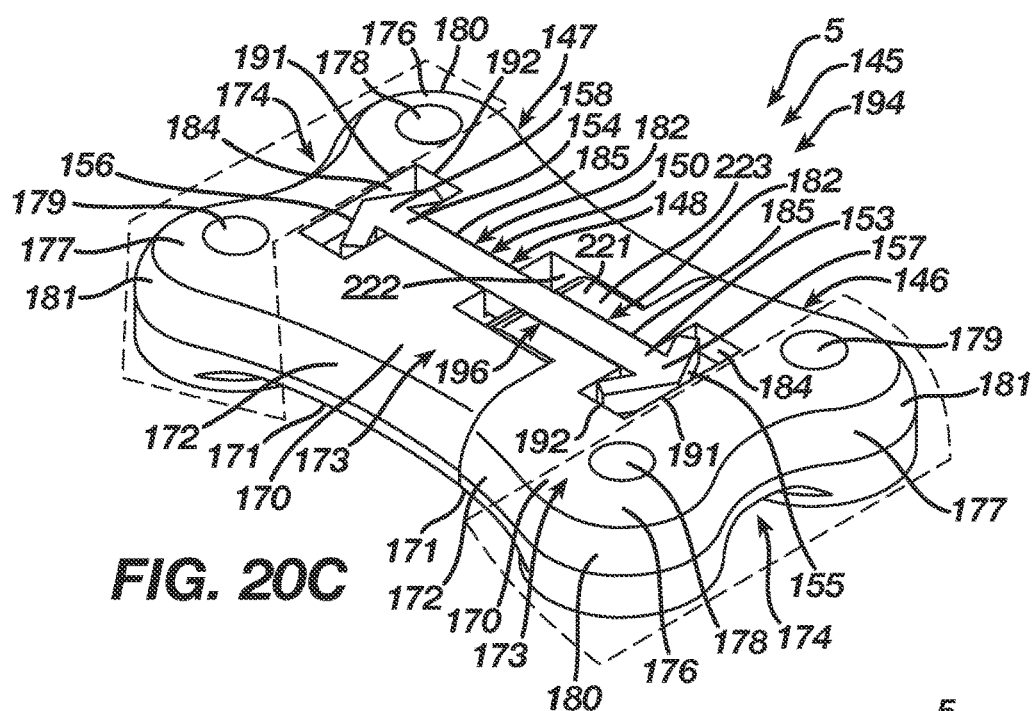
FIG. 20C is a top isometric view illustrating the orthopedic fixation system with the compression insert according to the second embodiment in the natural shape engaged with the orthopedic implant according to the second embodiment including alternative load resistance features.
Figure 20D:
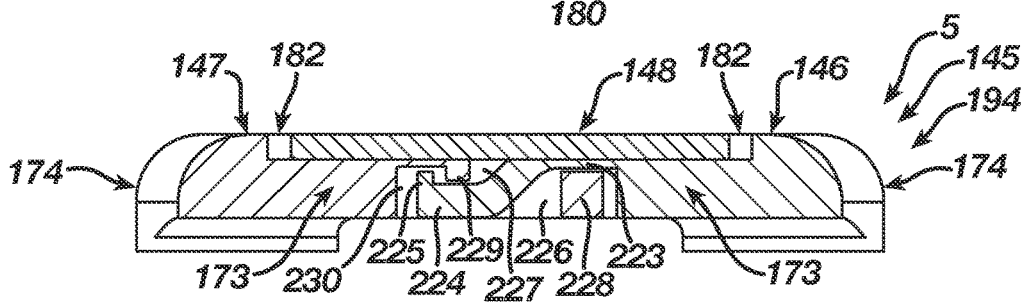
FIG. 20D is a cross-sectional view taken along lines F-F of FIG. 20B illustrating the orthopedic fixation system with the compression insert according to the second embodiment in the insertion shape engaged with the orthopedic implant according to the second embodiment including alternative load resistance features.
Figure 21A:
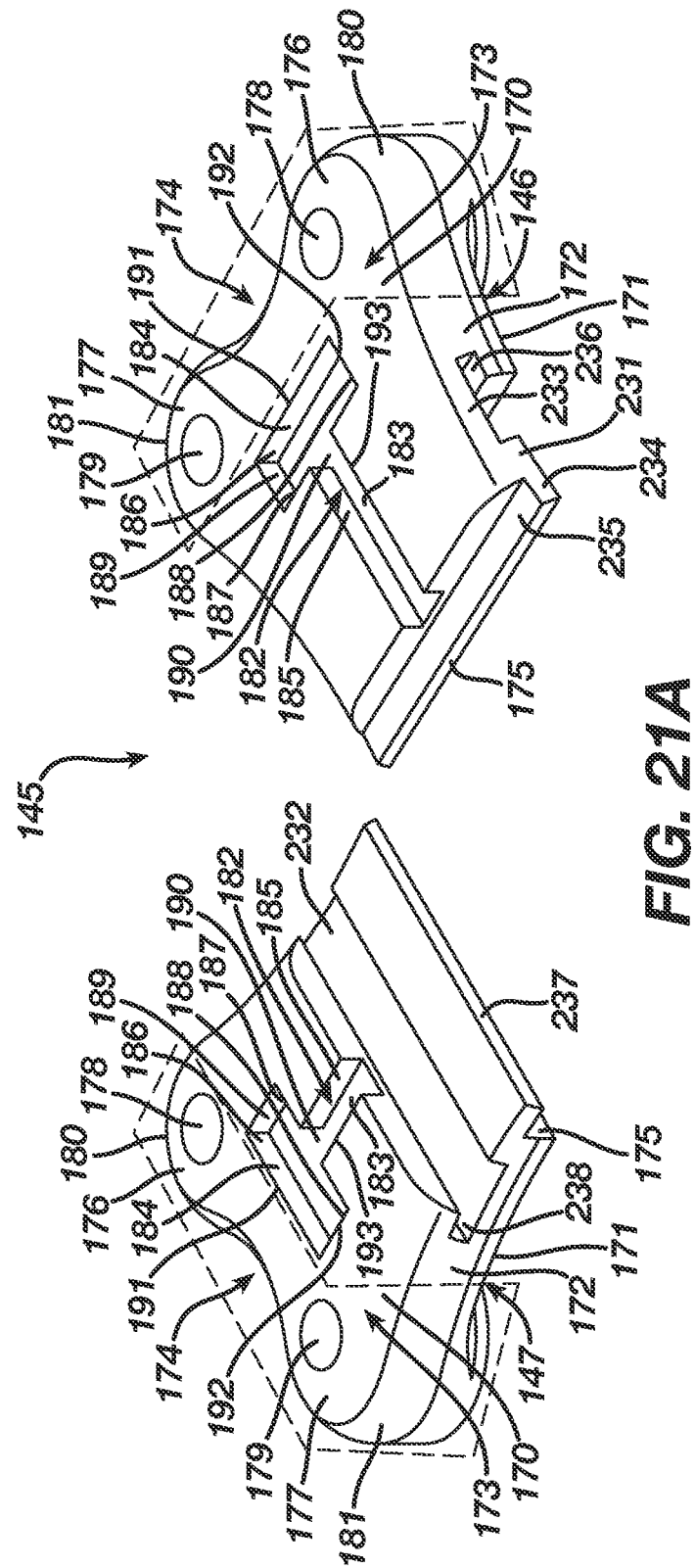
FIG. 21A is a top isometric view illustrating the orthopedic implant according to the second embodiment including alternative load resistance features.
Figure 21B:
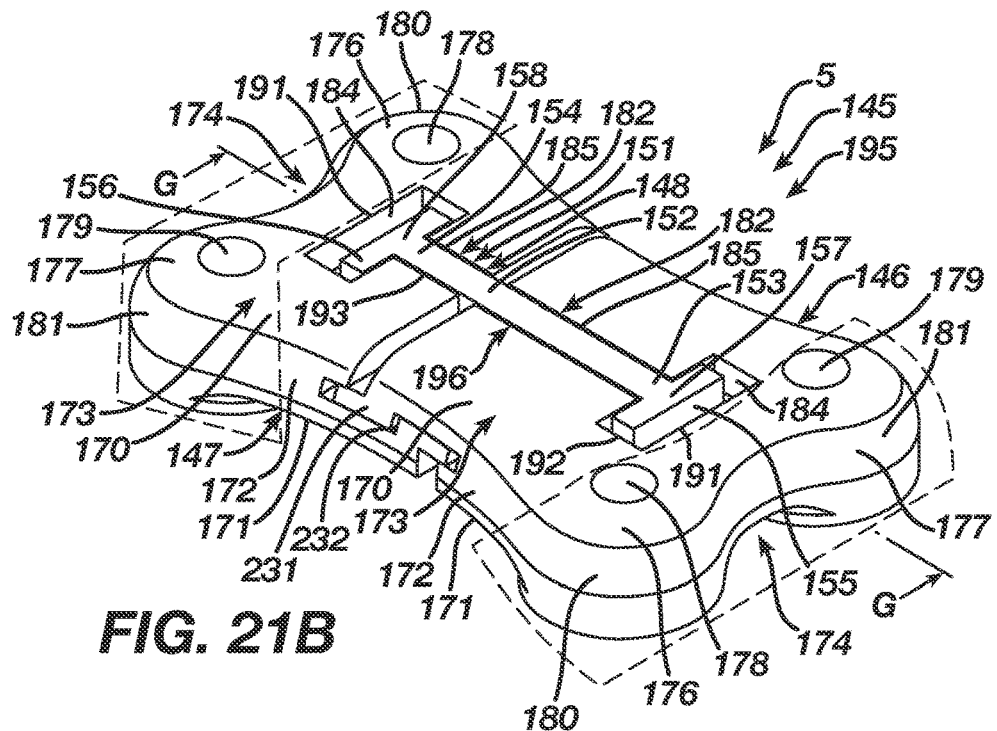
FIG. 21B is a top isometric view illustrating the orthopedic fixation system with the compression insert according to the second embodiment in the insertion shape engaged with the orthopedic implant according to the second embodiment including alternative load resistance features.
Figure 21C:
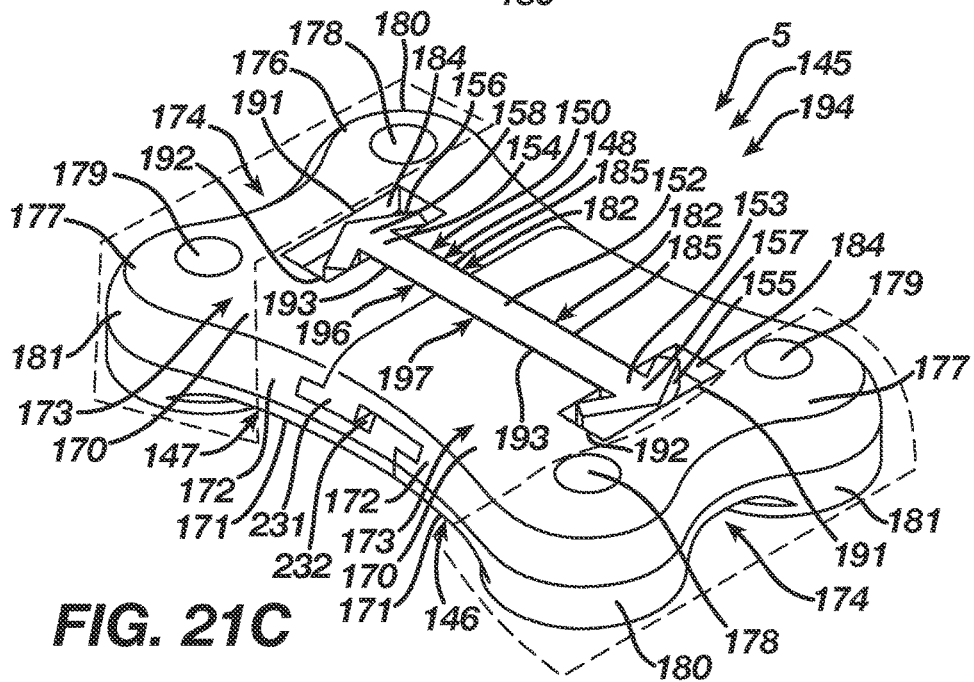
FIG. 21C is a top isometric view illustrating the orthopedic fixation system with the compression insert according to the second embodiment in the natural shape engaged with the orthopedic implant according to the second embodiment including alternative load resistance features.
Figure 21D:
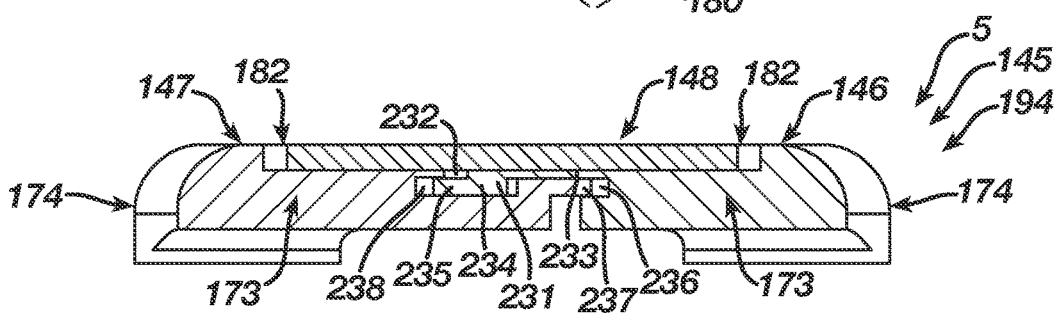
FIG. 21D is a cross-sectional view taken along lines G-G of FIG. 21B illustrating the orthopedic fixation system with the compression insert according to the second embodiment in the insertion shape engaged with the orthopedic implant according to the second embodiment including alternative load resistance features.

FIGS. 19A-19C illustrate the orthopedic implant 145 according to the second embodiment including a load resistance feature in the form of a stabilizer 215 and a cavity 216. The stabilizer 215 in the second embodiment is a three-dimensional block, whereas the cavity 216 is a cavity complementary in shape with the stabilizer 215. In the second embodiment of the orthopedic implant 145, the first plate 146 includes the stabilizer 215 projecting centrally from the front face 175, and the second plate 147 defines therein the cavity 216 centrally in the front face 175. The orthopedic implant 145 in order to incorporate therein the stabilizer 215 and the cavity 216 includes a portion of the insert slot 182 cut centrally into the upper surface of the stabilizer 215 and a portion of the insert slot 182 located centrally above the cavity 216. The stabilizer 215 includes grooves 217 cut into the upper and lower surfaces of the stabilizer 215 adjacent the sides thereof. In order to accommodate the grooves 217, the cavity 216 includes protrusions 218 extending from the upper and lower surfaces defining the cavity 216 adjacent the sides defining the cavity 216. The grooves 217 and corresponding protrusions 218 increase the surface area contact between the stabilizer 215 and the cavity 216. The stabilizer 215 and the cavity 216 are correspondingly located respectively in and the first plate 146 and the second plate 147 whereby, when the first plate 146 and the second plate 147 align at the front faces 30 thereof, the stabilizer 215 aligns with the cavity 216. In accordance therewith, the stabilizer 215 inserts into the cavity 216 during a use of the orthopedic fixation system 5 to affix bone, bones, or bone pieces. More particularly, after the first plate 146 engages with the bone, bones, or bone pieces at a first side of a fixation zone and the second plate 147 engages with the bone, bones, or bone pieces at a second side of the fixation zone, the stabilizer 215 resides in engagement with the cavity 216 such that the first plate 146 and the second plate 147 are coupled together. This coupling provides the orthopedic implant 145 with load resistance on the basis the linking of the first plate 146 with the second plate 147 prevents loads experienced by the first plate 146 and the second plate 147, such as, for example, torsional or bending forces, from altering the relative positions of the first plate 146 and the second plate 147 on the bone, bones, or bone pieces. It should be understood that the stabilizer 215 includes a length 219 and the cavity 216 includes a depth 220, whereby, when the orthopedic implant 145 resides the insertion position 195, at least a segment of the stabilizer 215 inserts into the cavity 216, and, when the orthopedic implant 145 resides the natural position 194, the stabilizer 215 substantially, completely inserts into the cavity 216. One of ordinary skill in the art will recognize the stabilizer 215 and the cavity 216 may be reversed relative to the first plate 146 and the second plate 147.

FIGS. 20A-20D illustrate the orthopedic implant 145 according to the second embodiment including an alternative load resistance feature in the form of an alternative stabilizer 221 and an alternative cavity 222 configured complementary in shape with the stabilizer 221 to receive the stabilizer 221 therein. The stabilizer 221 and the cavity 222 are substantially similar in design and operation relative to the stabilizer 215 and the cavity 216 such that, for the sake of brevity, only differences therebetween will be described herein. Moreover, one of ordinary skill in the art will recognize that the stabilizer 221 and the cavity 222 incorporate a design and load resistance function as previously set forth in the detailed description of the stabilizer 215 and the cavity 216. The stabilizer 221 includes a proximal end 223 and a distal end 224 terminating in a hook 225. The proximal end 223 and the distal end 224 lie in different planes with the proximal end 223 above the distal end 224 in order to provide the stabilizer 221 with a space 226 below the proximal end 223 and a space 227 above the distal end 224. The cavity 222 includes a protrusion 228 extending from a lower surface at a front thereof and a protrusion 229 extending from an upper surface near a rear thereof that creates a space 230. The orthopedic implant 145 in order to incorporate therein the stabilizer 221 and the cavity 222 includes a portion of the insert slot 182 cut centrally into the upper surface of the stabilizer 215 at the proximal end 223 and a portion of the insert slot 182 located centrally above the cavity 216. In order for the stabilizer 221 to fit within the cavity 222, insertion of the stabilizer 221 into the cavity 222 includes the space 226 receiving therein the protrusion 228 and the space 227 receiving therein the protrusion 229 whereby the hook 225 enters the space 230 behind the protrusion 229.

FIGS. 21A-21D illustrate the orthopedic implant 145 according to the second embodiment including an alternative load resistance feature in the form of an alternative stabilizer 231 and an alternative cavity 232 configured complementary in shape with the stabilizer 231 to receive the stabilizer 231 therein. The stabilizer 231 and the cavity 232 are substantially similar in design and operation relative to the stabilizer 215 and the cavity 216 such that, for the sake of brevity, only differences therebetween will be described herein. Moreover, one of ordinary skill in the art will recognize that the stabilizer 231 and the cavity 232 incorporate a design and load resistance function as previously set forth in the detailed description of the stabilizer 215 and the cavity 216. The stabilizer 231 includes a proximal end 233 and a distal end 234 terminating in a lip 235. The proximal end 233 defines therein a space 236 at a bottom thereof. The cavity 232 at a front thereof has a lip 237 while defining a space 238 near a rear thereof. In order for the stabilizer 231 to fit within the cavity 232, insertion of the stabilizer 231 into the cavity 232 includes the space 236 receiving therein the lip 237 and the space 238 receiving therein the lip 235.

Figure 22A:
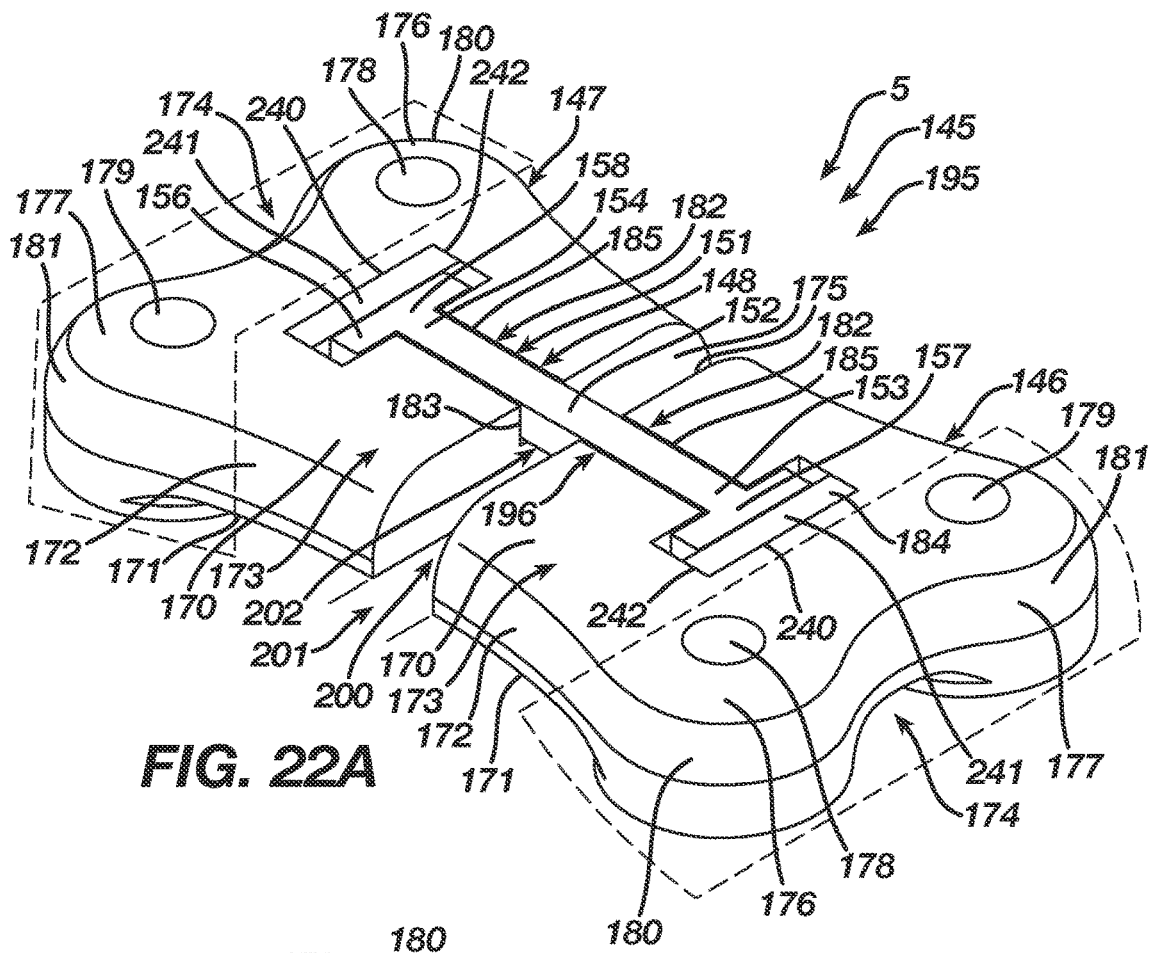
FIG. 22A is a top isometric view illustrating the orthopedic fixation system with the compression insert according to the second embodiment in the insertion shape engaged with the orthopedic implant according to the second embodiment including an insert retainer.
Figure 22B:
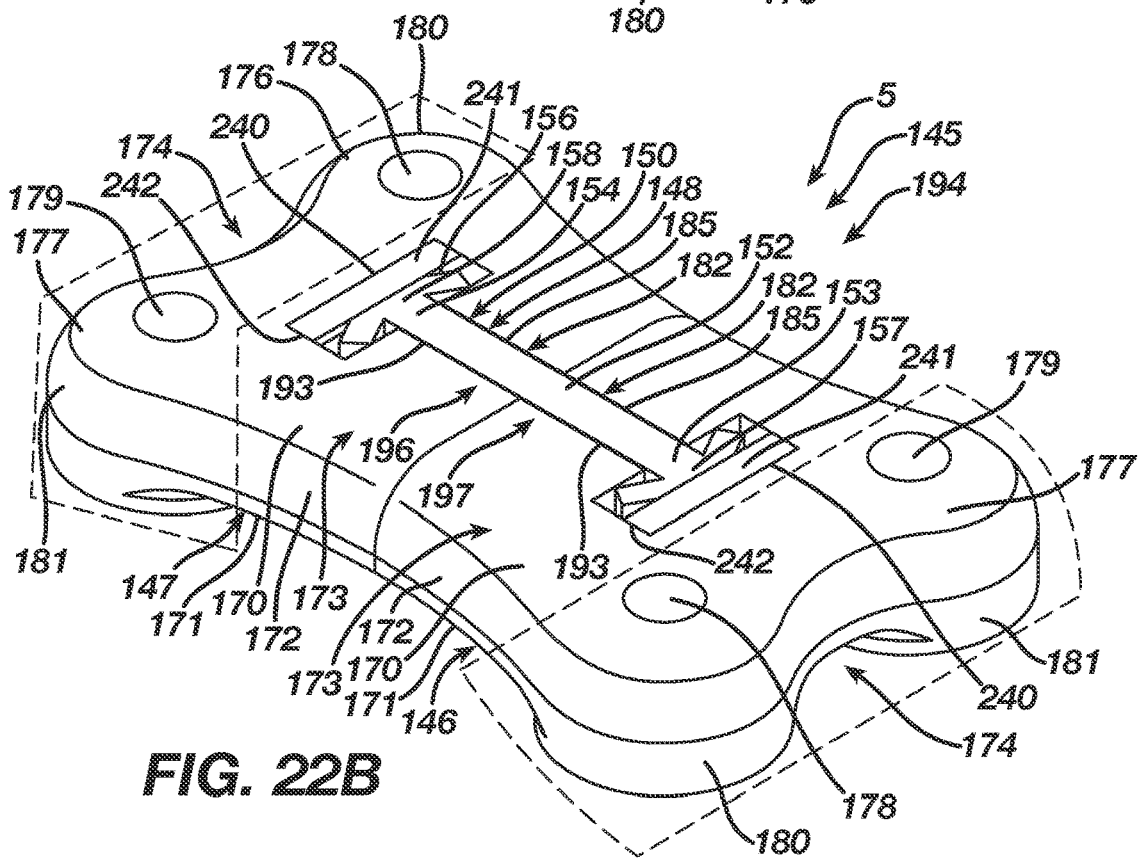
FIG. 22B is a top isometric view illustrating the orthopedic fixation system with the compression insert according to the second embodiment in the insertion shape retained by the insert retainer in engagement with the orthopedic implant according to the second embodiment.

FIGS. 22A-22B illustrate the orthopedic implant 145 according to the second embodiment including insert retainers 240 in the form of projections 241 extending from the body sections 173 of the first and second plates 146 and 147 over the chambers 184 of the insert slots 182 in the first and second plates 146 and 147. Each projection 241 begins at the upper surface 186 of the chamber 184 and extends over the chamber 184 a distance 242, whereby each projection 241 covers the chamber 184 while the chamber 184 remains configured to receive therein adjacent the lower surface 187 thereof either the first beam 155 or the second beam 156 when the compression insert 148 resides in the insertion shape 151. The projection 241 due to the distance 242 allows the compression insert 148 in the insertion shape 151 to insert into the insert retaining pathway 196 having the second overall length 202 such that the first and second beams 155 and 156 respectively abut the lower surfaces 187 of the chambers 184 in the first and second plates 146 and 147 while being spaced apart from the upper surfaces 186 of the chambers 184 in the first and second plates 146 and 147. Nevertheless, during attempted transition of the compression insert 148 from the insertion shape 151 to the natural shape 150 and the resulting attempted transition of the orthopedic implant 145 from the insertion position 195 to the natural position 194, the projections 241 due to the distances 242 block the compression insert 148 thereby retaining the compression insert 148 within the insert retaining pathway 196 because the first and second beams 155 and 156 of the compression insert 148 respectively move under the projections 241.

FIGS. 23A-24B illustrate the orthopedic fixation system 5 including an orthopedic implant 245 according to an alternative of the second embodiment and at least two compression inserts 148 according to the second embodiment. The orthopedic implant 245 includes the first plate 146, the second plate 147, and at least one expander plate 246. The expander plate 246 is similar in design and operation relative to the first and second plates 146 and 147 such that, for the sake of brevity, only differences therebetween will be described herein. Moreover, one of ordinary skill in the art will recognize that like parts of the expander plate 246 labeled with like numerals of the first and second plates 146 and 147 incorporate a design and function as previously set forth in the detailed description of the first and second plates 146 and 147. The expander plate 246 essentially comprises a first plate 146 and a second plate 147 reversed and merged at the anchoring sections 174 thereof whereby the expander plate 246 includes an anchoring section 249 located centrally in the expander plate 246. The anchoring section 249 includes openings 250-251 substantially similar to the openings 178-179, except the openings 250-251 are centrally located in the expander plate 246. In light of the expander plate 246 being configured for insertion between the first and second plates 146 and 147, the expander plate 246 includes a first body section 252 defining a first front face 254 and a second body section 253 defining a second front face 255 substantially similar to the body sections 173 and the front faces 175 of the first and second plates 146 and 147. Furthermore, the expander plate 246 includes a first insert slot 256 defining the opening 183 at the first front face 254 and a second insert slot 257 defining the opening 183 at the second front face 255, both of which are substantially similar to the insert slots 182 of the first and second plates 146 and 147.

Figure 23A:
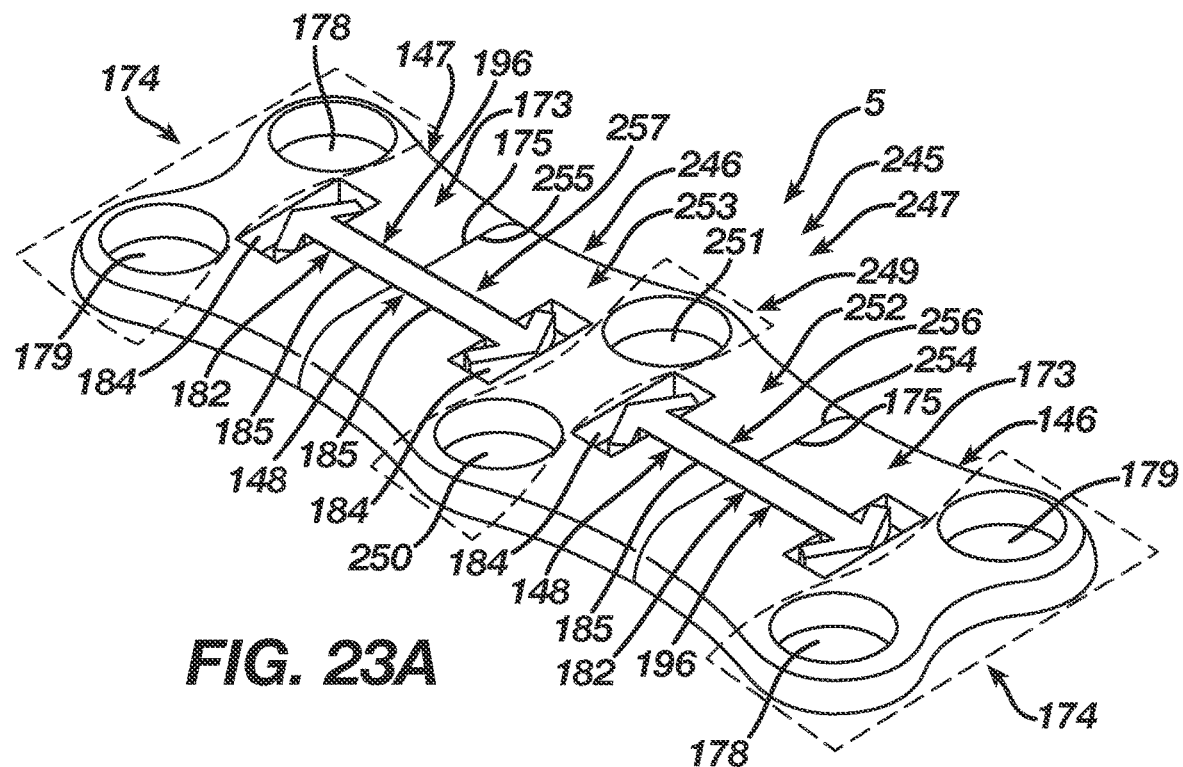
FIG. 23A is a top isometric view illustrating the orthopedic fixation system with compression inserts according to the second embodiment in the natural shape engaged with an orthopedic implant according to an alternative embodiment.
Figure 23B:
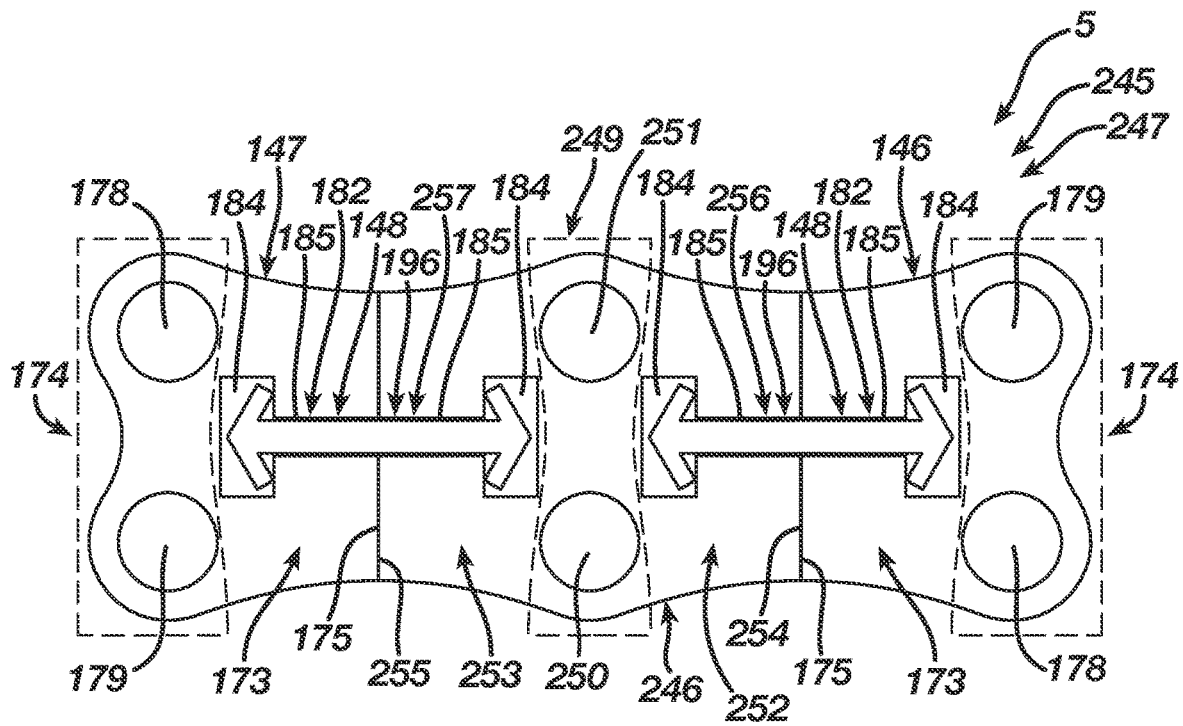
FIG. 23B is a top view illustrating the orthopedic fixation system with compression inserts according to the second embodiment in the natural shape engaged with the orthopedic implant according to the alternative embodiment.
Figure 24A:
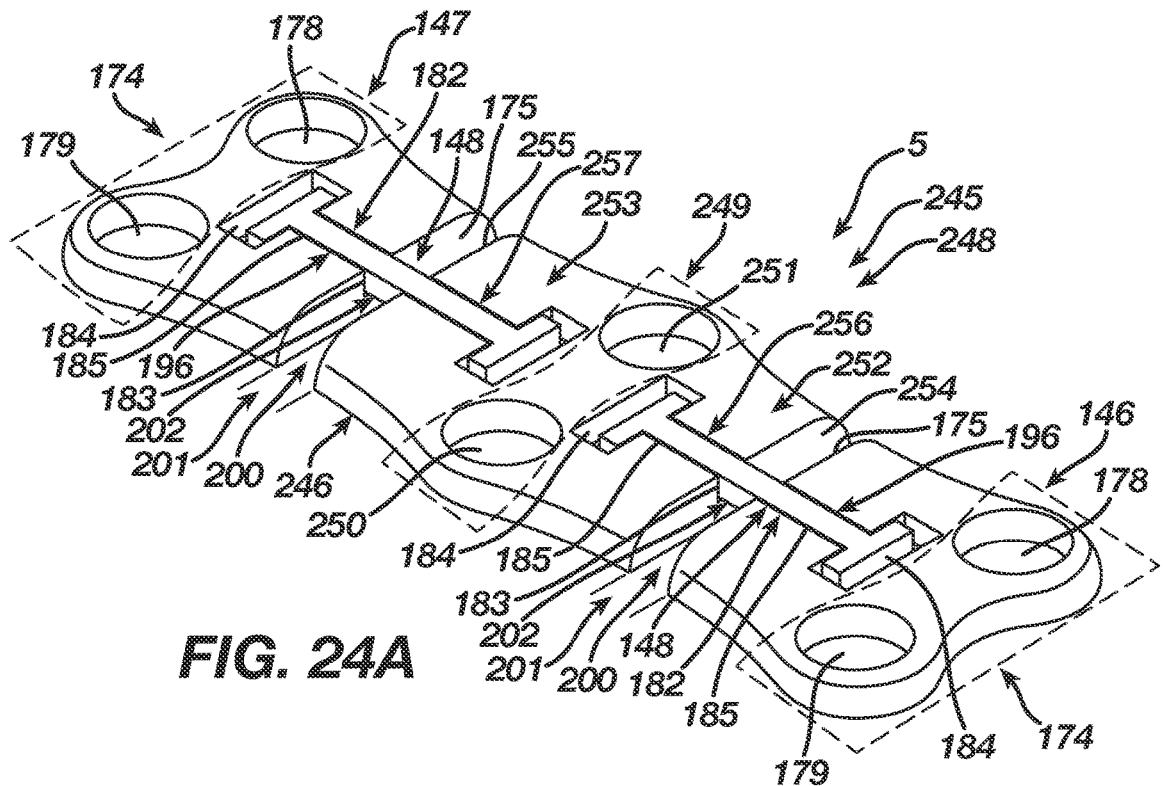
FIG. 24A is a top isometric view illustrating the orthopedic fixation system with compression inserts according to the second embodiment in the insertion shape engaged with an orthopedic implant according to an alternative embodiment.
Figure 24B:
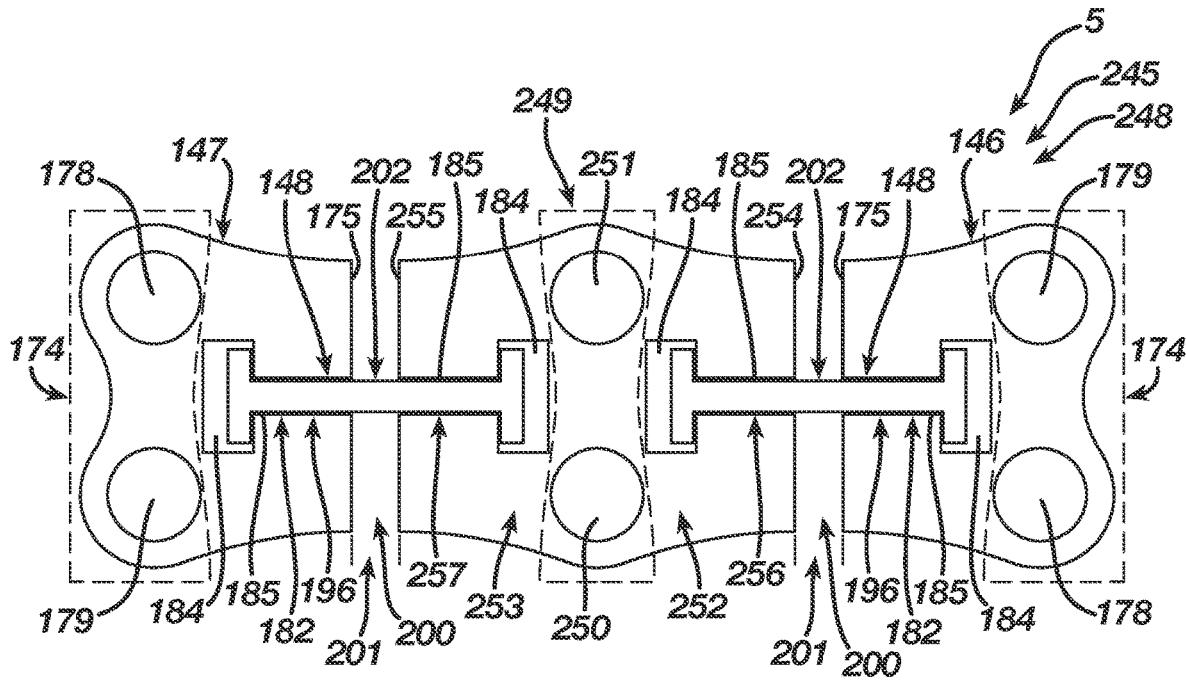
FIG. 24B is a top view illustrating the orthopedic fixation system with compression inserts according to the second embodiment in the insertion shape engaged with the orthopedic implant according to the alternative embodiment.

FIGS. 23A-23BC illustrate the orthopedic implant 245 according to the alternative of the second embodiment residing in a natural position 247 configured for receipt therein of the compression inserts 148 when transitioned to the natural shape 150, whereas FIGS. 24A-24B illustrate the orthopedic implant 245 according to the alternative of the second embodiment residing in an insertion position 248 configured for receipt therein of the compression inserts 148 when deformed into the insertion shape 151. When utilizing the orthopedic fixation system 5 to affix bone, bones, or bone pieces and promote a healing thereof, the orthopedic implant 245 while located in the insertion position 248 engages with the bone, bones, or bone pieces across first and second fixation zones thereof. More particularly, the first plate 146 engages with the bone, bones, or bone pieces at a first side of the first fixation zone, the expander plate 246 engages with the bone, bones, or bone pieces at a second side of the first fixation zone and a first side of the second fixation zone, and the second plate 147 engages with the bone, bones, or bone pieces at a second side of the second fixation zone. The first plate 146 and the expander plate 246, upon engagement with the bone, bones, or bone pieces, are aligned at the front face 175 and the first front face 252 while being spaced apart across the first fixation zone by the expansion 200 having the width 201 such that the orthopedic implant 245 via the first plate 146 and the expander plate 246 and the expansion 200 thereof includes the insert retaining pathway 196 having the second overall length 202. The second plate 147 and the expander plate 246, upon engagement with the bone, bones, or bone pieces, are aligned at the front face 175 and the second front face 253 while being spaced apart across the second fixation zone by the expansion 200 having the width 201 such that the orthopedic implant 245 via the second plate 147 and the expander plate 246 and the expansion 200 thereof includes the insert retaining pathway 196 having the second overall length 202. The compression inserts 148, which have been deformed to the insertion shape 151 whereby the compression inserts 148 store energy, insert into the insert retaining pathways 196. The insert retaining pathway 196 on account of the second overall length 202 receives the compression insert 148 therein with the first beam 155 thereof abutting the lower surface 187 of the chamber 184 in the first plate 146 while being spaced apart from the upper surface 186 of the chamber 184 in the first plate 146 and the second beam 156 thereof abutting the lower surface 187 of the chamber 184 in the expander plate 246 while being spaced apart from the upper surface 186 of the chamber 184 in the expander plate 246. The insert retaining pathway 196 on account of the second overall length 202 receives the compression insert 148 therein with the first beam 155 thereof abutting the lower surface 187 of the chamber 184 in the second plate 147 while being spaced apart from the upper surface 186 of the chamber 184 in the second plate 147 and the second beam 156 thereof abutting the lower surface 187 of the chamber 184 in the expander plate 246 while being spaced apart from the upper surface 186 of the chamber 184 in the expander plate 246. Upon insertion into the insert retaining pathways 196 including a release of any mechanical constraint, the compression inserts 148 attempts to transition from the insertion shape 151 to the natural shape 150 such that the compression inserts 148 engage with the chambers 184 of the first plate 146, the expander plate 246, and the second plate 147 at the lower surfaces 187 thereof, thereby ensuring the compression insert 148 remains within the first plate 146, the expander plate 246, and the second plate 147 and thus the orthopedic implant 245. Moreover, the compression inserts 148, due to their attempted transition from the insertion shape 151 to the natural shape 150, deliver the energy stored therein to the first plate 146, the expander plate 246, and the second plate 147 at the lower surfaces 187 of the chambers 182 thereof and thus the orthopedic implant 245, resulting in the orthopedic implant 245 attempting to move from the insertion position 248, which includes the expansion 200, to the natural position 247. In accordance therewith, the orthopedic implant 245 continuously compresses the bone, bones, or bone pieces at the first and second fixation zones thereof whereby the orthopedic fixation system 5 affixes the bone, bones, or bone pieces in order to promote a fusion and a healing thereof. One of ordinary skill in the art will recognize that the sizes of the first plate 146, the second plate 147, the expander plate 246, the insert slots 182 and 254-255 including the chambers 184 and the channels 185, the expansion 200, and the compression inserts 148 are dependent upon the size and configuration of the bone, bones, or bone pieces requiring fixation.

FIGS. 25A-26C illustrate the orthopedic fixation system 5 including a compression insert 258 alternative to the compression insert 148 of the second embodiment and an orthopedic implant 260 alternative to the orthopedic implant 145 of the second embodiment. The compression insert 258 is substantially similar in design and operation relative to the compression insert 148 according to the second embodiment such that, for the sake of brevity, only differences therebetween will be described herein. Moreover, one of ordinary skill in the art will recognize that like parts of the compression insert 258 labeled with like numerals of the compression insert 148 incorporate a design and function as previously set forth in the detailed description of the compression insert 148 according to the second embodiment. Likewise, the orthopedic implant 260 is substantially similar in design and operation relative to the orthopedic implant 145 according to the second embodiment such that, for the sake of brevity, only differences therebetween will be described herein. Moreover, one of ordinary skill in the art will recognize that like parts of the orthopedic implant 260 labeled with like numerals of the orthopedic implant 145 incorporate a design and function as previously set forth in the detailed description of the orthopedic implant 145 according to the second embodiment.

Figure 25A:
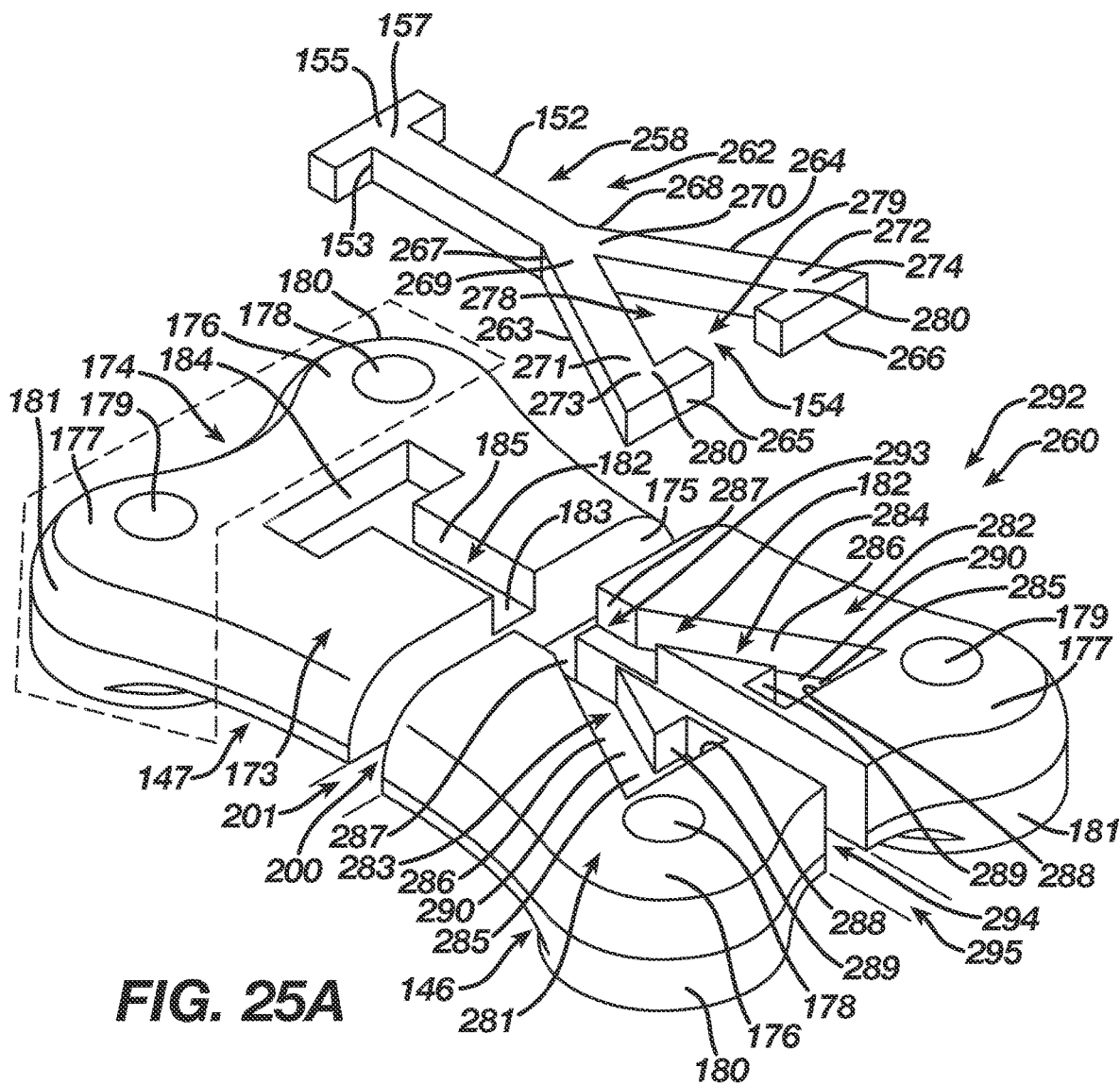
FIG. 25A is a top isometric view illustrating the orthopedic fixation system with a compression insert according to an alternative embodiment in an insertion shape disengaged from an orthopedic implant according to an alternative embodiment.
Figure 25B:
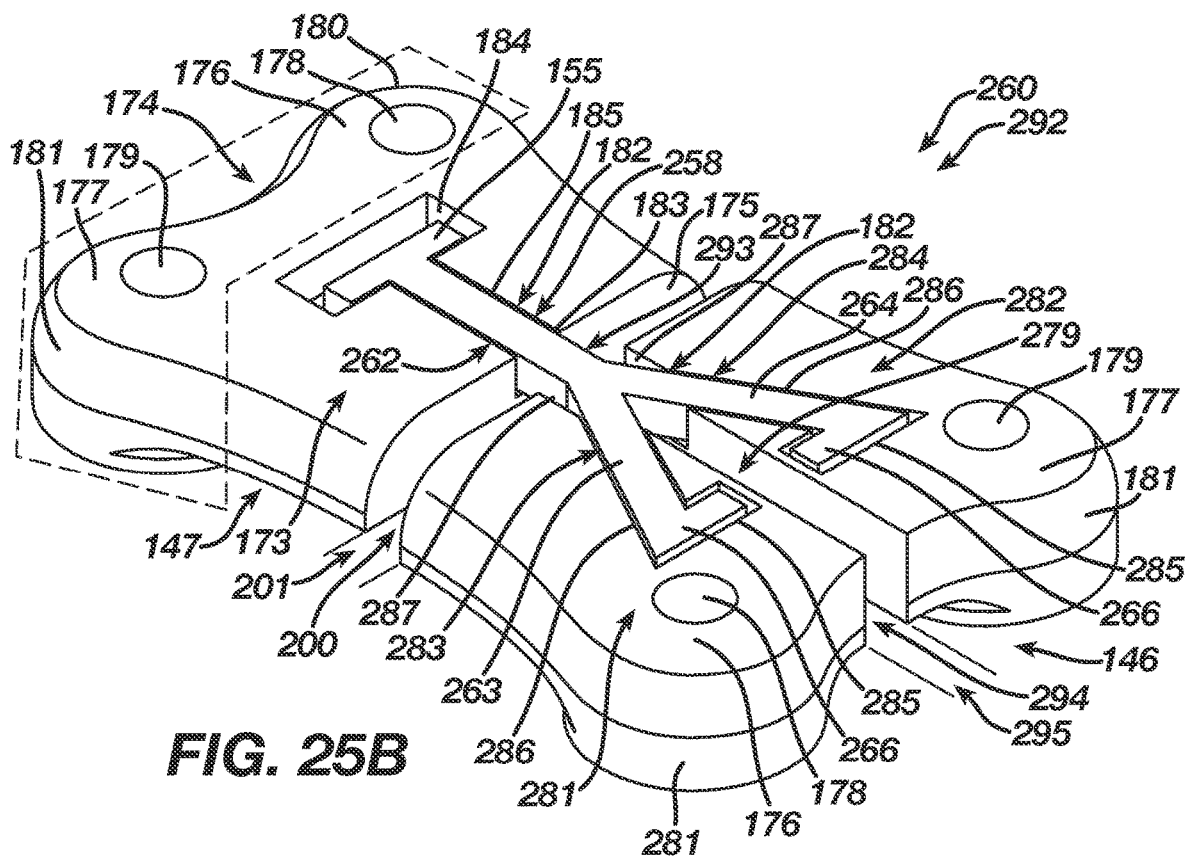
FIG. 25B is a top isometric view illustrating the orthopedic fixation system with the compression insert according to the alternative embodiment in the insertion shape engaged with the orthopedic implant according to the alternative embodiment.
Figure 25C:
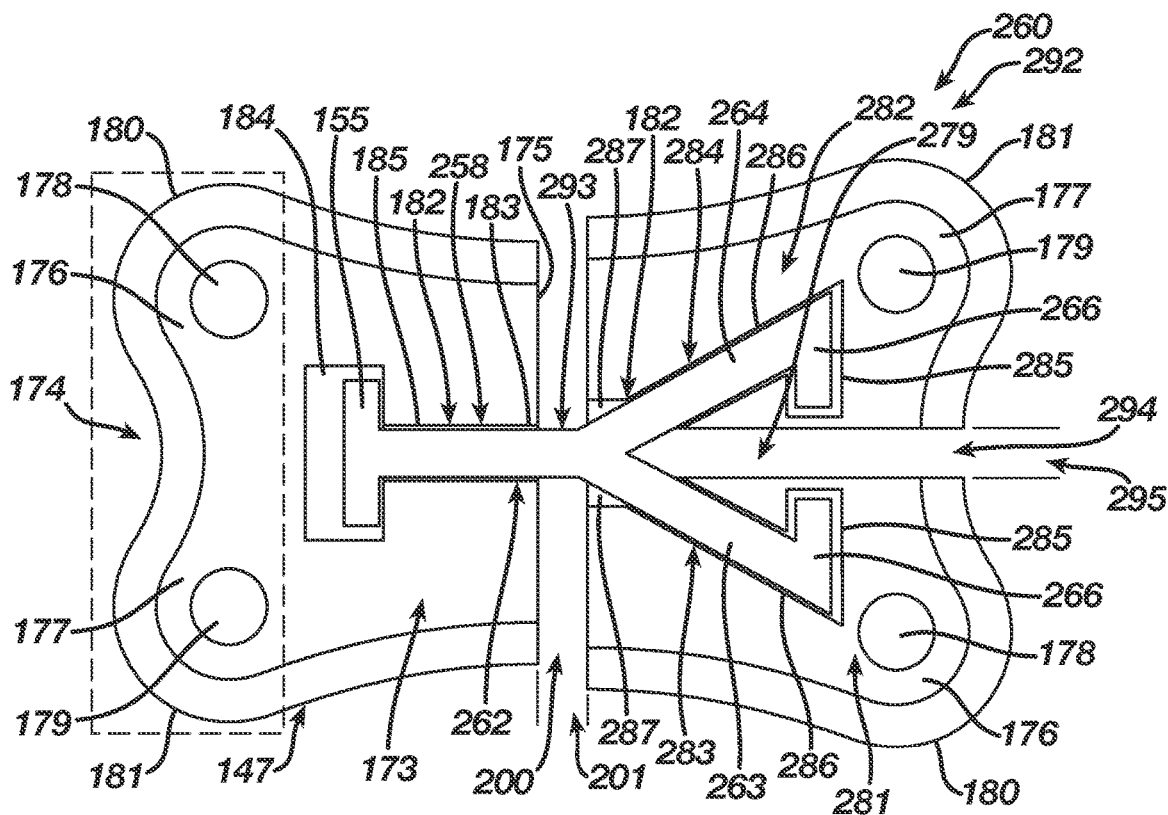
FIG. 25C is a top view illustrating the orthopedic fixation system with the compression insert according to the alternative embodiment in the insertion shape engaged with the orthopedic implant according to the alternative embodiment.
Figure 26A:
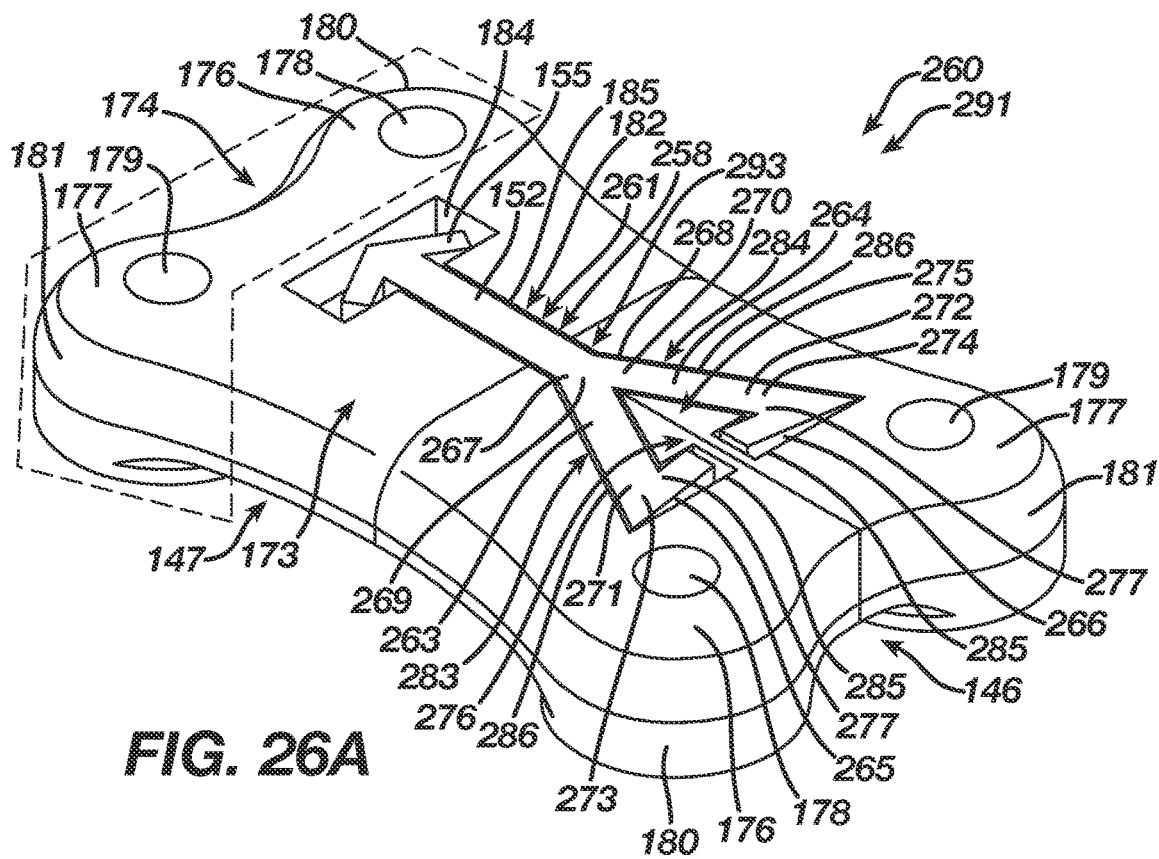
FIG. 26A is a top isometric view illustrating the orthopedic fixation system with the compression insert according to the alternative embodiment in the natural shape engaged with the orthopedic implant according to the alternative embodiment.
Figure 26B:
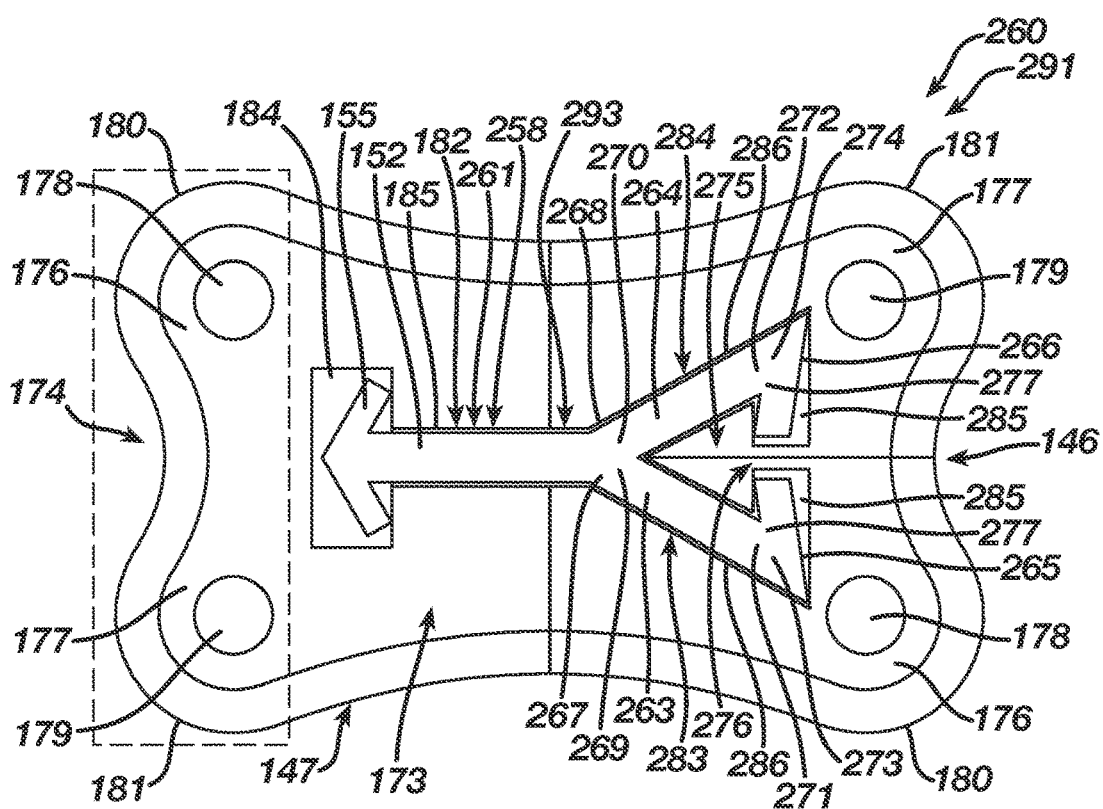
FIG. 26B is a top isometric view illustrating the orthopedic fixation system with the compression insert according to the alternative embodiment in the natural shape engaged with the orthopedic implant according to the alternative embodiment.
Figure 26C:
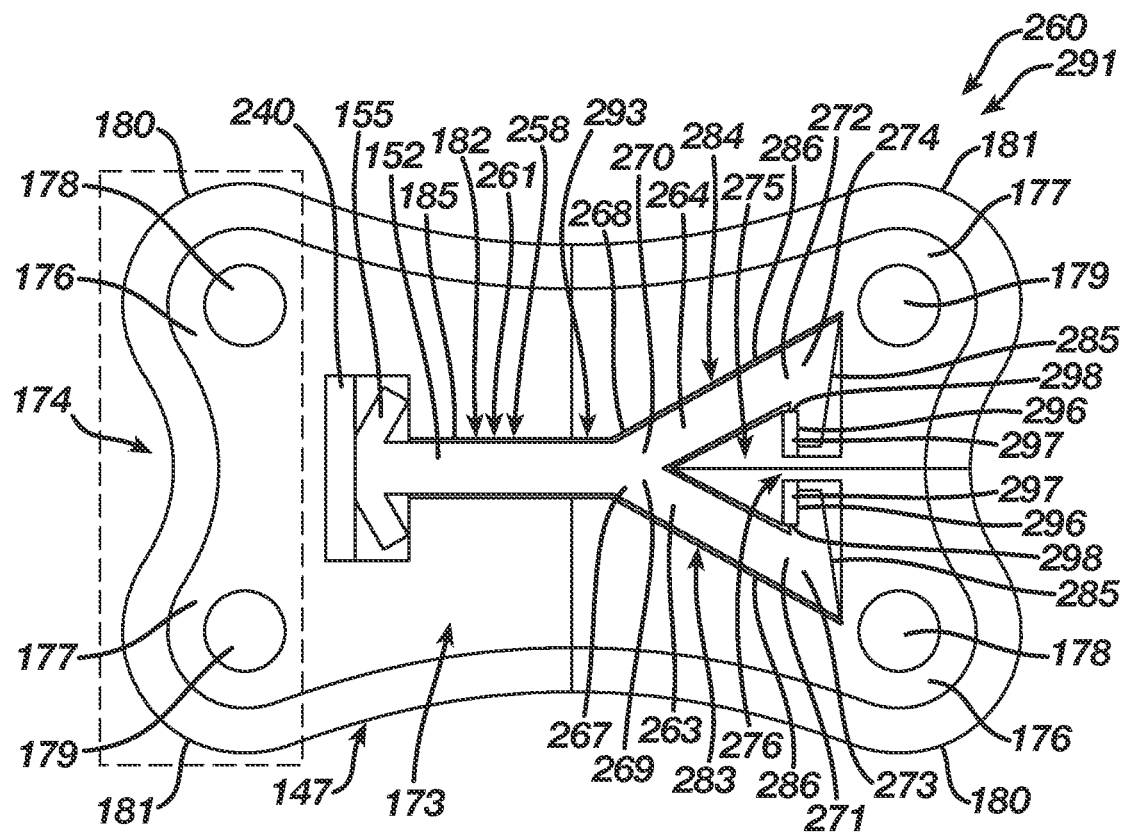
FIG. 26C is a top isometric view illustrating the orthopedic fixation system with the compression insert according to the alternative embodiment in the natural shape retained by an insert retainer in engagement with the orthopedic implant according to the alternative embodiment.
Figure 27A:
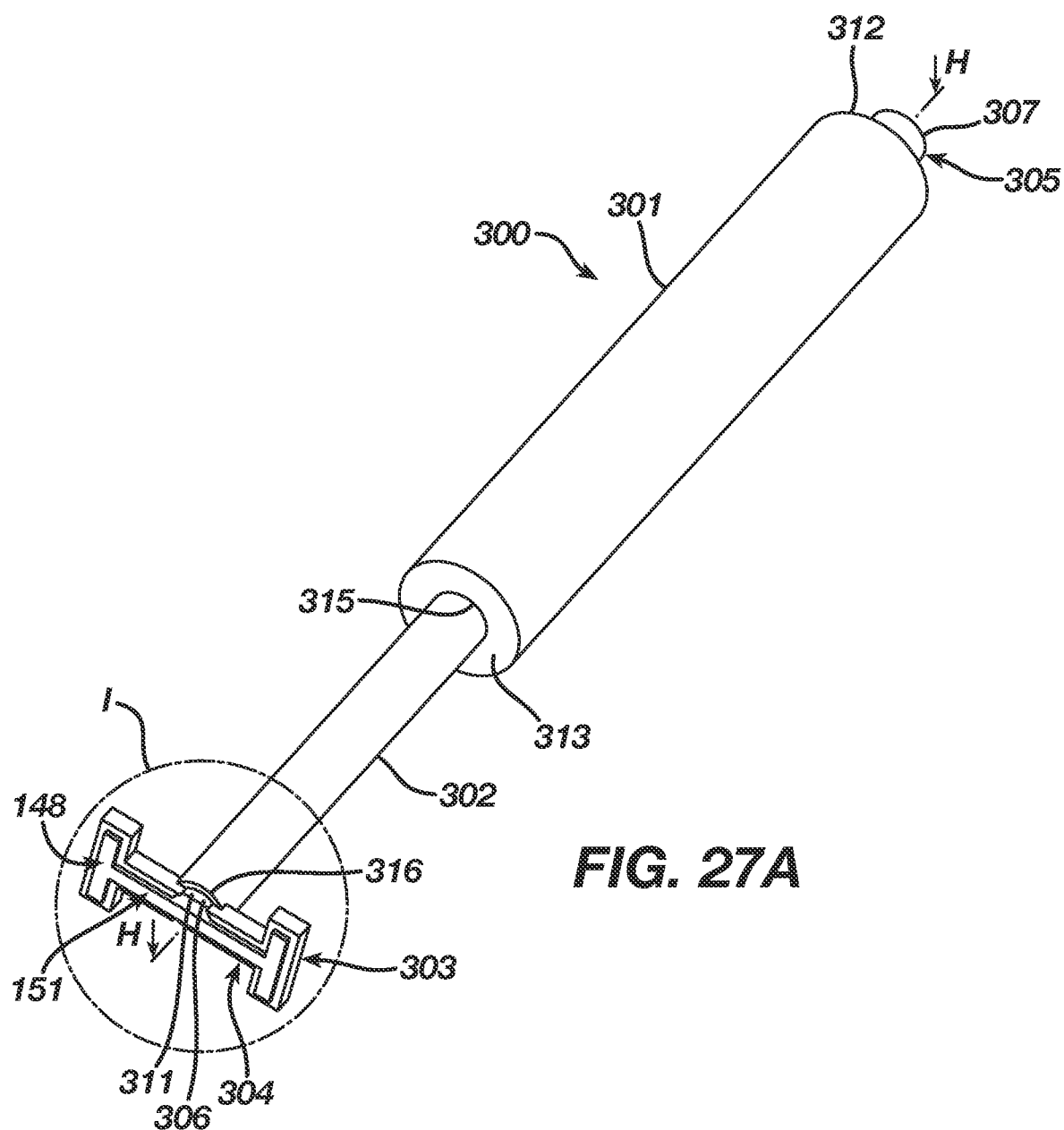
FIG. 27A is an isometric view illustrating an insert delivery device for the compression insert according to the second embodiment.
Figure 27B:
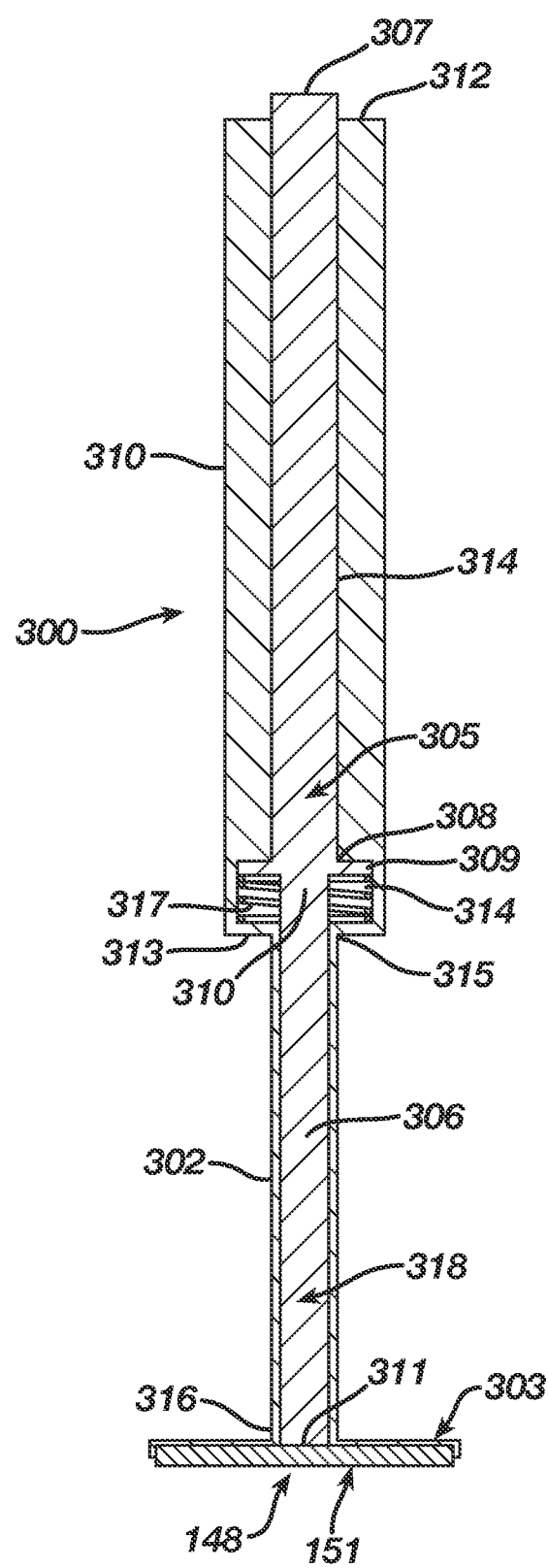
FIG. 27B is a cross-sectional view taken along lines H-H of FIG. 27A illustrating the insert delivery device for the compression insert according to the second embodiment.
Figure 27C:
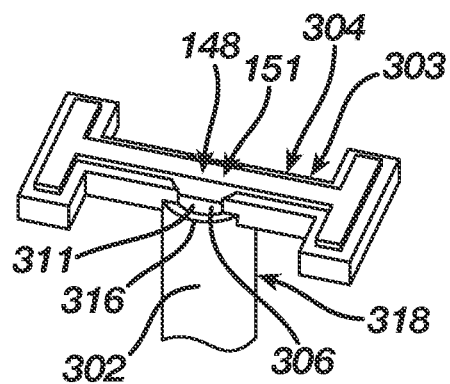
FIG. 27C is an enlarged isometric view taken along circle I of FIG. 27A illustrating the insert delivery device for the compression insert according to the second embodiment.
Figure 27D:
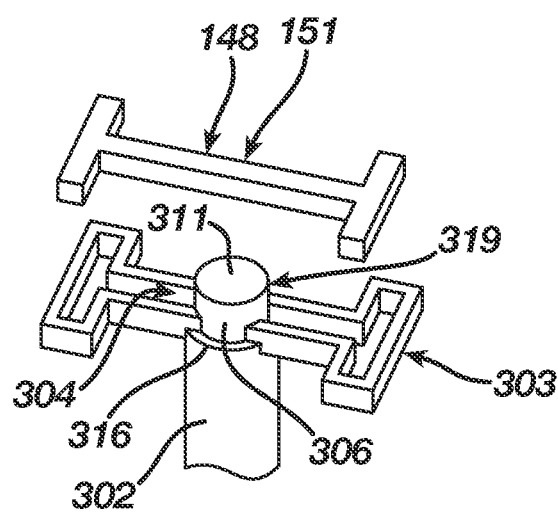
FIG. 27D is an enlarged isometric view illustrating the insert delivery device for the compression insert according to the second embodiment.

The compression insert 258 according to the alternative of the second embodiment includes a natural shape 261 as illustrated in FIGS. 26A-26C and an insertion shape 262 as illustrated in FIGS. 25A-25C. The compression insert 258 similar to the compression insert 148 includes the shaft 152 terminating at the first end 153 in the first beam 155 positioned transverse relative to the shaft 152. Nevertheless, the shaft 152 in the alternative of the second embodiment divides to provide at the second end 154 a first shaft segment 263 terminating in a first hook 265 extending interior relative to the first shaft segment 263 and a second shaft segment 264 terminating in a second hook 266 extending interior relative to the second shaft segment 265. While the first beam 155 adjacent the first end 153 includes the first transition section 157, the first shaft segment 263 at a first end 267 includes a first shaft segment transition section 269 and the second shaft segment 264 at a first end 268 includes a second shaft segment transition section 270. Similarly, the first hook 265 adjacent a second end 271 of the first shaft segment 263 includes a first hook transition section 273, and the second hook 266 adjacent a second end 272 of the second shaft segment 264 includes a second hook transition section 274. The first transition section 157, the first shaft segment transition section 269, the second shaft segment transition section 270, the first hook transition section 273, and the second hook transition section 274 in the alternative to the second embodiment facilitate transition of the compression insert 258 between the natural shape 261 and the insertion shape 262. The first transition section 157, the first shaft segment transition section 269, the second shaft segment transition section 270, the first hook transition section 273, and the second hook transition section 274 further facilitate engagement of the compression insert 258 with the orthopedic implant 260.

The regular inherent shape of the compression insert 258, as illustrated in FIGS. 26A-26B, is the natural shape 261 where the first transition section 157 identical to compression insert 148 contracts the first beam 155 such that the first beam 155 includes the first width 160 and the first height 161 while being spaced apart at the first distance 162. Moreover, the first shaft segment transition section 269 and the second shaft segment transition section 270 respectively locate the compression insert 258 in the natural shape 261, which consists of a closed position 275 whereby the first shaft segment transition section 269 and the second shaft segment transition section 270 respectively contract the first shaft segment 263 and the second shaft segment 264 such that the first shaft segment 263 and the second shaft segment 264 are spaced apart at a first distance 276. In addition, the first hook transition section 273 and the second hook transition section 274 respectively locate the compression insert 258 in the natural shape 261, which consists of the closed position 275 whereby the first hook transition section 273 and the second hook transition section 274 respectively contract the first hook 265 and the second hook 266 such that the first hook 265 and the second hook 266 reside at a first angle 277. Nevertheless, as illustrated in Figures the compression insert 258 is deformable under the action of superelasticity or temperature dependent shape memory to the insertion shape 262 where the first transition section 157 identical to compression insert 148 deforms to store energy while also expanding the first beam 155 such that the first beam 155 includes the second width 164 that is greater than the first width 164 and the second height 165 that is less than the first height 161 while being spaced apart at the second distance 166 that is greater than the first distance 162. Moreover, the first shaft segment transition section 269 and the second shaft segment transition section 270 respectively locate the compression insert 258 in the insertion shape 262, which consists of an open position 278 whereby the first shaft segment transition section 269 and the second shaft segment transition section 270 respectively expand the first shaft segment 263 and the second shaft segment 264 such that the first shaft segment 263 and the second shaft segment 264 are spaced apart at a second distance 279 that is greater than the first distance 276. In addition, the first hook transition section 273 and the second hook transition section 274 respectively locate the compression insert 258 in the natural shape 261, which consists of the open position 278 whereby the first hook transition section 273 and the second hook transition section 274 respectively expand the first hook 265 and the second hook 266 such that the first hook 265 and the second hook 266 reside at a second angle 280 that is greater than the first angle 277. Since the insertion shape 262 is not the regular inherent shape of the compression insert 258, the orthopedic implant 260, when coupled with the compression insert 258, typically is mechanically constrained using an implant retainer whereby the implant retainer holds the orthopedic implant 260 such that the compression insert 258 is prevented from returning to the natural shape 261 thereof. Alternatively, the compression insert 258 may be mechanically constrained using an insert retainer that maintains the compression insert 258 in the insertion shape 262 until an engagement of the compression insert 258 with the orthopedic implant 260 and a release of the compression insert 258 from the insert retainer.

The orthopedic implant 145 in the second embodiment includes the first plate 146 and the second plate 147 whereby the first plate 146 and the second plate 147 are unitary. Alternatively, the orthopedic implant 260 includes the first plate 146 or the second plate 147 or both the first plate 146 and the second plate 147 divided into plate segments. In accordance therewith, the first plate 146 as illustrated in FIGS. 25A-26B includes the anchoring member 176 divided from the anchoring member 177 to form a first plate segment 281 and a second plate segment 282. Although the first plate 146 divides into the first plate segment 281 and the second plate segment 282, the first plate 146, when the first and second plate segments 281 and 282 are located directly adjacent, includes the front face 175. When the anchoring member 176 is divided from the anchoring member 177, the insert slot 182 is reconfigured into a first insert slot segment 283 in the first plate segment 281 and a second insert slot segment 284 in the second plate segment 282. The first insert slot segment 283 and the second insert slot segment 284 each include a hook chamber 285 communicating with a shaft segment channel 286 defining an opening 287 at the front face 175. Each hook chamber 285 includes an upper surface 288 and a lower surface 289 and further an opening 290 in the lower surface 289 that connects the hook chamber 286 with the shaft segment channel 286 opposite from the opening 287 therein. The shaft segment channel 286 in the first plate segment 281 is configured to receive therein at the opening 287 a portion of the shaft 152 and further the first shaft segment 263 such that the hook chamber 285 receives therein the first hook 265. Similarly, the shaft segment channel 286 in the second plate segment 282 is configured to receive therein at the opening 287 a portion of the shaft 152 and further the second shaft segment 264 such that the hook chamber 285 receives therein the second hook 266. The hook chamber 285 includes dimensions that allow the hook chamber 285 to receive therein one of the first and second hooks 265 and 266 when residing at the second angle 280 while further allowing a transition of the first and second hooks 265 and 266 from the second angle 280 to the first angle 277.

FIGS. 26A-26B illustrate the orthopedic implant 260 residing in a natural position 291 configured for receipt therein of the compression insert 258 when transitioned to the natural shape 261. The orthopedic implant 260 in the natural position 291 includes the first plate 146 at the front face 175 thereof facing the second plate 147 at the front face 175 thereof such that the front faces 175 are aligned while being located directly adjacent. When the first plate 146 and the second plate 147 are aligned with the front faces 175 thereof being located directly adjacent, the first and second plate segments 281 and 282 of the first plate 146 are located directly adjacent in order for the first plate and second plates 146 and 147 to define an insert retaining pathway 293 configured to receive therein the compression insert 258 in the natural shape 261. More particularly, the first and second insert slot segments 283 align to receive therein the first and second shaft segments 263 and 264 contracted to reside at the first distance 276 and the first and second hooks 265 and 266 contracted to reside at the first angle 277 whereby the first and second hooks 265 and 266 engage the lower surface 289 of respective hook chambers 285. The insert slot 182 of the second plate 147 receives therein the shaft 152 and the first beam 155 as previously described with respect to the orthopedic implant 145. The insert retaining pathway 293 holds therein the compression insert 258 engaged with the first and second plate segments 281 and 282 of the first plate 146 of the first plate 146 and the body section 173 of the second plate 147, thereby ensuring the compression insert 258 remains within the first plate 146 and the second plate 147 and thus the orthopedic implant 260.

FIGS. 25A-25C illustrate the orthopedic implant 260 residing in an insertion position 292 configured for receipt therein of the compression insert 258 when deformed into the insertion shape 262. The orthopedic implant 260 in the insertion position 292 includes the first plate 146 at the front face 175 thereof facing the second plate 147 at the front face 175 thereof such that the second plate 147 at the front face 175 thereof is spaced apart from the first and second plate segments 281 and 282 of the first plate 146 to produce the expansion 200 having the width 201. In addition, the first and second plate segments 281 and 282 are spaced apart by an expansion 294 having a width 295. When the second plate 147 is spaced apart from the first and second plate segments 281 and 282 to produce the expansion 200 and the first and second plate segments 281 and 282 are spaced apart by the expansion 294, the insert retaining pathway 293, which has been enlarged by the expansions 200 and 294, is configured to receive therein the compression insert 258 in the insertion shape 262. More particularly, the first and second insert slot segments 283 and 284, which are spaced apart by the expansion 294, receive in respective shaft segment channels 286 the first and second shaft segments 263 and 264 expanded to reside at the second distance 279. Moreover, the first and second insert slot segments 283 and 284 receive in respective hook chambers 285 the first and second hooks 265 and 266 expanded to reside at the second angle 280 whereby the first and second hooks 265 and 266 are separated from the lower surface 289 of respective hook chambers 285. Although the first and second insert slot segments 283 and 284 are spaced apart from the second plate 147 by the expansion 200, the hook chambers 285 receive therein the first and second hooks 265 and 266 due to the dimensions thereof being sufficient to allow transition of the first and second hooks 265 and 266 between the first and second angles 277 and 280. The insert slot 182 of the second plate 147 receives therein the shaft 152 and the first beam 155 as previously described with respect to the orthopedic implant 145. The enlarging of the insert retaining pathway 293 by the expansions 200 and 294 permits the insert retaining pathway 293 to receive therein the compression insert 258 expanded to reside in the insertion shape 262.

When utilizing the orthopedic fixation system 5 to affix bone, bones, or bone pieces and promote a healing thereof, the orthopedic implant 260 while located in the insertion position 292 engages with the bone, bones, or bone pieces across a fixation zone thereof. More particularly, the second plate 147 engages with the bone, bones, or bone pieces at a first side of the fixation zone, whereas the first and second plate segments 281 and 282 of the first plate 146 engage with the bone, bones, or bone pieces at additional sides of the fixation zone. The first and second plate segments 281 and 282, upon engagement with the bone, bones, or bone pieces, are aligned while being spaced apart across the additional sides of the fixation zone by the expansion 294 having the width 295. The second plate 147, upon engagement with the bone, bones, or bone pieces, is aligned with the first plate 146 while being spaced apart therefrom across the first side of the fixation zone by the expansion 200 having the width 201. The orthopedic implant 260, therefore, via the first plate 146 and the second plate 147 and the expansions 200 and 294 thereof, includes the insert retaining pathway 293 enlarged to receive therein the compression insert 258 in the insertion shape 262. The compression insert 258, which has been deformed to the insertion shape 262 whereby the compression insert 258 stores energy, inserts into the insert retaining pathway 293. Upon insertion into the insert retaining pathway 293 including a release of any mechanical constraint, the compression insert 258 attempts to transition from the insertion shape 262 to the natural shape 261 such that the compression insert 258 engages with the body section 173 of the second plate 147 at the chamber 184 of the insert slot 182 and the first and second plate segments 281 and 282 of the first plate 146 at the shaft segment channels 286 and the hook chambers 285 of the first and second insert slot segments 283 and 284, thereby ensuring the compression insert 258 remains within the first plate 146 and the second plate 147 and thus the orthopedic implant 260. Moreover, the compression insert 258, due to its attempted transition from the insertion shape 262 to the natural shape 261, delivers the energy stored therein to the first and second plate segments 281 and 282 of the first plate 146 and the second plate 147 and thus the orthopedic implant 260, resulting in the orthopedic implant 260 attempting to move from the insertion position 292, which includes the expansions 200 and 294, to the natural position 291. In accordance therewith, the orthopedic implant 260 continuously compresses the bone, bones, or bone pieces at the fixation zone thereof whereby the orthopedic fixation system 5 affixes the bone, bones, or bone pieces in order to promote a fusion and a healing thereof. One of ordinary skill in the art will recognize that the sizes of the first and second plate segments 281 and 282 of the first plate 146, the second plate 147, the insert slot 182, the first and second insert slot segments 283 and 284, the expansions 200 and 294, and the compression insert 258 are dependent upon the size and configuration of the bone, bones, or bone pieces requiring fixation. The orthopedic implant 260 accordingly provides improvements in orthopedic surgeries in that the first and second plate segments 281 and 282 produce compression in comminuted pole fractures of the patella as well as continuous radial compression of multiple bones or bone pieces resulting in a drawing of the multiple bones or bone pieces into a central point until a fusion thereof.

FIG. 26C illustrates the orthopedic implant 260 alternative to the orthopedic implant 145 of the second embodiment including the insert retainer 240 as previously described and insert retainers 296 in the form of projections 297 extending from the first and second plate segments 281 and 282 over the hook chambers 285 of the first and second insert slot segments 283 and 284. Each projection 297 begins at the lower surface 289 of the hook chamber 285 and extends over the hook chamber 285 a distance 298, whereby each projection 297 covers the hook chamber 285 while the hook chamber 285 remains configured to receive therein either the first hook 265 or the second hook 266 when the compression insert 258 resides in the insertion shape 262. The projection 297 due to the distance 298 allows the compression insert 258 in the insertion shape 262 to insert into the insert retaining pathway 293 such that the first and second hooks 265 and 266 insert into a respective hook chamber 285 while being spaced apart from the projection 297. Nevertheless, during attempted transition of the compression insert 258 from the insertion shape 262 to the natural shape 261 and the resulting attempted transition of the orthopedic implant 260 from the insertion position 292 to the natural position 291, the projections 297 due to the distances 298 block the compression insert 258 thereby retaining the compression insert 258 within the insert retaining pathway 293 because the first and second hooks 265 and 266 of the compression insert 258 respectively move under the projection 297.

FIGS. 27A-27D illustrate an insert delivery device 300 for the compression insert 148 of the second embodiment. The insert delivery device 300 includes a barrel 301 with a conduit 302 extending therefrom that terminates in an insert receiver 303 defining a cavity 304 shaped to hold the compression insert 148 therein when the compression insert 148 resides in the insertion shape 151. The insert delivery device 300 includes a plunger 305 with a shaft 306 extending therefrom integrated with the barrel 301 and the conduit 302. The plunger 305 includes a first or top end 307 and a second or bottom end 308 with a flange 309 thereabout. The shaft 306 at a proximal end 310 extends from the second or bottom end 308 of the plunger 305 below the flange 309 to a distal end 311.

The barrel 301 includes a first or top end 312, a second or bottom end 313, and a channel 314 therebetween including a cavity 314 adjacent the second or bottom end 313. The conduit 302 at a proximal end 315 extends from the second or bottom end 313 of the barrel 301 to a distal end 316 that opens into the insert receiver 303 while being connected therewith. The channel 314 is configured to receive therethrough the plunger 305 which is sized to extend from the first or top end 312 of the barrel 301. The cavity 314 is configured to receive therein the flange 309 of the plunger 305 and further is sized to permit movement of the flange 309 within the cavity 314 and thus the plunger 305 relative to the barrel 301. The shaft 306 extends from the cavity 314 and into the conduit 302 at the proximal end 315 thereof and further through the conduit 302 along the length thereof. The cavity 314 includes an elastic device 317 such as a spring located between the flange 309 and the second or bottom end 313 of the barrel 301 that maintains the plunger 305 in a pre-delivery position 318 whereby the shaft 306 at the distal end 311 thereof resides adjacent the distal end 316 of the conduit 302. A movement of the plunger 305 through a pushing thereof at the first or top end 307 transitions the plunger 305 from the pre-delivery position 318 to a delivery position 319 whereby the flange 309 compresses the elastic device 317 resulting in the shaft 306 exiting the conduit 302 at the distal end 316 thereof until the shaft 306 at the distal end 311 thereof extends beyond the insert receiver 303 and in particular the cavity 304 thereof. The elastic device 317 upon a release of the plunger 305 acts upon the flange 309 to return the plunger 305 from the delivery position 319 to the pre-delivery position 318.

A loading of the insert delivery device 300 residing in the pre-delivery position 318 includes placing a compression insert 148 deformed from the natural shape 150 to the insertion shape 151 into the cavity 304 of the insert receiver 303. After loading of the insert delivery device 300 with the compression insert 148, the compression insert 148 using the insert delivery device 300 may be positioned above an orthopedic implant 145 engaged with bone, bones, or bone pieces while residing in the insertion position 195 whereby the insert retaining pathway 196 thereof includes the second overall length 202. A movement of the plunger 305 from the pre-delivery position 318 to the delivery position 319 progresses the shaft 306 through the conduit 302 until the distal end 311 thereof extends beyond the insert receiver 303 and in particular the cavity 304 thereof. In accordance therewith, the shaft 306 engages the compression insert 148 and then pushes the compression insert 148 from the cavity 304 of the insert receiver 303 and thus the insert delivery device 300 such that the compression insert 148 in the insertion shape 151 inserts into the insert retaining pathway 196. Upon release from the insert delivery device 300, the compression insert 148 attempts to transition from the insertion shape 151 to the natural shape 150, resulting in the orthopedic implant 145 attempting to move from the insertion position 195 to the natural position 194, thereby continuously compressing the bone, bones, or bone pieces in order to affix the bone, bones, or bone pieces for a fusion and a healing thereof. Once the compression insert 148 disengages from the insert receiver 303 and in particular the cavity 304 thereof and thus the insert delivery device 300, a release of the plunger 305 allows the plunger 305 to return from the delivery position 319 to the pre-delivery position 318. One of ordinary skill in the art will recognize that an insert delivery device for the compression insert 258 would be substantially, completely identical to the insert delivery device 300, except the insert receiver and thus the cavity thereof for the insert delivery device would be shaped to hold the compression insert 258 therein when the compression insert 258 resides in the insertion shape 262.

Figure 28A:
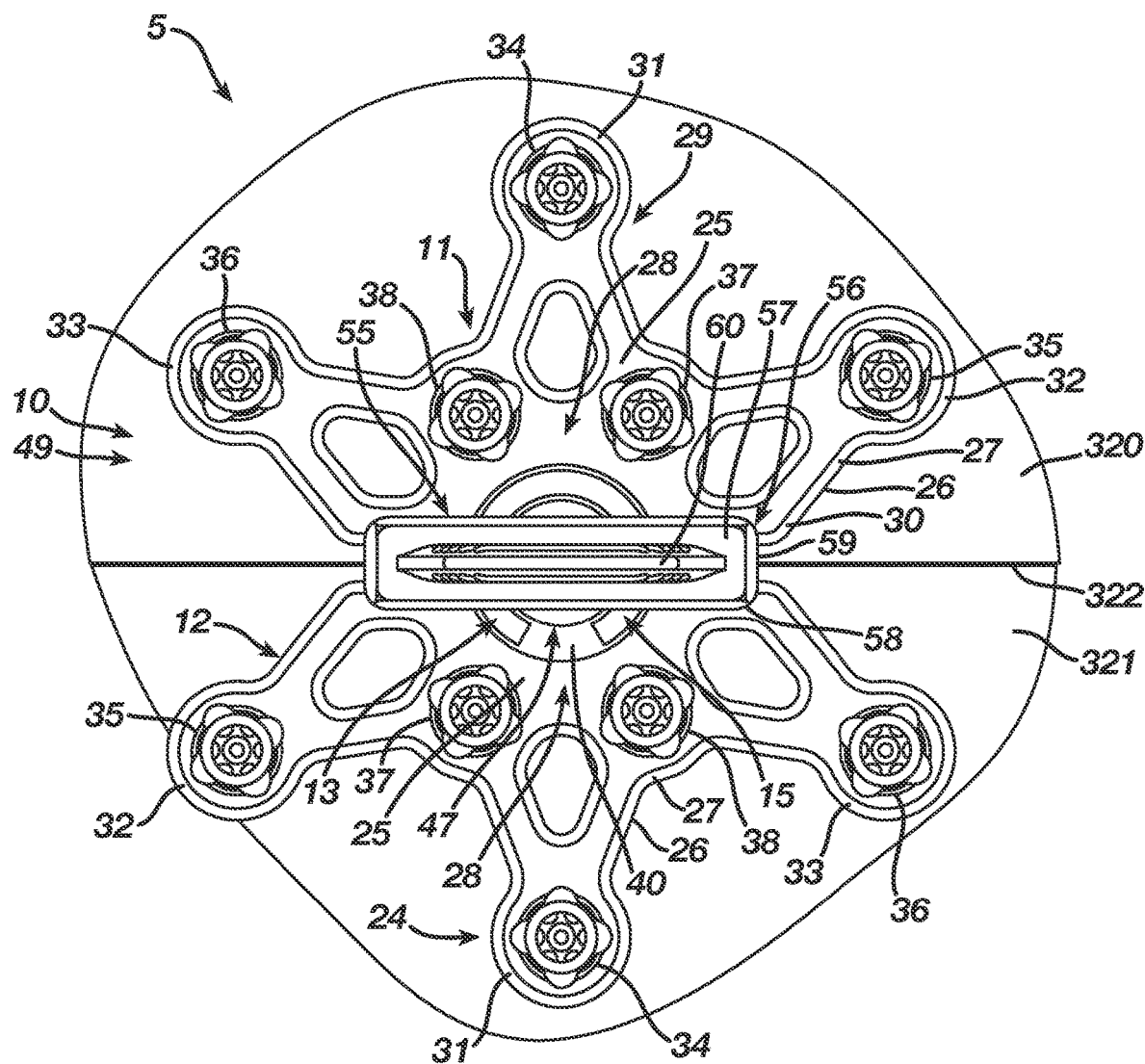
FIGS. 28A-28D are top views illustrating use of the orthopedic fixation system including the compression insert according to the first embodiment and the orthopedic implant according to the first embodiment to affix bone, bones, or bone pieces.

In accordance with the orthopedic fixation system 5, the implant retainer 55 as previously described retains the orthopedic implant 10 in the insertion position 49 and the compression insert 13 in the insertion shape 15 such that the implant 11 is ready for securing with bone, bones, or bone pieces, and, in particular, with a first bone 320 and a second bone 321, which are presented herein as an example. As illustrated in FIG. 28A, a surgeon aligns the first bone 320 with the second bone 321 at a fusion zone 322 in an orientation that promotes fixation of the first bone 320 with the second bone 321 and a proper healing thereof. The surgeon then places the implant 10 and the compression insert 13 held respectively in the insertion position 49 and the insertion shape by the implant retainer 55 across the first bone 320 and the second bone 321 at the fusion zone 322. More particularly, the surgeon places the first plate 11 atop the first bone 320 and the second plate 12 atop the second bone 321 such that the compression insert 13 spans the fixation zone 322 at the expansion 50. Upon placement of the implant 10, the surgeon secures the implant 10 with the first and second bones 320 and 321 using anchoring members in the form of bone screws inserted into the first and second bones 320 and 321 through the openings 34-37 and 37-38.

Figure 28B:
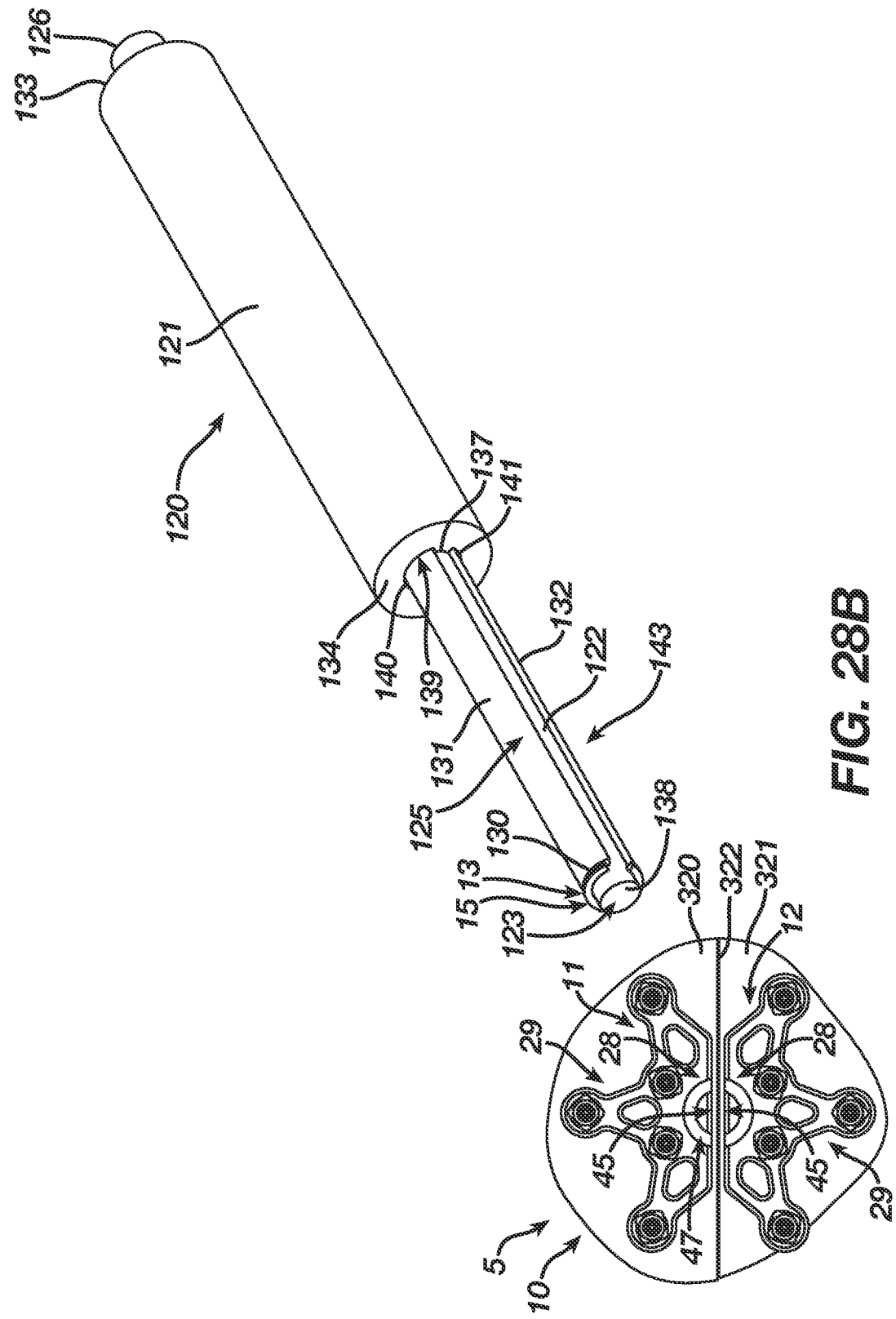

In the alternative as illustrated in FIG. 28B, the surgeon, after aligning the first bone 320 with the second bone 321 at the fusion zone 322, places the implant 10 in the insertion position 49 across the first bone 320 and the second bone 321 at the fusion zone 322. More particularly, the surgeon places the first plate 11 atop the first bone 320 and the second plate 12 atop the second bone 321 such that the first plate 11 is spaced apart from the second plate 12 across the fixation zone 322 by the expansion 50. Upon placement of the implant 10, the surgeon secures the implant with the first and second bones 320 and 321 using anchoring members in the form of bone screws inserted into the first and second bones 320 and 321 through the openings 34-37 and 37-38.

Figure 28C:
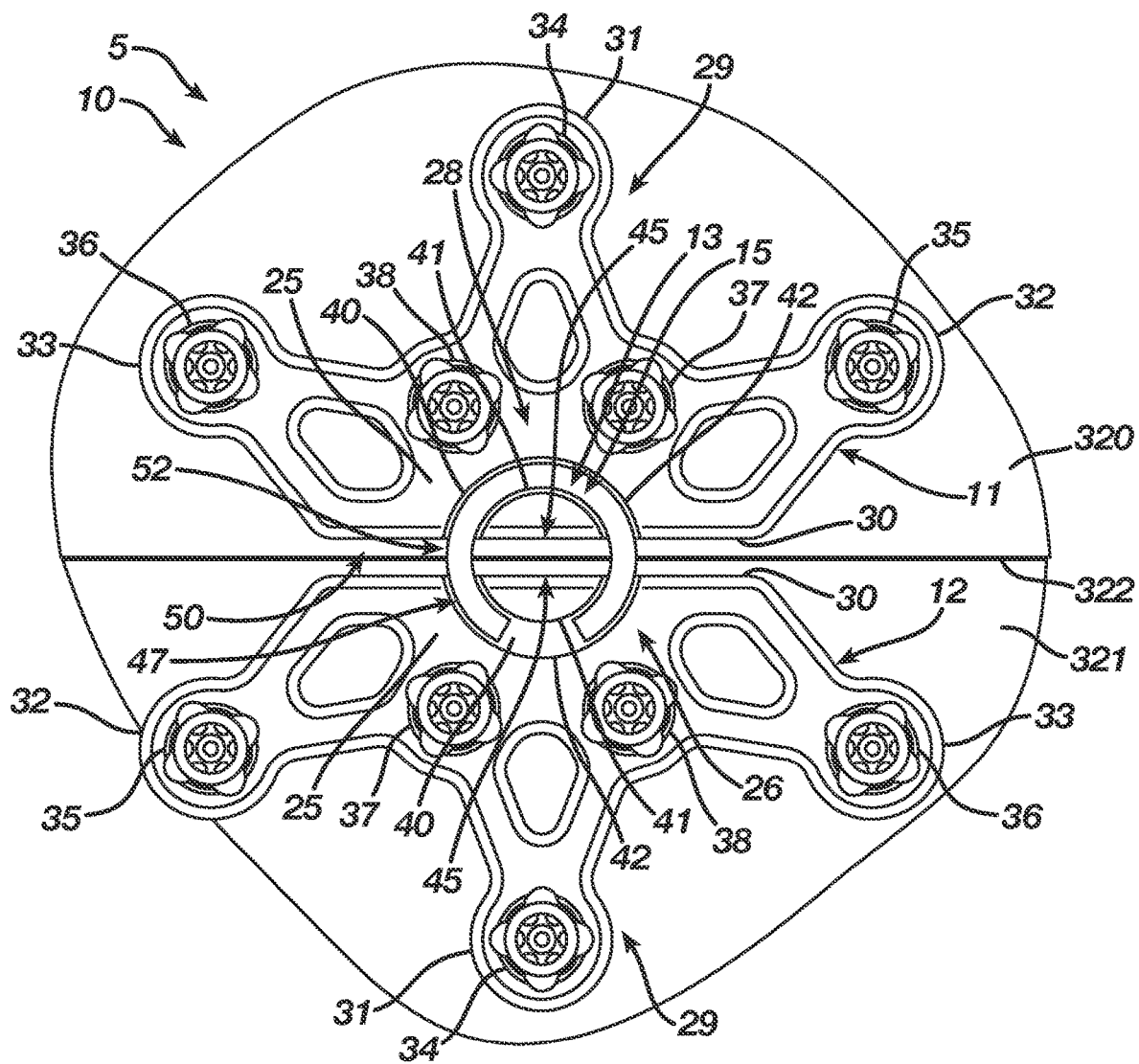
Figure 28D:
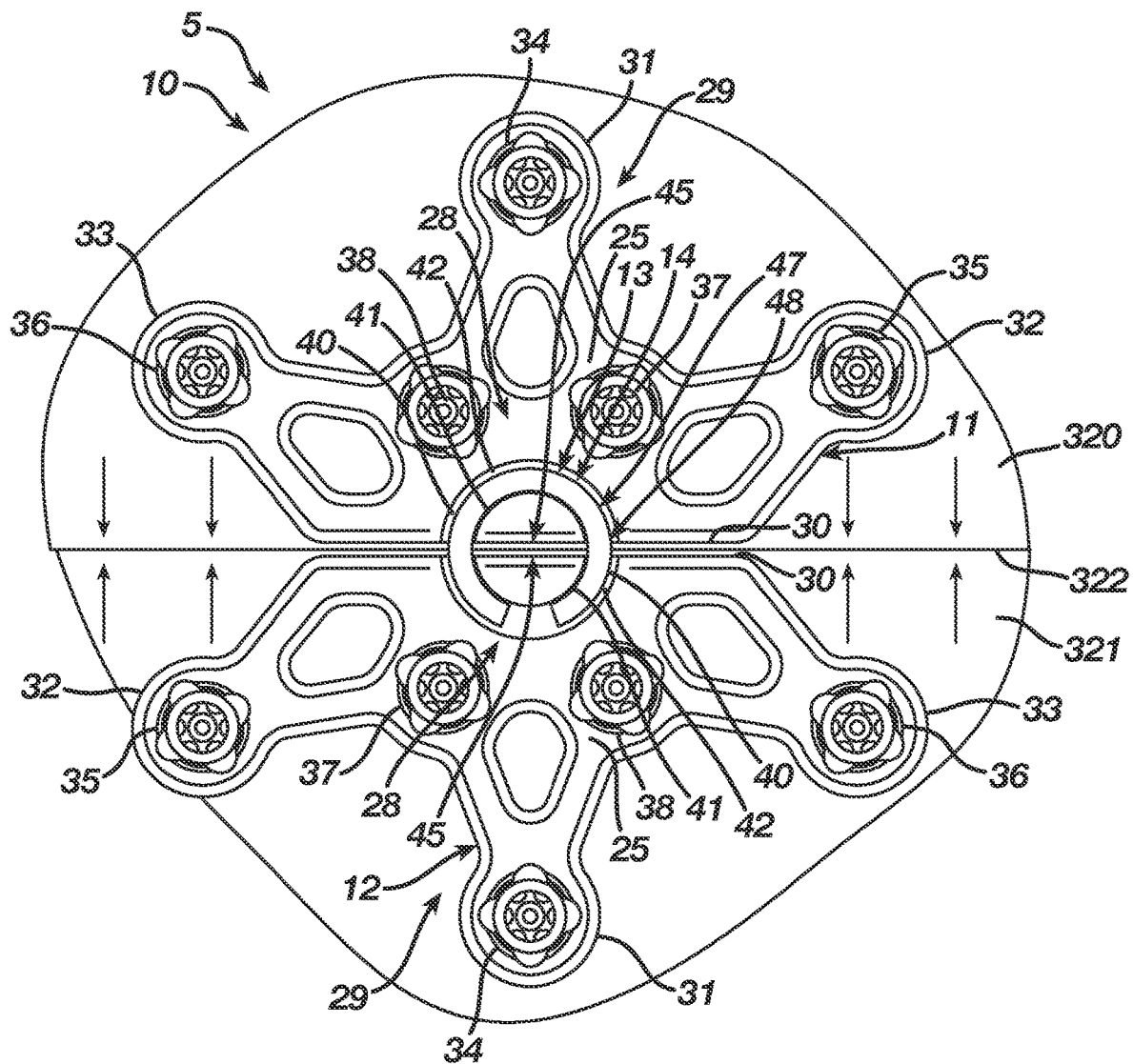

After affixing the implant 10 with the first and second bones 320 and 321 across the fusion zone 322, the surgeon as illustrated in FIG. 28C either removes the implant retainer 55 or delivers the compression insert 13 in the insertion shape 15 into the insert retaining pathway 47 using the insert delivery device 120. Upon removal of the implant retainer 55 or the delivery of the compression insert 13, the compression insert 13 as illustrated in FIG. 28D, due to its attempted transition from the insertion shape 15 to the natural shape 14, delivers the energy stored therein to the first plate 11 and the second plate 12 and thus the orthopedic implant 10, resulting in the orthopedic implant 10 attempting to move from the insertion position 49 to the natural position 46. In accordance therewith, the orthopedic implant 10 continuously compresses the first and second bones 320 and 321 at the fixation zone 322 thereof whereby the orthopedic fixation system 5 affixes the first and second bones 320 and 321 in order to promote a fusion and a healing thereof.

Figure 29A:
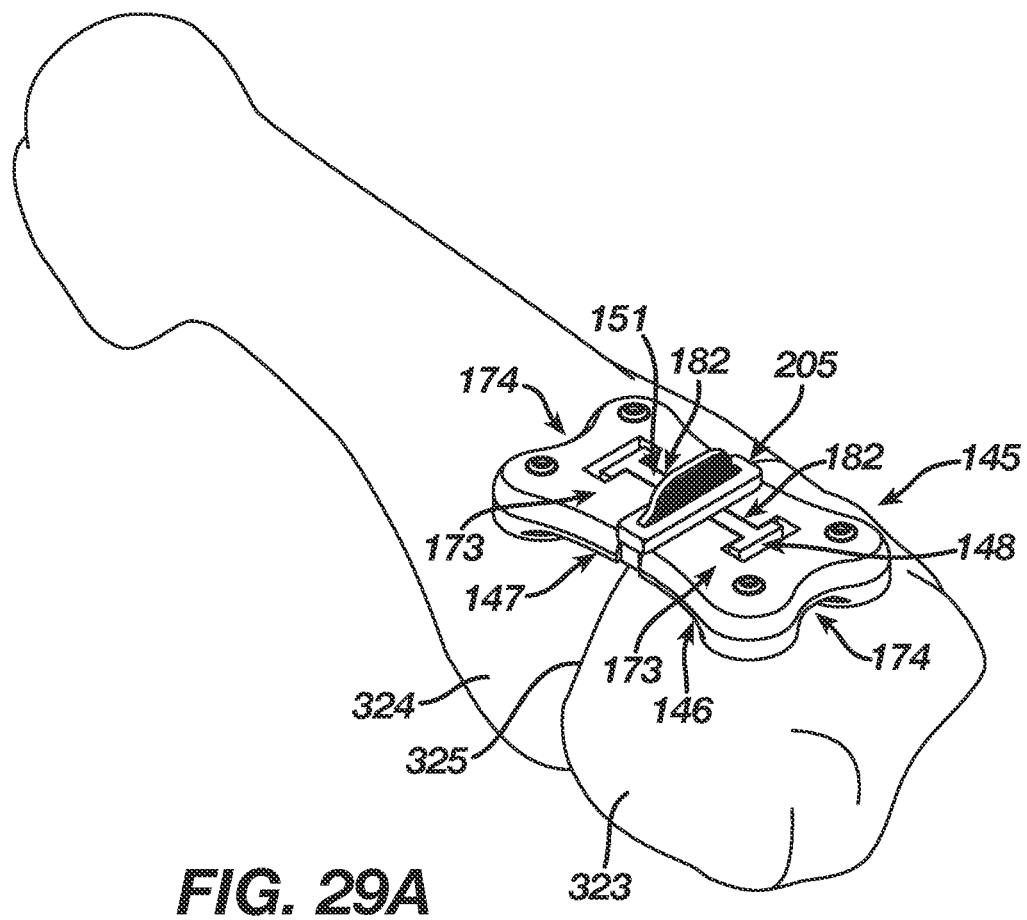
FIGS. 29A-29D are top views illustrating use of the orthopedic fixation system including the compression insert according to the second embodiment and the orthopedic implant according to the second embodiment to affix bone, bones, or bone pieces.

In accordance with the orthopedic fixation system 5, the implant retainer 205 as previously described retains the orthopedic implant 145 in the insertion position 195 and the compression insert 148 in the insertion shape 151 such that the implant 145 is ready for securing with bone, bones, or bone pieces, and, in particular, with a first bone 323 and a second bone 324, which are presented herein as an example. As illustrated in FIG. 29A, a surgeon aligns the first bone 323 with the second bone 324 at a fusion zone 325 in an orientation that promotes fixation of the first bone 323 with the second bone 324 and a proper healing thereof. The surgeon then places the implant 145 and the compression insert 148 held respectively in the insertion position 195 and the insertion shape 151 by the implant retainer 205 across the first bone 323 and the second bone 324 at the fusion zone 325. More particularly, the surgeon places the first plate 146 atop the first bone 323 and the second plate 147 atop the second bone 324 such that the compression insert 148 spans the fixation zone 325 at the expansion 200. Upon placement of the implant 145, the surgeon secures the implant 145 with the first and second bones 323 and 324 using anchoring members in the form of bone screws inserted into the first and second bones 323 and 324 through the openings 178-179.

Figure 29B:
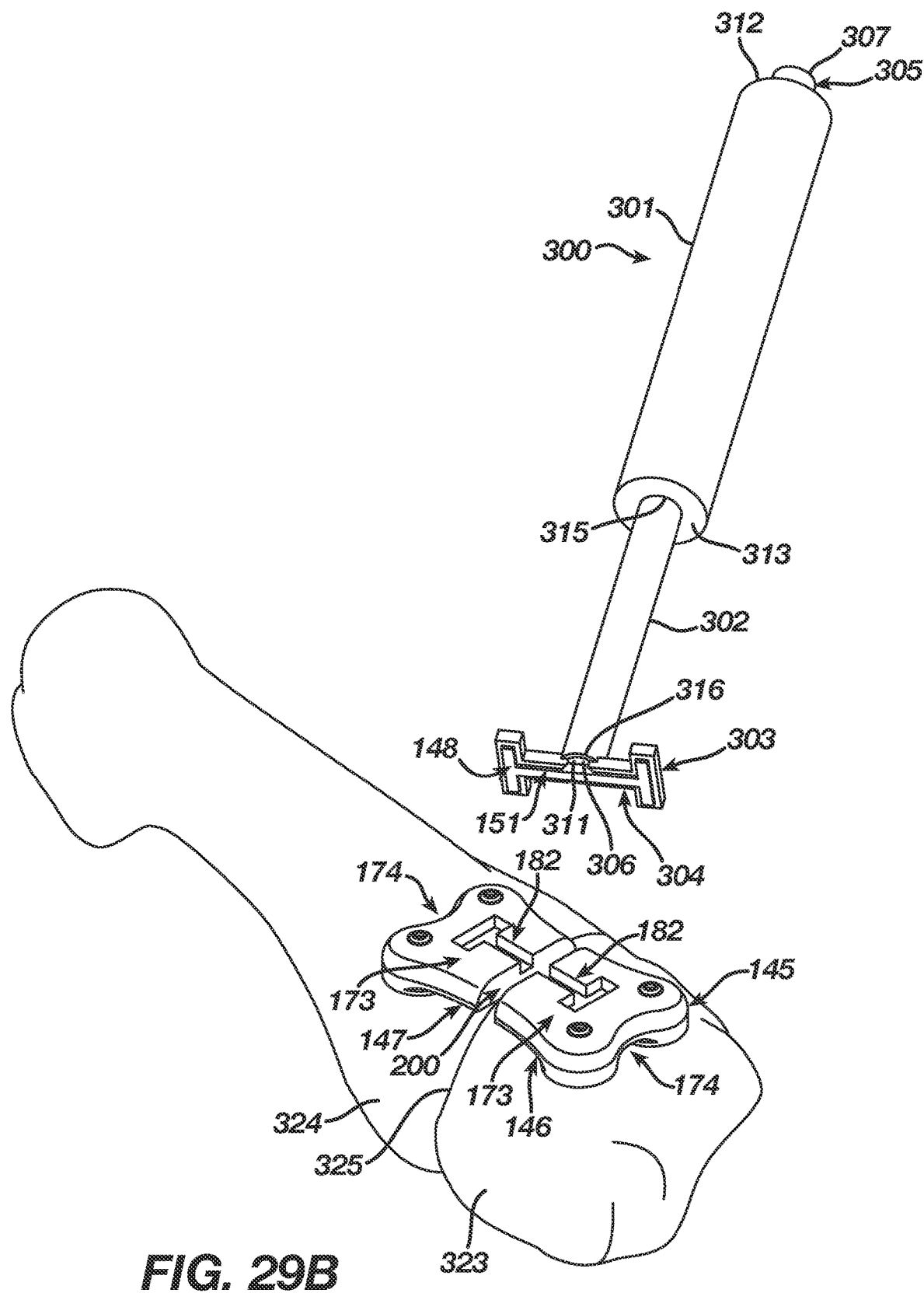

In the alternative as illustrated in FIG. 29B, the surgeon, after aligning the first bone 323 with the second bone 324 at the fusion zone 325, places the implant 145 in the insertion position 195 across the first bone 323 and the second bone 324 at the fusion zone 325. More particularly, the surgeon places the first plate 146 atop the first bone 323 and the second plate 147 atop the second bone 324 such that the first plate 146 is spaced apart from the second plate 147 across the fixation zone 325 by the expansion 200. Upon placement of the implant 145, the surgeon secures the implant 145 with the first and second bones 323 and 324 using anchoring members in the form of bone screws inserted into the first and second bones 323 and 324 through the openings 178-179.

Figure 29C:
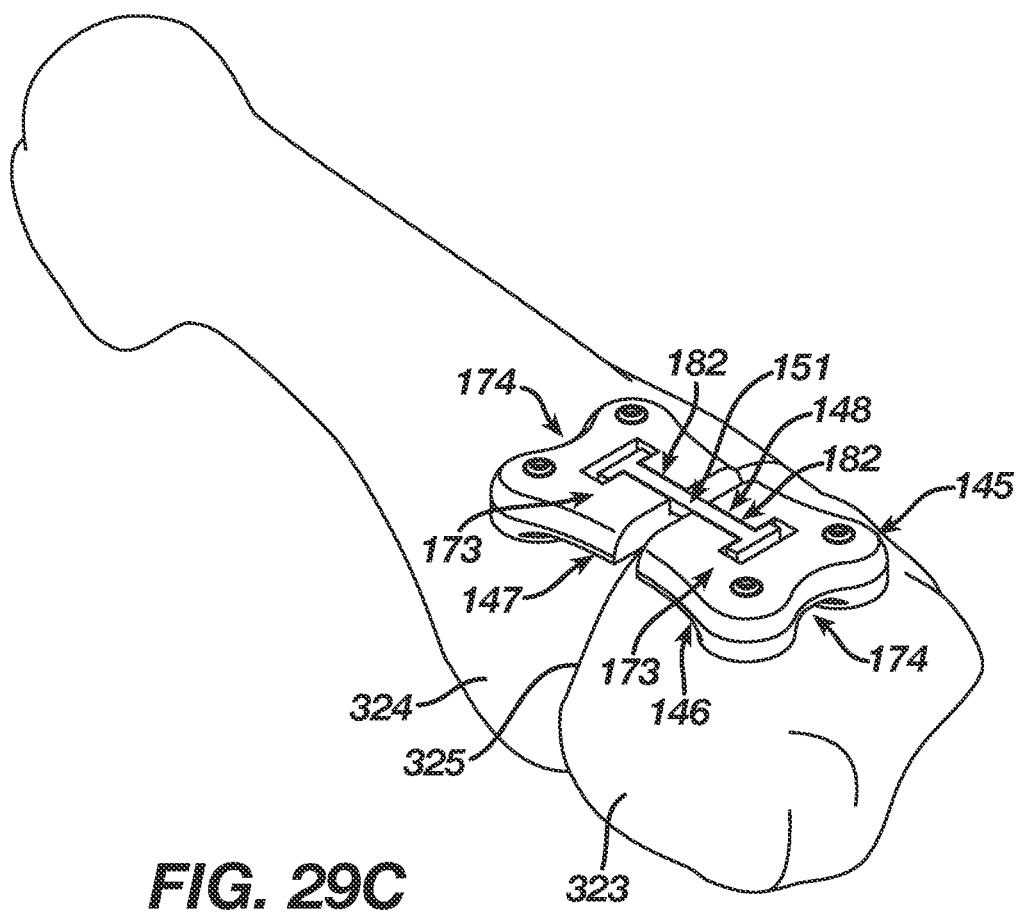
Figure 29D:
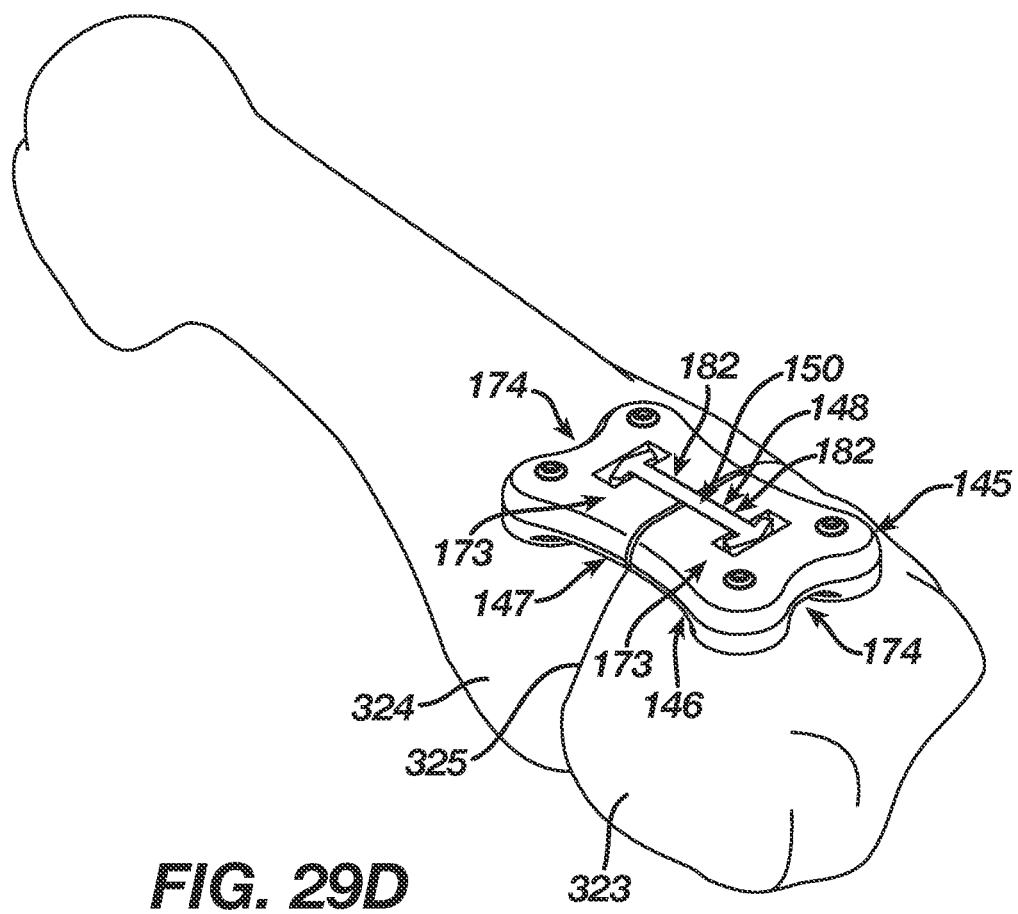

After affixing the implant 145 with the first and second bones 323 and 324 across the fusion zone 325, the surgeon as illustrated in FIG. 29C either removes the implant retainer 205 or delivers the compression insert 145 in the insertion shape 151 into the insert retaining pathway 196 using the insert delivery device 300. Upon removal of the implant retainer 205 or the delivery of the compression insert 148, the compression insert 13 as illustrated in FIG. 29D, due to its attempted transition from the insertion shape 151 to the natural shape 150, delivers the energy stored therein to the first plate 146 and the second plate 147 and thus the orthopedic implant 145, resulting in the orthopedic implant 145 attempting to move from the insertion position 195 to the natural position 194. In accordance therewith, the orthopedic implant 145 continuously compresses the first and second bones 323 and 324 at the fixation zone 325 thereof whereby the orthopedic fixation system 5 affixes the first and second bones 323 and 324 in order to promote a fusion and a healing thereof.

Although the present invention has been described in terms of the foregoing preferred embodiments, such description has been for exemplary purposes only and, as will be apparent to those of ordinary skill in the art, many alternatives, equivalents, and variations of varying degrees will fall within the scope of the present invention. That scope, accordingly, is not to be limited in any respect by the foregoing detailed description; rather, it is defined only by the claims that follow.

The invention claimed is:

1. An orthopedic fixation system adapted to affix a bone, comprising:
    a compression insert transitionable between a natural shape and an insertion shape, whereby the compression insert upon transition from the natural shape to the insertion shape stores energy, further whereby the compression insert upon transition from the insertion shape to the natural shape delivers the energy stored therein;
    an orthopedic implant, comprising a first plate including an insert slot configured to receive therein a portion of the compression insert and a second plate including an insert slot configured to receive therein a portion of the compression insert;
    the first plate and the second plate in an insertion position being adapted to secure with the bone in an opposed relationship with the first plate and the second plate spaced apart to produce an expansion therebetween, whereby the insert slot of the first plate and the insert slot of the second plate align across the expansion;
    the insert slot of the first plate, the insert slot of the second plate, and the expansion, when the first plate and the second plate reside in the insertion position, being configured to define an insert retaining pathway including dimensions greater than the compression insert in the insertion shape such that the insert retaining pathway receives therein the compression insert in the insertion shape while allowing transition within the insert retaining pathway of the compression insert from the insertion shape to the natural shape; and
    the compression insert, in the insertion shape, being adapted to insert into the insert retaining pathway with the compression insert residing within the insert slot of the first plate and the insert slot of the second plate while spanning the expansion, and the compression insert, due to an attempted transition thereof within the insert retaining pathway from the insertion shape to the natural shape, being adapted to deliver the energy stored therein to the first plate and the second plate whereby the orthopedic implant affixes the bone.

2. The orthopedic fixation system of claim 1, the first plate and the second plate, each comprising:
    a body section with a front face, whereby the body section includes the insert slot therein; and
    an anchoring section extending from the body section adapted to secure the first plate or the second plate with the bone.

3. The orthopedic fixation system of claim 1, the compression insert including a closed position when residing in the natural shape and an open position when residing in the insertion shape.

4. The orthopedic fixation system of claim 3, the insert slot of the first plate, the insert slot of the second plate, and the expansion, when the first plate and the second plate reside in the insertion position, being configured to define the insert retaining pathway with an overall length greater than the compression insert when transitioned to the open position such that the insert retaining pathway receives therein the compression insert in the insertion shape while allowing transition within the insert retaining pathway of the compression insert from the open position in the insertion shape to the closed position in the natural shape.

5. The orthopedic fixation system of claim 1, wherein:
    the first plate at a front face including a stabilizer extending therefrom;
    the second plate at a front face defining therein a cavity configured complementary in shape with the stabilizer;
    the stabilizer, when the first plate and the second plate reside in the insertion position, being configured to insert into the cavity in order to prevent a load experienced by the first plate and the second plate from moving the first plate and the second plate.

6. The orthopedic fixation system of claim 1, comprising an insert retainer projecting over the insert slot of one of the first plate and the second plate, whereby the insert retainer blocks the compression insert within the insert slot as the compression insert attempts transition from the insertion shape to the natural shape.

7. The orthopedic fixation system of claim 1, comprising an implant retainer configured to insert into the expansion between the first plate and the second plate whereby the implant retainer prevents transition of the compression insert from the insertion shape to the natural shape thereby maintaining the orthopedic implant in the insertion position.

8. An orthopedic fixation system adapted to affix a bone, comprising:
    a compression insert transitionable between a natural shape and an insertion shape, whereby the compression insert upon transition from the natural shape to the insertion shape stores energy, further whereby the compression insert upon transition from the insertion shape to the natural shape delivers the energy stored therein, the compression insert, comprising:
        a shaft terminating at a first end in a first beam including a first transition section and at a second end in a second beam including a second transition section,
        the first transition section and the second transition section in the natural shape of the compression insert being configured to contract respectively the first beam and the second beam into a closed position; and the first transition section and the second transition section in the insertion shape of the compression insert being configured to expand respectively the first beam and the second beam into an open position;

an orthopedic implant, comprising a first plate including an insert slot configured to receive therein a portion of the compression insert and a second plate including an insert slot configured to receive therein a portion of the compression insert;

the first plate and the second plate in an insertion position being adapted to secure with the bone in an opposed relationship with the first plate and the second plate spaced apart to produce an expansion therebetween, whereby the insert slot of the first plate and the insert slot of the second plate align across the expansion; and the compression insert, in the insertion shape, being adapted to insert into the insert slot of the first plate and the insert slot of the second plate such that the compression insert spans the expansion, and the compression insert, due to an attempted transition thereof from the insertion shape to the natural shape, being adapted to deliver the energy stored therein to the first plate and the second plate whereby the orthopedic implant affixes the bone.

9. The orthopedic fixation system of claim 8, the insert slot of the first plate, the insert slot of the second plate, and the expansion, when the first plate and the second plate reside in the insertion position, being configured to define an insert retaining pathway with dimensions greater than the compression insert when transitioned to the open position such that the insert retaining pathway receives therein the compression insert in the insertion shape.

10. The orthopedic fixation system of claim 8, the first plate and the second plate, each comprising:
a body section with a front face, whereby the body section includes the insert slot therein; and
an anchoring section extending from the body section adapted to secure the first plate or the second plate with the bone.

11. The orthopedic fixation system of claim 10, the insert slot in each of the first plate and the second plate, comprising:
a chamber communicating with a channel defining an opening at the front face;
the channel configured to receive therein a portion of the shaft of the compression insert;
the chamber configured to receive therein one of the first beam and the second beam expanded into the open position while allowing a contraction of one of the first beam and the second beam into the closed position.

12. The orthopedic fixation system of claim 11, the chamber and the channel of the insert slot of the first plate, the chamber and the channel of the insert slot of the second plate, and the expansion, when the first plate and the second plate reside in the insertion position, being configured to define an insert retaining pathway with dimensions greater than the compression insert when transitioned to the open position such that the insert retaining pathway receives therein the compression insert in the insertion shape.

13. An orthopedic fixation system adapted to affix a bone, comprising:
a compression insert transitionable between a natural shape and an insertion shape, whereby the compression insert upon transition from the natural shape to the insertion shape stores energy, further whereby the compression insert upon transition from the insertion shape to the natural shape delivers the energy stored therein;
an insert delivery device, comprising:
a barrel with a conduit extending therefrom that terminates in an insert receiver shaped to hold therein the compression insert in the insertion shape,
a plunger with a shaft extending therefrom, the plunger being integrated with the barrel such that the shaft extends through the conduit, and
the plunger being moveable between a pre-delivery position that allows loading of the compression insert in the insertion shape into the insert receiver and a delivery position whereby the shaft pushes the compression insert from the insert receiver;
an orthopedic implant, comprising a first plate including an insert slot configured to receive therein a portion of the compression insert and a second plate including an insert slot configured to receive therein a portion of the compression insert;
the first plate and the second plate in an insertion position being adapted to secure with the bone in an opposed relationship with the first plate and the second plate spaced apart to produce an expansion therebetween, whereby the insert slot of the first plate and the insert slot of the second plate align across the expansion; and
the compression insert, in the insertion shape, being adapted to insert into the insert slot of the first plate and the insert slot of the second plate such that the compression insert spans the expansion, and the compression insert, due to an attempted transition thereof from the insertion shape to the natural shape, being adapted to deliver the energy stored therein to the first plate and the second plate whereby the orthopedic implant affixes the bone.

* * * * *